United States Patent
Zou et al.

(10) Patent No.: US 9,618,513 B2
(45) Date of Patent: Apr. 11, 2017

(54) COMPOSITIONS AND METHODS FOR DETECTING AND TREATING COLORECTAL CANCER

(71) Applicant: The Regents of the University of Michigan, Ann Arbor, MI (US)

(72) Inventors: Weiping Zou, Ann Arbor, MI (US); Ilona Kryczek, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/605,519

(22) Filed: Jan. 26, 2015

(65) Prior Publication Data

US 2015/0212088 A1 Jul. 30, 2015

Related U.S. Application Data

(60) Provisional application No. 61/931,891, filed on Jan. 27, 2014.

(51) Int. Cl.

| | |
|---|---|
| *G01N 33/574* | (2006.01) |
| *C07K 16/24* | (2006.01) |
| *A61K 31/7076* | (2006.01) |
| *A61K 45/06* | (2006.01) |
| *C12N 15/113* | (2010.01) |
| *C12Q 1/68* | (2006.01) |
| *A61K 31/7105* | (2006.01) |
| *A61K 31/713* | (2006.01) |

(52) U.S. Cl.
CPC ... *G01N 33/57419* (2013.01); *A61K 31/7076* (2013.01); *A61K 31/713* (2013.01); *A61K 31/7105* (2013.01); *A61K 45/06* (2013.01); *C07K 16/244* (2013.01); *C12N 15/1136* (2013.01); *C12N 15/1137* (2013.01); *C12Q 1/6886* (2013.01); *C12Y 201/01043* (2013.01); *C07K 2317/76* (2013.01); *C12N 2310/14* (2013.01); *C12N 2310/531* (2013.01); *C12Q 2600/158* (2013.01); *G01N 2333/4706* (2013.01); *G01N 2333/54* (2013.01); *G01N 2333/91017* (2013.01)

(58) Field of Classification Search
None
See application file for complete search history.

(56) References Cited

PUBLICATIONS

Ma et al (World J Gastroenterol, 2004, 10(11): 1569-1573).*
Morikawa et al (Clin Cancer Res, 2011, 17(6): 1452-1462).*
Wang et al (Anticancer Res, 2013, 33(10): 4279-4284).*
Xiong et al (Neoplasia, 2008, 10(3): 287-297).*
Gao et al (Clin Cancer Res, 2005, 11(17): 6333-6341).*
The Cancer Genome Atlas Network, "Comprehensive molecular characterization of human colon and rectal cancer," Nature 487, 2012, 330-337.
Aujla, S.J., et al., "IL-22 mediates mucosal host defense against Gram-negative bacterial pneumonia." Nat Med, 2008, 14(3): 275-281.
Barski, A., et al., "High-resolution profiling of histone methylations in the human genome." Cell, 2007, 129(4):823-37.
Basu, R., et al., "Th22 Cells are an Important Source of IL-22 for Host Protection against Enteropathogenic Bacteria." Immunity, 2012, 37(6): 1061-1075.
Bendall, S.C., et al., "IGF and FGF cooperatively establish the regulatory stem cell niche of pluripotent human cells in vitro." Nature, 2007, 448, 1015-1021.
Bi X, et al., "Proteomic Analysis of Colorectal Cancer Reveals Alterations in Metabolic Pathways Mechanism of Tumorigenesis." Mol Cell Proteomics, 2006, 5(6):1119-30.
Birney, E., et al., "Identification and analysis of functional elements in 1% of the human genome by the ENCODE pilot project." Nature, 2007, 447, 799-816.
Brabletz, T., Jet al., "Opinion: migrating cancer stem cells—an integrated concept of malignant tumour progression." Nat Rev Cancer, 2005, 5(9):744-9.
Cao, R., and Zhang, Y., "The functions of E(Z)/EZH2-mediated methylation of lysine 27 in histone H3." Curr Opin Genet Dev, 2004, 14, 155-164.
Carpentino, J.E.et al., "Aldehyde dehydrogenase-expressing colon stem cells contribute to tumorigenesis in the transition from colitis to cancer." Cancer Res, 2009, 69(20):8208-8215.
Cella, M. et al., "A human NK cell subset provides an innate source of IL-22 for mucosal immunity." Nature, 2009, 457, 722-725.
Cook, D. N., et al., "CCR6 mediates dendritic cell localization, lymphocyte homeostasis, and immune responses in mucosal tissue." Immunity, 2000, 12, 495-503.
Corvinus, F. M., et al., "Persistent STAT3 activation in colon cancer is associated with enhanced cell proliferation and tumor growth. Neoplasia." Neoplasia, 2005, 7:545-555.
Crellin, N. K., et al., "Human NKp44+IL-22+ cells and LTi-like cells constitute a stable RORC+ lineage distinct from conventional natural killer cells." J Exp Med 2010, 207(2): 281-290.
Cunningham, D., et al., "Colorectal cancer." Lancet, 2010, 375(9719):1030-47.
Curiel, T.J. et al., "Blockade of B7-H1 improves myeloid dendritic cell-mediated antitumor immunity." Nat Med, 2003, 9(5):562-7.

(Continued)

*Primary Examiner* — Sean Aeder
(74) *Attorney, Agent, or Firm* — Casimir Jones, SC

(57) ABSTRACT

The present invention relates to compositions and methods for the detecting, treating, and empirically investigating the interaction between a subject's immune system and cancer stem cells. In particular, the present invention provides compositions and methods for using IL-22 cytokine signaling and/or downstream targets of IL-22 cytokine signaling (e.g., STAT3, DOT1L, SUZ12, EED) in the diagnosis, treatment, and empirical investigation of cancers characterized with cancer stem cells activated through IL-22 cytokine signaling.

1 Claim, 22 Drawing Sheets

(56) References Cited

PUBLICATIONS

Curiel, T.J. et al., "Specific recruitment of regulatory T cells in ovarian carcinoma fosters immune privilege and predicts reduced survival." Nat Med, 2004, 10(9):942-9.

Daigle, S.R. et al., "Selective killing of mixed lineage leukemia cells by a potent small-molecule DOT1L inhibitor." Cancer Cell, 2011, 20(1):53-65.

Darnell, J. E., "Validating Stat3 in cancer therapy." Nature medicine, 2005, 11, 595-596.

Dawson, M. A., and Kouzarides, T., "Cancer epigenetics: from mechanism to therapy." Cell, 2012, 150, 12-27.

Dean, M. et al., "Tumour stem cells and drug resistance." Nat Rev Cancer, 2005, 5(4):275-84.

Dudakov, J.A. et al., "Interleukin-22 Drives Endogenous Thymic Regeneration in Mice." Science, 2012, 336, 91-95.

Duhen, T. et al., "Production of interleukin 22 but not interleukin 17 by a subset of human skin-homing memory T cells." Nat Immunol, 2009, 10, 857-863.

Dumoutier, L, et al., "Cloning and Characterization of IL-10-Related T Cell-Derived Inducible Factor (IL-TIF), a Novel Cytokine Structurally Related to IL-10 and Inducible by IL-91." Journal of immunology, 2000, 164(4), 1814-1819.

Dunn, G.P. et al., "Cancer immunoediting: from immunosurveillance to tumor escape." (2002) Nat Immunol, 2002, 3 (11):991-8.

Galon, J. et al., "Type, Density, and Location of Immune Cells Within Human Colorectal Tumors Predict Clinical Outcome." Science, 2006, 313, 1960-1964.

Hanash, A.M. et al., "Interleukin-22 Protects Intestinal Stem Cells from Immune-Mediated Tissue Damage and Regulates Sensitivity to Graft versus Host Disease." Immunity, 2012, 37, 339-350.

Honda, K., "IL-22 from T Cells: Better Late than Never." Immunity, 2012, 37, 952-954.

Huber, S. et al., "IL-22BP is regulated by the inflammasome and modulates tumorigenesis in the intestine." Nature, 2012, 491, 259-263.

Hutchins, A.P. et al., "Distinct transcriptional regulatory modules underlie STAT3's cell type-independent and cell type-specific functions." Nucleic Acids Res, 2013, 41(4):2155-70.

Jiang, R., et al., "Interleukin-22 promotes human hepatocellular carcinoma by activation of STA3." Hepatology, 2011, 54(3): 900-909.

Jing, N., and Tweardy, D. J., "Targeting Stat3 in cancer therapy." Anti-cancer drugs, 2005, 16(6): 601-607.

Kawada, K., et al., "Chemokine receptor CXCR3 promotes colon cancer metastasis to lymph nodes." Oncogene, 2007, 26, 4679-4688.

Kirchberger, S., et al., "Innate lymphoid cells sustain colon cancer through production of interleukin-22 in a mouse model." The Journal of experimental medicine, 2013, 210(5): 917-931.

Kleer, C. G., et al., "EZH2 is a marker of aggressive breast cancer and promotes neoplastic transformation of breast epithelial cells." Proc Natl Acad Sci U S A, 2003, 100(20), 11606-11611.

Kryczek, I. et al., "Expression of aldehyde dehydrogenase and CD133 defines ovarian cancer stem cells." Int J Cancer, 2012, 130(1): 29-39.

Kryczek, I., et al., "B7-H4 expression identifies a novel suppressive macrophage population in human ovarian carcinoma." J Exp Med, 2006, 203(4):871-81.

Kryczek, I., et al., "Human TH17 Cells Are Long-Lived Effector Memory Cells." Sci Transl Med, 2011, 3(104), p. 104ra100.

Lee, H., et al., "Persistently Activated Stat3 Maintains Constitutive NF-κB Activity in Tumors." Cancer Cell, 2009, 15, 283-293.

Lee, J. S., et al., "AHR drives the development of gut ILC22 cells and postnatal lymphoid tissues via pathways dependent on and independent of Notch." Nat Immunol, 2011, 13(2): 144-151.

Lejeune, D. et al., "Interleukin-22 (IL-22) activates the JAK/STAT, ERK, JNK, and p38 MAP kinase pathways in a rat hepatoma cell line. Pathways that are shared with and distinct from IL-10." J Biol Chem, 2002, 277(37): 33676-33682.

Matsushita, H. et al., "Cancer exome analysis reveals a T-cell-dependent mechanism of cancer immunoediting." Nature, 2012, 482, 400-404.

Mimori, K., et al., "Clinical significance of enhancer of zeste homolog 2 expression in colorectal cancer cases." Eur J Surg Oncol, 2005, 31(4):376-80.

Min, J., et al., "Structure of the catalytic domain of human DOT1L, a non-SET domain nucleosomal histone methyltransferase." Cell, 2003, 112(5):711-23.

Mohan, M. et al., "Linking H3K79 trimethylation to Wnt signaling through a novel Dot1-containing complex (DotCom)." Genes Dev, 2010, 24(6): 574-589.

Ng, H.H. et al., "Lysine methylation within the globular domain of histone H3 by Dot1 is important for telomeric silencing and Sir protein association." Genes Dev, 2002, 16, 1518-1527.

Pardal, R., et al., "Applying the principles of stem-cell biology to cancer." Nat Rev Cancer, 2003, 3(12), 895-902.

Pardoll, D.M., "The blockade of immune checkpoints in cancer immunotherapy." Nat Rev Cancer, 2012, 12 (4):252-64.

Pickert, G., et al., "STAT3 links IL-22 signaling in intestinal epithelial cells to mucosal wound healing." J Exp Med, 2009, 206(7): 1465-1472.

Pirker, R., et al., "EGFR expression as a predictor of survival for first-line chemotherapy plus cetuximab in patients with advanced non-small-cell lung cancer: analysis of data from the phase 3 FLEX study."Lancet Oncol., 2012, 13 (1):33-42.

Reya, T., et al., "Stem cells, cancer, and cancer stem cells." Nature, 2001, 414(6859): 105-111.

Rutz, S., et al., "IL-22, not simply a Th17 cytokine." Immunological reviews, 2013, 252, 116-132.

Scadden, D.T., "The stem-cell niche as an entity of action." Nature, 2006, 441(7097):1075-9.

Smith, J.J., et al., "Experimentally derived metastasis gene expression profile predicts recurrence and death in patients with colon cancer." Gastroenterology, 2010, 138(3):958-68.

Sonnenberg, G.F., et al., "Innate Lymphoid Cells Promote Anatomical Containment of Lymphoid-Resident Commensal Bacteria." (2012) Science 336, 1321-1325.

Sonnenberg, G.F., et al., "Pathological versus protective functions of IL-22 in airway inflammation are regulated by IL-17A." J Exp Med, 2010, 207, 1293-1305.

Spits, H., and Cupedo, T., "Innate lymphoid cells: emerging insights in development, lineage relationships, and function." Annu Rev Immunol, 2012, 30, 647-675.

Spits, H., and Di Santo, J. P., "The expanding family of innate lymphoid cells: regulators and effectors of immunity and tissue remodeling." Nat Immunol, 2011 12, 21-27.

Subramanian, A., et al., "GSEA-P: a desktop application for Gene Set Enrichment Analysis." Bioinformatics, 2007 23, 3251-3253.

Thompson, C.L., et al., "Interleukin-22 genetic polymorphisms and risk of colon cancer ." Cancer Causes Control, 2010, 21, 1165-1170.

Trifari, S., et al., "Identification of a human helper T cell population that has abundant production of interleukin 22 and is distinct from TH-17, TH1 and TH2 cells." Nat Immunol, 2009, 10, 864-871.

Varambally, S., et al., "The polycomb group protein EZH2 is involved in progression of prostate cancer." Nature, 2002, 419, 624-629.

Vermeulen, L, et al., "The developing cancer stem-cell model: clinical challenges and opportunities." Lancet Oncol, 2012, 13(2), e83-89.

Wolk, K., et al., "IL-22 increases the innate immunity of tissues." Immunity, 2004, 21, 241-254.

Yu, H., et al., "Crosstalk between cancer and immune cells: role of STAT3 in the tumour microenvironment." Nat Rev Immunol, 2007, 7, 41-51.

Yu, W. et al., "Catalytic site remodelling of the DOT1L methyltransferase by selective inhibitors." Nat Commun, 2012, 3, 1288.

Yue, P., and Turkson, J., "Targeting STAT3 in cancer: how successful are we?." Expert opinion on investigational drugs, 2009, 18(1), 45-56.

(56) References Cited

OTHER PUBLICATIONS

Zheng, Y. et al., "Interleukin-22 mediates early host defense against attaching and effacing bacterial pathogens." Nat Med, 2008, 14, 282-289.

Zheng, Y., et al., "Interleukin-22, a TH17 cytokine, mediates IL-23-induced dermal inflammation and acanthosis." Nature, 2007, 445, 648-651.

Zou, W., "Immunosuppressive networks in the tumour environment and their therapeutic relevance." Nat Rev Cancer, 2005, 5(4): 263-274.

Zou W. et al., "Early cytokine and chemokine gene expression in lymph nodes of macaques infected with simian immunodeficiency virus is predictive of disease outcome and vaccine efficacy." J Virol, 1997, 71, 1227-1236.

Zou, W., et al., "Stromal-derived factor-1 in human tumors recruits and alters the function of plasmacytoid precursor dendritic cells." Nat Med, 2001 7, 1339-1346.

\* cited by examiner

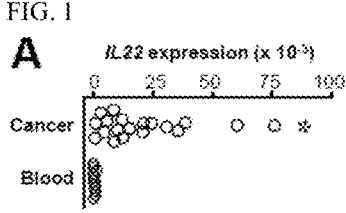
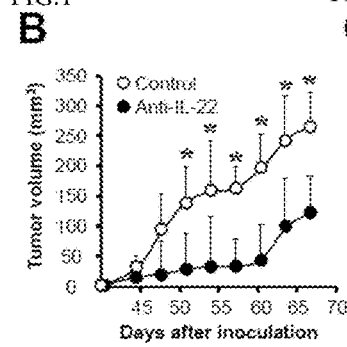
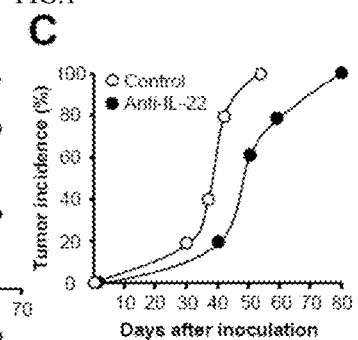
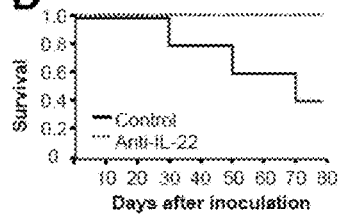
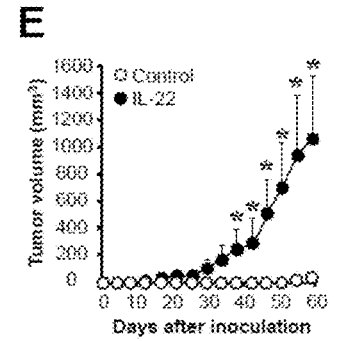
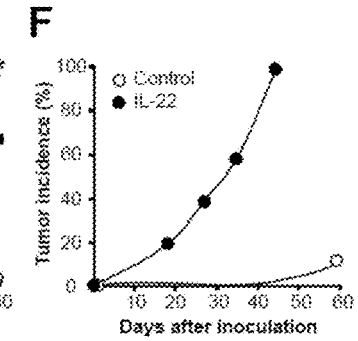
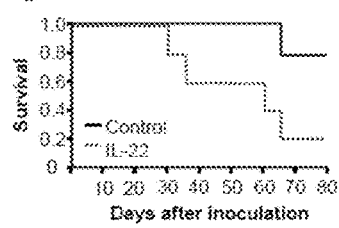
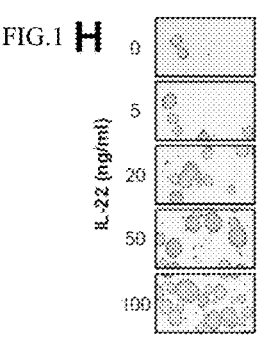
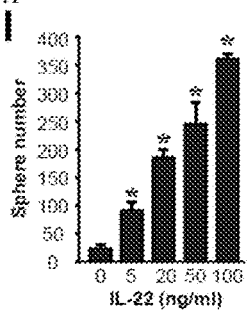
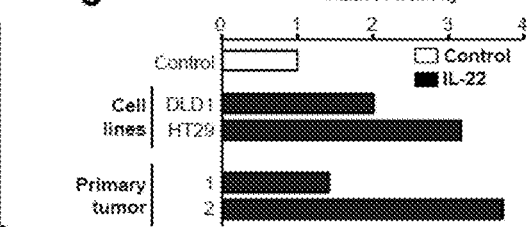
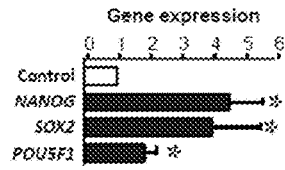
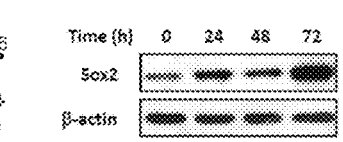
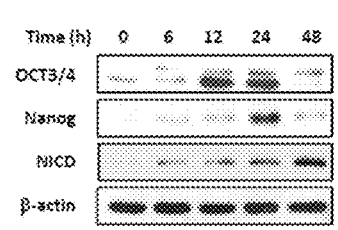
FIG. 1

FIG. 8
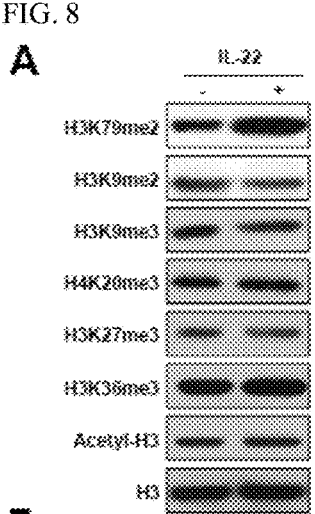 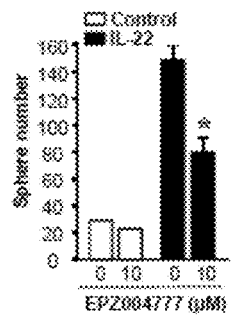 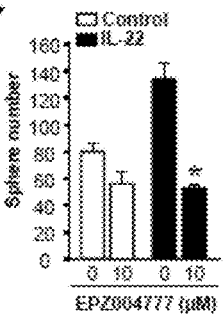
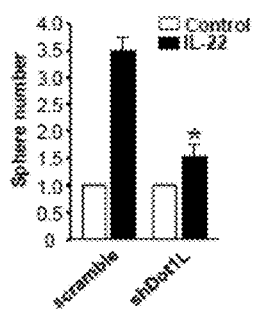 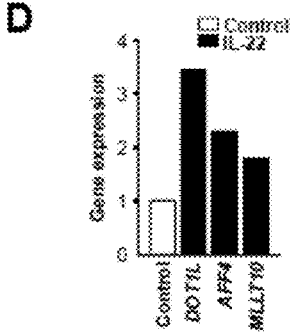 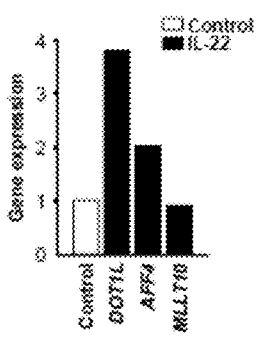
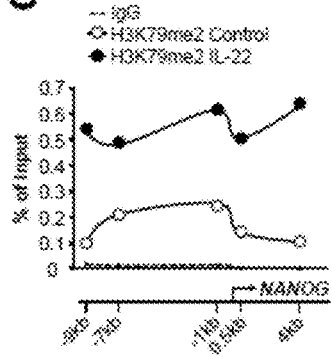 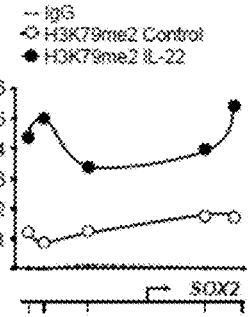 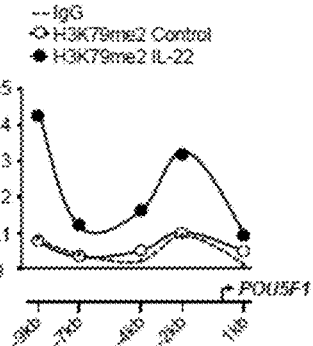
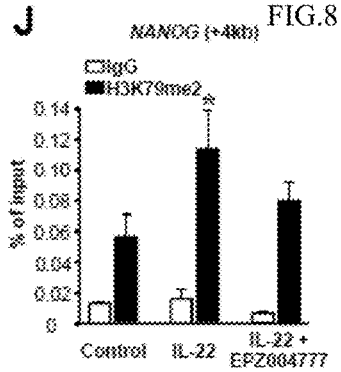 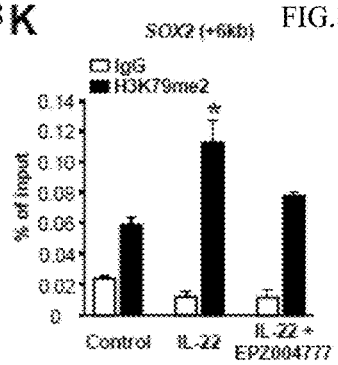 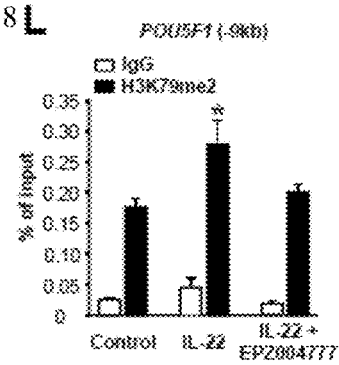

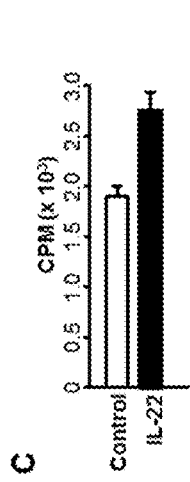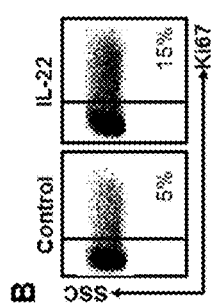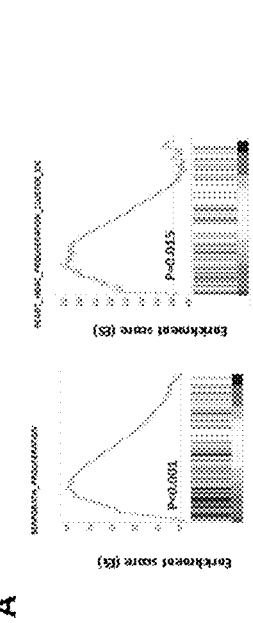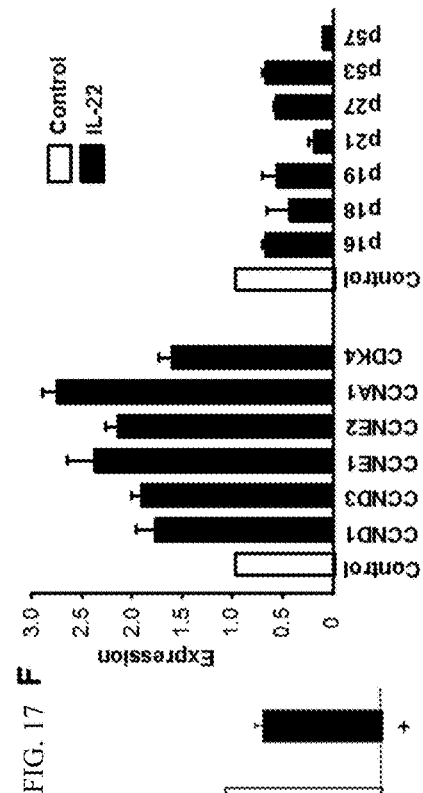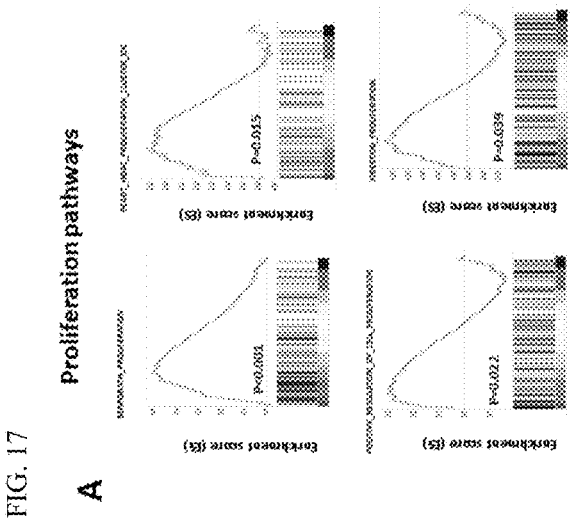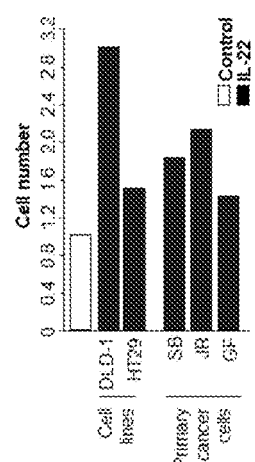
FIG. 17 A
FIG. 17 B
FIG. 17 C
FIG. 17 D
FIG. 17 E
FIG. 17 F FIG. 18
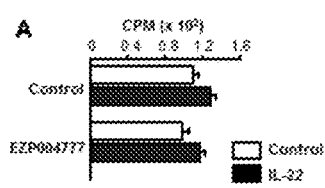
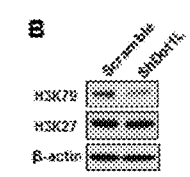
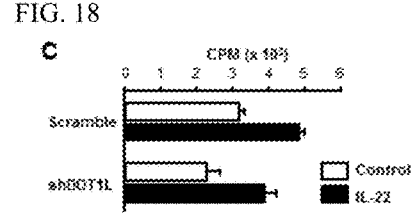
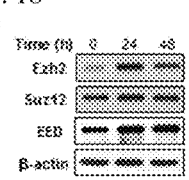
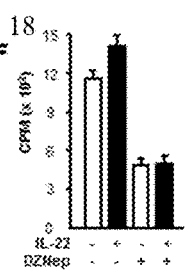
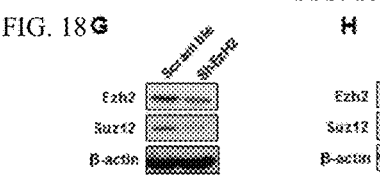
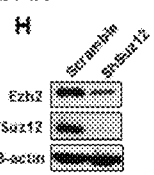
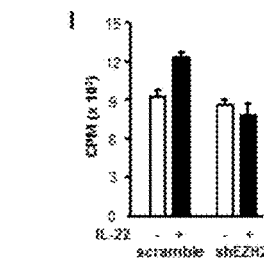
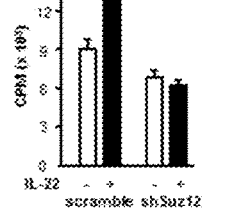
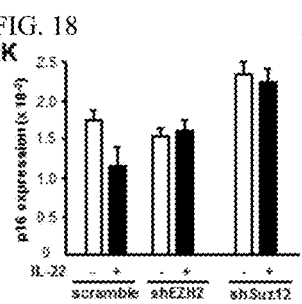
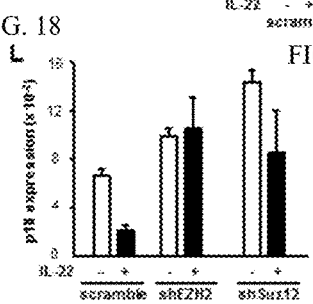
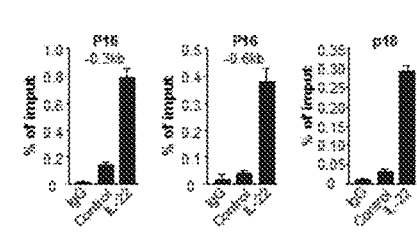

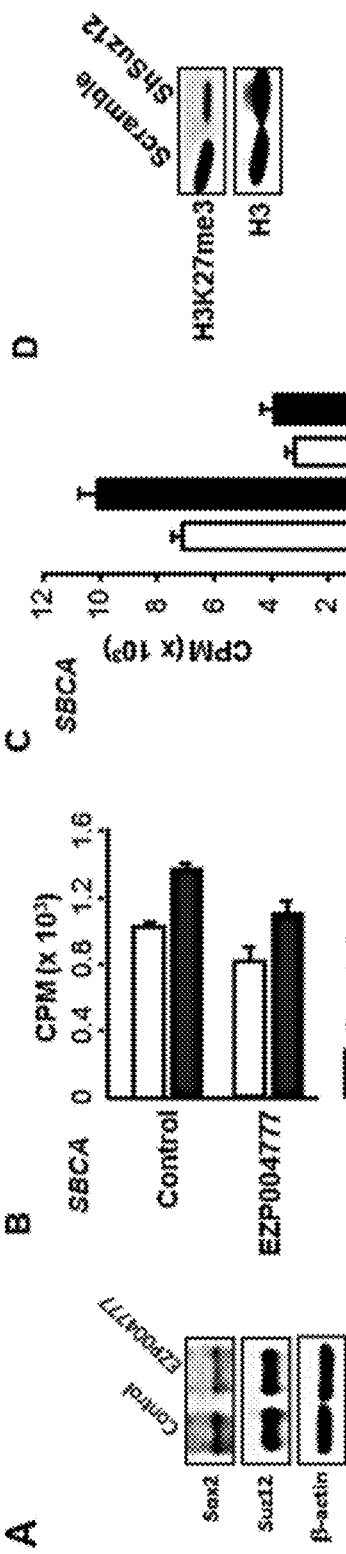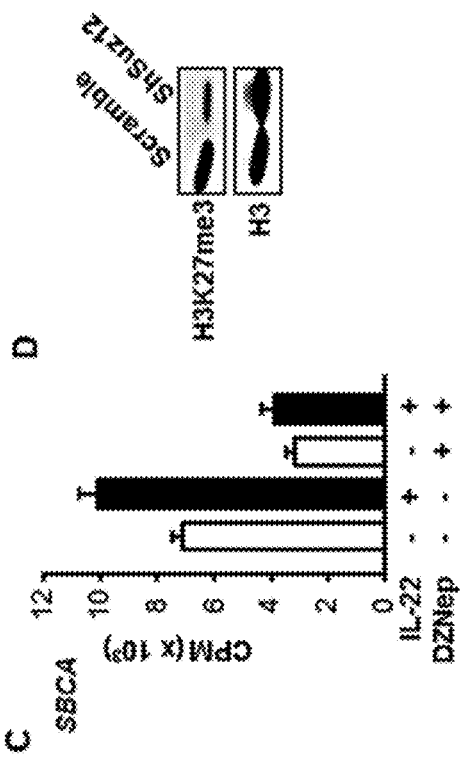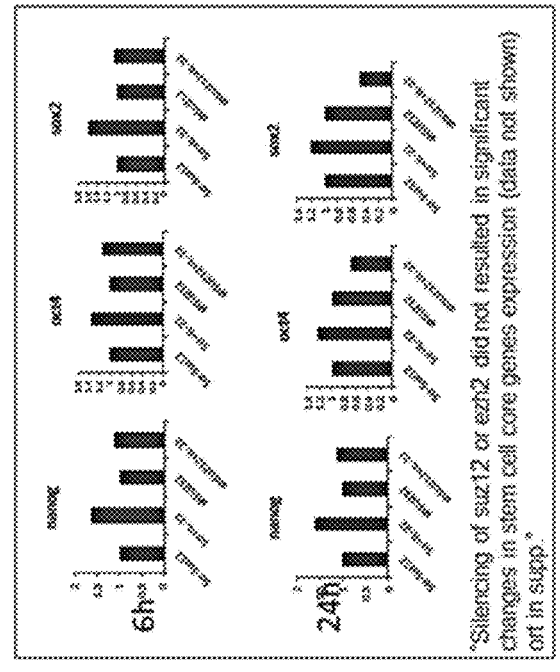
FIG. 21

A

EZH2

COMPOSITIONS AND METHODS FOR DETECTING AND TREATING COLORECTAL CANCER

CROSS-REFERENCE TO RELATED APPLICATIONS

The present application claims priority to U.S. Provisional Patent Application Ser. No. 61/931,891, filed Jan. 27, 2014, the disclosure of which is herein incorporated by reference in its entirety.

STATEMENT REGARDING FEDERALLY SPONSORED RESEARCH OR DEVELOPMENT

This invention was made with government support under CA099985, CA123088, CA156685, and CA171306 awarded by the National Institutes of Health. The government has certain rights in the invention.

FIELD OF THE INVENTION

The present invention relates to compositions and methods for the detecting, treating, and empirically investigating the interaction between a subject's immune system and cancer stem cells. In particular, the present invention provides compositions and methods for using IL-22 cytokine signaling and/or downstream targets of IL-22 cytokine signaling (e.g., STAT3, DOT1L, SUZ12, EED) in the diagnosis, treatment, and empirical investigation of cancers characterized with cancer stem cells activated through IL-22 cytokine signaling.

BACKGROUND OF THE INVENTION

Colorectal cancer generally is a cancer from uncontrolled cell growth in the colon or rectum (parts of the large intestine) or in the appendix. Genetic analyses shows that essentially colon and rectal tumors are genetically the same cancer (see, e.g., Cancer Genome Atlas Network (19 Jul. 2012) Nature 487 (7407)). Symptoms of colorectal cancer typically include rectal bleeding and anemia which are sometimes associated with weight loss and changes in bowel habits.

Diagnosis of colorectal cancer is via tumor biopsy typically done during colonoscopy or sigmoidoscopy, depending on the location of the lesion. The extent of the disease is then usually determined by a CT scan of the chest, abdomen and pelvis. There are other potential imaging test such as PET and MRI which may be used in certain cases. Colon cancer staging is done next and based on the TMN system which is determined by how much the initial tumor has spread, if and where lymph nodes are involved, and if and how many metastases there are (see, e.g., Cunningham D, et al. (2010) Lancet 375 (9719): 1030-47).

At least 50% of the Western population will develop a colorectal tumor by age 70 years. In 10% of these individuals, the tumor progresses to malignancy. In adults, colorectal cancer is the second leading cancer that causes death worldwide (see, e.g., Bi X, et al., (2006) Mol Cell Proteomics 5(6):1119-30).

As such, improved techniques for detecting, treating and understanding colorectal cancer are needed.

SUMMARY OF THE INVENTION

Experiments conducted during the course of developing embodiments for the present invention hypothesized that colon cancer infiltrating IL-22$^+$ cells contribute to cancer stem cell renewal and expansion, reshape the tumor invasive phenotype, and affect colon cancer patient outcomes. In such experiments, the interaction between IL-22$^+$ cells and cancer (stem) cells was investigated at the molecular, cellular and clinical level in patients with colon cancer. Indeed, IL-22 was shown to increase tumor sphere formation within a colorectal cancer model, and increase the expression of core cancer stem cell genes (NANOG, SOX2 and OCT3/4) and a human cancer stem cell marker (aldehyde dehydrogenase 1 (ALDH1)). IL-22 was shown to promote cancer stemness by STAT3 activation which directly targets and induces the expression of disruptor of telomeric 1 like (DOT1L), a histone 3 lysine 79 (H3K79) methyltransferase. IL-22 was shown to induce DOT1L expression in colon cancer cells and selectively increase H3K79 dimethylation (H3K79me2) at the promoter of core stem cell genes (SOX2, NANOG, OCT3/4). Thus, such experiments demonstrate that IL-22 signaling activates STAT3 which induces the expression of cancer stem cell genes by promoting a transcriptionally chromatin environment via DOT1L-mediated H3K79 methylation at gene promoters. Blocking DOT1L activity by using a chemical inhibitor and/or shRNA knockdown was shown to decrease IL-22 dependent colon cancer stemness and tumorigenic potential. Increased levels of DOT1lL and H3K79me2 correlated with poor survival among colon cancer patients. In addition, increased levels of tumor associated DOT1L and H3K79me2 were found to be independent predictors of poor survival among colon cancer patients. As such, the present invention contemplates the use of IL-22 and DOT1L as cancer stem cell (CSC) biomarkers and solid tumor prognostic markers, and as targets for immunotherapy to reduce the tumorigenic and metastatic potential of CSC in solid tumors.

Moreover, considering that both JAK-STAT signaling and Polycomb Repression complex (PRC) 2 play crucial roles in epithelial proliferation, the mechanism by which IL-22 induces colon cancer proliferation was investigated. Colon cancer cells proliferation was detected by FACS and H3 Thymidine Incorporation. Cell cycle related genes were tested by Real-Time PCR. Lentiviral vector encoding gene specific shRNAs (STAT3, EZH2, SUZ12) and scramble particles (Puromycin resistant) were used to transfect colon cancer cells. ChIP assays were performed to detect the binding of different protein and DNA. IL-22 was shown to significantly induce colon cancer cells proliferation through STAT3 signaling. This increased proliferation involved the inhibition of p16 and p18 through aberrant promoter histone methylation H3K27me3. PRC2 catalyzes promoter H3K27me3 of p16 and p18, which can be up-regulated by IL-22. Furthermore, STAT3 can bind to PRC2 members (SUZ12 and EED), which also can be up-regulated by IL-22 stimulation. It was concluded that IL-22 can induce human colon cancer cells proliferation by activation of STAT3, which was phosphorylated and directed bind to the PRC2 complex, especially SUZ12 and EED, and consequently catalyzed the H3K27m3 of cell cycle check-point genes p16 and p18.

Accordingly, the present invention relates to compositions and methods for the detecting, treating, and empirically investigating the interaction between a subject's immune system and cancer stem cells. In particular, the present invention provides compositions and methods for using IL-22 cytokine signaling and/or downstream targets of IL-22 cytokine signaling (e.g., STAT3, DOT1L, SUZ12, EED) in the diagnosis, treatment, and empirical investigation of cancers characterized with cancer stem cells activated through IL-22 cytokine signaling.

In certain embodiments, the present invention provides a collection of isolated biomarker proteins present in a biological sample comprising colorectal cancer cells obtained from a subject, wherein the biomarkers are indicative of activated cancer stem cells within the colorectal cancer cells, wherein the biomarkers are selected from the group consisting of IL-22, STAT3, DOT1L, SUZ12, and EED. In some embodiments, the biomarkers are affixed to a solid support. In some embodiments, the subject is a human subject.

In certain embodiments, the present invention provides a collection of isolated nucleic acids being affixed to a solid support, wherein the nuclaeic acids encode one or more human proteins isolatable from a biological sample comprising colorectal cancer cells obtained from a subject, wherein the human proteins are indicative of activated cancer stem cells within the colorectal cancer cells, wherein the one or more human proteins are selected from IL-22, STAT3, DOT1L, SUZ12, and EED. In some embodiments, the subject is a human subject.

In certain embodiments, the present invention provides a collection of isolated biomarker proteins isolatable from a biological sample comprising colorectal cancer cells obtained from a subject consisting of IL-22, STAT3, DOT1L, SUZ12, and EED which are indicative of activated cancer stem cells within the colorectal cancer, and a collection of antibodies immunologically specific for the biomarker proteins and reagents effective for assessing immune complex formation between the antibodies and the proteins. In some embodiments, the subject is a human subject.

In certain embodiments, the present invention provides methods of screening a subject to determine if the subject is at risk to develop, or is suffering from, colorectal cancer characterized with cancer stem cells activated through IL-22 signalling derived from IL-22 producing cells. In some embodiments, the methods comprise detecting a measurable feature of one or more biomarkers for detecting activated cancer stem cells within colorectal cancer cells isolated from a biological sample obtained from the subject, wherein the biological sample comprising colorectal cancer cells, wherein the biomarkers are selected from the group consisting of IL-22, STAT3, DOT1L, SUZ12, and EED, and comparing the measurable features of the one or more biomarkers from the biological sample to a reference standard, wherein a difference in the measurable features of the one or more biomarkers from the biological sample and the reference standard is indicative of the presence or risk of colorectal cancer characterized with cancer stem cells activated through IL-22 signalling derived from IL-22 producing cells in the subject. In some embodiments, the subject is a human subject.

In certain embodiments, the methods comprise a) obtaining a biological sample from a subject, wherein the biological sample comprises colorectal cancer cells; b) processing the sample; c) performing a binding assay comprising contacting the processed sample with an antibody to at least one of IL-22, STAT3, DOT1L, SUZ12, and EED to form a complex between the respective antibody and IL-22, STAT3, DOT1L, SUZ12, or EED in the processed sample; the binding assay generating at least one assay result indicative of the complex; and d) administering a treatment for inhibiting the activation of cancer stem cells within colorectal cancer cells when the amount of IL-22, STAT3, DOT1L, SUZ12, and/or EED in the sample is high compared to a normal control. In some embodiments, the treatment is administration of one or more agents selected from the group consisting of an IL-22 inhibiting agent, a STAT3 inhibiting agent, a DOT1L inhibiting agent, a SUZ12 inhibiting agent, and an EED inhibiting agent. In some embodiments, the IL-22 inhibiting agent is a pharmaceutical composition comprising ARGX112. In some embodiments, the IL-22 inhibiting agent is a pharmaceutical composition comprising Interleukin 22RA mAb. In some embodiments, the IL-22 inhibiting agent is a pharmaceutical composition comprising a IL-22 blocking antibody. In some embodiments, the DOT1L inhibiting agent is a pharmaceutical composition comprising EPZ5676. In some embodiments, the methods further comprise co-administering to the subject therapeutic amounts of one or more therapeutic agents known to treat cancer.

The method is not limited to a particular type or kind of therapeutic agent known to treat cancer, nor is it limited to the administration of a particular number of anti-cancer agents. In some embodiments, the -anti-cancer agent is select from at least one of the group consisting of Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin;

Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N'-Bis(2-chloroethyl)-N-nitrosourea (BCNU); N-(2-chloroethyl)-N'-cyclohex-yl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); 2-chlorodeoxyadenosine (2-Cda), Antiproliferative agents, Piritrexim Isothionate, Antiprostatic hypertrophy agents, Sitogluside, Benign prostatic hypertrophy therapy agents, Tamsulosin Hydrochloride, Prostate growth inhibitor agents, Pentomone, and Radioactive agents, Fibrinogen 1 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; and Triolein I 131.

In certain embodiments, the present invention provides methods for inhibiting cancer stem cell activation within colorectal cancer cells characterized with activated cancer stem cells, comprising exposing to a biological sample comprising colorectal cancer cells characterized with activated cancer stem cells a composition comprising one or more agents selected from the group consisting of an IL-22 inhibiting agent, a STAT3 inhibiting agent, a DOT1L inhibiting agent, a SUZ12 inhibiting agent, and a EED inhibiting agent. In some embodiments, the activated cancer stem cells were activated through IL-22 signalling derived from IL-22 producing cells within the colorectal cancer cells. In some embodiments, the composition inhibits IL-22 signaling within the colorectal cancer cells.

In certain embodiments, the present invention provides methods for treating a subject having colorectal cancer cells characterized with activated cancer stem cells, comprising administering to the subject a pharmaceutical composition comprising one or more agents selected from the group consisting of an IL-22 inhibiting agent, a STAT3 inhibiting agent, a DOT1L inhibiting agent, a SUZ12 inhibiting agent, and a EED inhibiting agent, wherein the activated cancer stem cells were activated through IL-22 signalling derived from IL-22 producing cells within the colorectal cancer cells, wherein the pharmaceutical composition inhibits IL-22 signalling within the colorectal cancer cells. In some embodiments, the subject is a human subject. In some embodiments, the IL-22 inhibiting agent is a pharmaceutical composition comprising ARGX112. In some embodiments, the IL-22 inhibiting agent is a pharmaceutical composition comprising Interleukin 22RA mAb. In some embodiments, the IL-22 inhibiting agent is a pharmaceutical composition comprising a IL-22 blocking antibody. In some embodiments, the DOT1L inhibiting agent is a pharmaceutical composition comprising EPZ5676.

In certain embodiments, the present invention provides compositions comprising an antibody specific for a colorectal cancer cell biomarker for detecting cancer stem cells activated through IL-22 signalling derived from IL-22 producing cells. In some embodiments, the biomarker is selected from IL-22, STAT3, DOT1L, SUZ12, and/or EED.

In certain embodiments, the present invention provides methods for detecting the presence of activated cancer stem cells within colorectal cancer cells, comprising providing reagents that detect one or more biomarkers for detecting activated cancer stem cells within colorectal cancer cells; obtaining a biological sample from a subject having colorectal cancer, wherein the biological sample comprises colorectal cancer cells; applying the reagents to the biological sample, wherein the presence of one or more biomarkers creates a complex between the reagent specific for the biomarker; detecting the presence or absence of a complex between one or more of the biomarkers and the reagents specific for the biomarkers, wherein a detected presence of a complex between one or more of the biomarkers and the reagents specific for the biomarkers indicates the presence of activated cancer stem cells within the colorectal cancer cells. In some embodiments, the activated cancer stem cells are activated through IL-22 signalling derived from IL-22 producing cells. In some embodiments, the biomarkers for detecting activated cancer stem cells within colorectal cancer cells are selected from IL-22, STAT3, DOT1L, SUZ12, and/or EED. In some embodiments, the activated cancer stem cells are self renewing cancer stem cells. In some embodiments, the activated cancer stem cells are expanding cancer stem cells. In some embodiments, the subject is a human subject. In some embodiments, the subject is a human subject diagnosed with colorectal cancer. In some embodiments, the reagents that detect one or more biomarkers for detecting activated cancer stem cells within colorectal cancer cells are selected from the group consisting of nucleic acids complementary with the biomarkers, nucleotides complementary with the biomarkers, oligonucleotides complementary with the biomarkers, polynucleotides complementary with the biomarkers, amino acids complementary with the biomarkers, peptides complementary with the biomarkers, polypeptides complementary with the biomarkers, proteins complementary with the biomarkers, and monoclonal and/or polyclonal antibodies complementary with the biomarkers.

The present invention also provides kits for assessing the presence of activated cancer stem cells (e.g., cancer stem cells activated through IL-22 signaling within colorectal cancer cells) within colorectal cancer cells in a subject, comprising: one or more reagents that specifically detects the presence or absence of expression of IL-22, STAT3, DOT1L, SUZ12, and/or EED; instructions for using the kit for assessing the presence of activated cancer stem cells (e.g., cancer stem cells activated through IL-22 signaling within colorectal cancer cells) within colorectal cancer cells in a subject. In some embodiments, the one or more reagents comprise an antibody that specifically binds to IL-22, STAT3, DOT1L, SUZ12, and/or EED. In still further embodiments, the antibody specifically binds to IL-22, STAT3, DOT1L, SUZ12, and/or EED protein with low background binding. In yet other embodiments, the antibody binds to human and mouse IL-22, STAT3, DOT1L, SUZ12, and/or EED. In some embodiments, the antibody is a monoclonal antibody. In some embodiments, the kit further comprises instructions. In some embodiments, the instructions comprise instructions required by the United States Food and Drug Administration for use in in vitro diagnostic products.

In certain embodiments, the present invention provides methods of treating colorectal cancer characterized with activated cancer stem cells in a subject, comprising administering to the subject one or more agents that down-regulate the expression, amount or activity of IL-22, STAT3, DOT1L, SUZ12, and/or EED, wherein the administering inhibits cancer stem cell activation within colorectal cancer cells. In some embodiments, the agent comprises a siRNA or shRNA that down-regulates IL-22 expression via RNA interference. In some embodiments, the agent comprises an siRNA or shRNA that down-regulates STAT3 expression via RNA interference (e.g., wherein the siRNA or shRNA comprises a sequence selected from sense oligonucleotide sequence 5'-ATTGCTGCAGGTCGTTGGT-3' (SEQ ID NO: 1) and sense oligonucleotide sequence 5'-TACCTAAGGCCATGAACTT-3' (SEQ ID NO: 2)). In some embodiments, the agent comprises a siRNA or shRNA that down-regulates DOT1L expression via RNA interference (e.g., wherein the siRNA or shRNA comprises the following sequence: sense oligonucleotide sequence 5'-AGTTGTT-GAGCTTCTCGGG-3' (SEQ ID NO: 3)). In some embodiments, the agent comprises a siRNA or shRNA that down-regulates SUZ12 expression via RNA interference. In some embodiments, the agent comprises a siRNA or shRNA that down-regulates EED expression via RNA interference. In some embodiments, the agent comprises an anti-IL-22, STAT3, DOT1L, SUZ12, and/or EED antibody or antigen-binding fragment thereof.

BRIEF DESCRIPTION OF THE DRAWINGS

FIG. 1A-M demonstrates IL-22 in the tumor environmental IL-22 promotes colon cancer stemness. (A), IL-22 is expressed in colon cancer tissues. IL-22 mRNA was detected by real-time PCR in colon cancer tissues and peripheral blood. *P<0.05 compared to blood, 20 colon cancer patients. (B-D), Endogenous IL-22 promotes colon carcinogenesis. Single cells ($10^7$) isolated from colon cancer tissue were mixed with anti-IL-22 antibody or control mAb, and then subcutaneously injected to NSG mice. Tumor growth (B), incidence (C), and animal survival (D) are shown. (P<0.05 for all, n=5 per group). (E-G) Recombinant IL-22 promotes colon carcinogenesis. DLD-1 colon cancer cells ($10^5$) were pre-incubated with IL-22 (20 ng/ml) for 1 hour, and then subcutaneously injected to NSG mice. Tumor growth (E), incidence (F), and animal survival (G) are shown. (P<0.05 for all, n=5 per group). (H, I) IL-22 enhances colon cancer sphere formation. DLD-1 colon cancer cells were pre-incubated for 24 hours with IL-22. Sphere assay was performed with 2,000 cells. Representative image of spheres (H) and the mean numbers of spheres (I) are shown. *P<0.05, n=5. (J) IL-22 increases ALDH1 activity in colon cancer cells. Colon cancer cell lines (DLD-1 and HT29) and two primary colon cancer cells (1, 2) were cultured with IL-22 for 24 hours. ALDH activity was determined by FACS based on aldefluor fluorescence. Cells treated with DEAB inhibitor were negative controls. Results are expressed as fold changes of ALDH expression. (P<0.05 for all, n=3 repeats per group). (K-M) IL-22 stimulates core stem cell gene expression in colon cancer cells. DLD-1 colon cancer cells were cultured with IL-22 (20 ng/ml). The mRNA of stem cell core gene was detected by real-time PCR (K) and proteins were detected by western blotting (L, M). (*P<0.05, n=5).

FIG. 8A-L demonstrates that IL-22 controls colon cancer sternness via DOT1L/H3K79me2. (A) IL-22 induces H3K79me2 in colon cancer cells. Colon cancer cells were treated with IL-22 for 48 hours. Total histone modifications were analyzed by western blot. (B, C) DOT1L inhibitor, EPZ004777 suppresses colon cancer sphere formation induced by IL-22. Colon cancer sphere assay was performed in the presence of IL-22 and EPZ004777. Sphere numbers were recorded. DLD-1 cells (B), primary colon cancer cells (C). (n=5, P<0.05). (D, E) IL-22 stimulates DOT1L complex gene expression. Colon cancer cells were cultured for 12 hours with IL-22. DOT1L complex gene expression was quantified by real-time PCR. DLD-1 cells (D), primary colon cancer cells (E). (n=3, P<0.05). (F) DOT1L knock down results in reduced colon cancer sphere formation induced by IL-22. Colon cancer sphere assay was performed with colon cancer cells expressing sh-DOT1L or vector in the presence of IL-22. Sphere numbers were recorded. (n=5, P<0.05). (G-I), IL-22 causes higher occupancy of H3K79me2 on core stem cell gene promoters. H3K79me2-ChIP assay was performed in DLD-1 colon cancer cells cultured with IL-22. One of 3 experiments is shown. (J-L), DOT1L inhibitor, EPZ004777 results in reduced occupancy of H3K79 on core stem cell gene promoters induced by IL-22. H3K79me2 ChIP was performed in DLD-1 colon cancer cells cultured with or without IL-22 and EPZ004777. One of three experiments is shown.

FIG. 17A-F demonstrates that IL-22 promotes colon cancer cell proliferation. A. GSEA analysis identifies proliferation pathways have positive correlation with IL-22. B. Cell proliferation maker Ki67 was detected by FACS. C. $H^3$ Thymidine Incorporation was used to detect the function of IL-22 in cell proliferation. D. Cell number was counted after stimulated with IL-22. E. Cells isolated from colon cancer tissue (Tumor cells and Leukocytes) were stimulated with a-CD3 and a-CD8 for 3 days, and supernatant mixed with or without anti-IL-22 antibody was co-cultured with DLD1 cells for 24 h to test cell proliferation. F. Cell cyclin-dependent kinase and kinase inhibitors were analyzed by Real-Time PCR.

FIG. 18A-M demonstrates the effect of IL-22 on cell proliferation is PRC2 dependent. A, C. Cell proliferation was analyzed using $H^3$ Thymidine Incorporation. B. The level of total H3K79m2 and H3K27me3 was measured by Western Blot. D. PcG proteins of EZH2, EED, SUZ12 was increased with IL-22(20 ng/ml) treatment. E. EZH2, SUZ12 and EED was detected by Western Blot after IL-22 treated for 24 h or 48 h. F. EZH2 inhibitor DZNep reduced cell proliferation. G.H. The efficiency of EZH2 and SUZ12 knock down was tested by Western Blot. I.J. Cell proliferation was analyzed using $H^3$ Thymidine Incorporation after knock down of EZH2 and SUZ12. K.L. Relative expression of cyclin-dependent kinase inhibitors (p16 and p18) in shEZH2, shSUZ12 and Dznep treated cells after IL-22 treatment. M. The level of H3K27me3 in the promoter of p16 and p18 was analyzed by ChIP assay.

FIG. 21A-E A. Dot1L/H3K79me2 inhibitor EZP004777 (10 uM) had no effect on SUZ12 expression but reduce Sox2. B. EZP004777 had no effect on primary colon cancer cell line SBCA. C. EZH2 inhibitor DZNep reduced SBCA cell proliferation. D. SUZ12 knockdown reduced H3K27m3 level. E. Effect of I1-22 on tumor sphere assay was analyzed in shEZH2, shSUZ12 and Dznep treated cells.

DEFINITIONS

Figure 2:
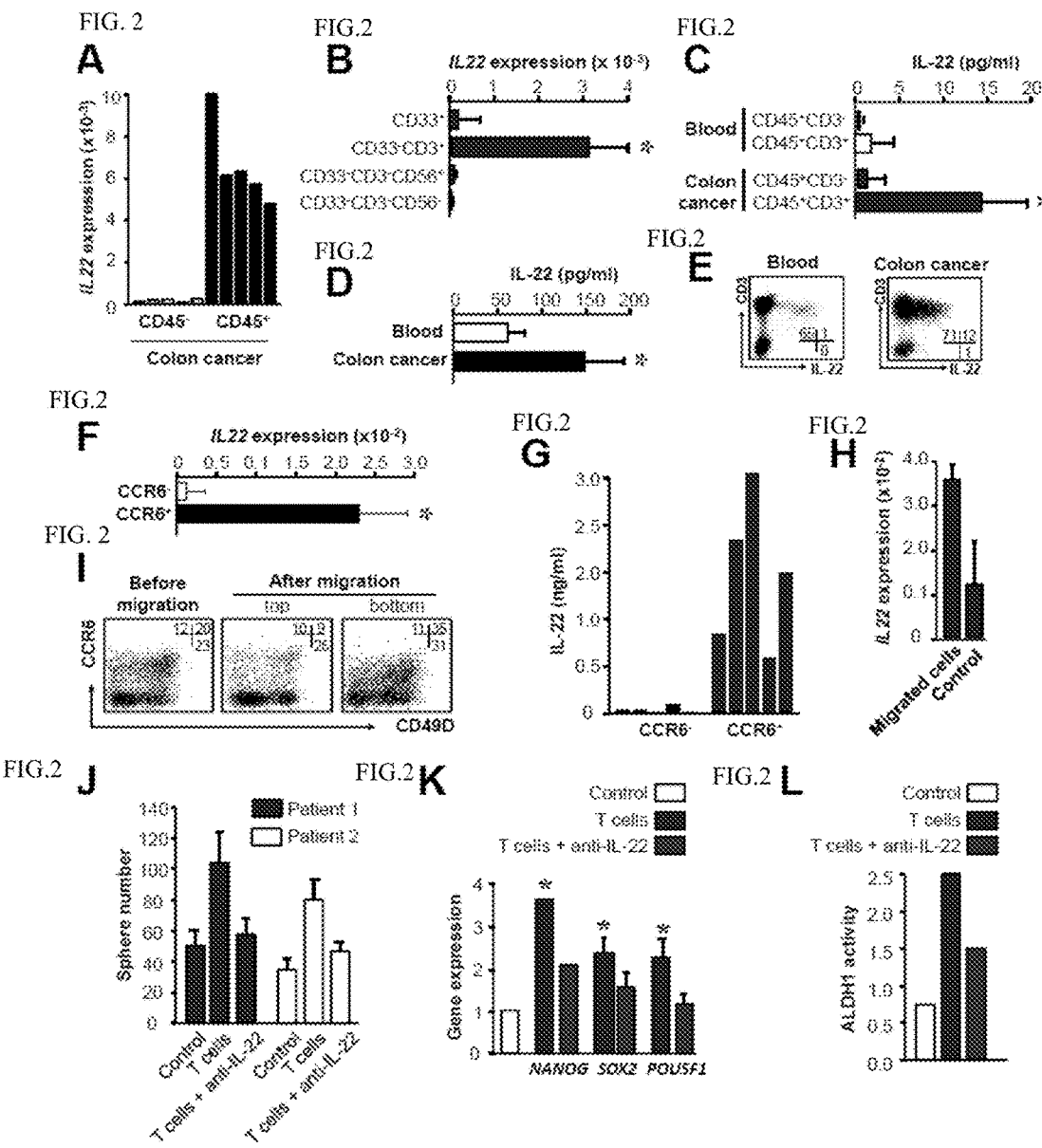
FIG. 2A-L demonstrates that Th22 cells traffic into the tumor and promote cancer stemenss via IL-22. (A, B) IL-22 is expressed by immune cells in colon cancer tissues. Different cell populations were sorted from colon cancer tissues and IL-22 expression was measured by real time PCR. (5-10 donors, P<0.05). (C) IL-22 is spontaneously released by different immune cell populations in colon cancer tissues. Different CD45$^+$ immune subsets ($10^6$/ml) were sorted from colon cancer and blood, and cultured for 12 hours. IL-22 was detected via ELISA. (n=5, *P<0.05). (D, E) IL-22 is expressed by activated CD4$^+$ T cells in colon cancer tissues. CD45$^+$ subsets ($10^6$/ml) were sorted from colon cancer and blood, and were activated with anti-CD3 and anti-CD28 for 2 days. IL-22 was detected with ELISA (D) or intracellular staining (E). (n=5, *P<0.05). (F, G) CCR6$^+$CD4$^+$ T cells express IL-22. CD4$^+$ T cells were sorted based on CCR6 expression and activated with anti-CD3 and anti-CD28 and antigen presenting cells. IL-22 mRNA was detected by real time PCR (F) and protein by ELISA (G). (5 different donors, P<0.05). (H, I) Th22 cells migrate toward CCL20. Migration assay was conducted with CD4$^+$ T cells for 4 hours in the presence of CCL-20. IL-22 expression was quantified with real-time PCR in the migrated and non-migrated cells. Results are expressed as the mean relative expression (H). The phenotype of migrated cells, non-migrated cells and control (before migration) was analyzed by FACS (I). (n=3, P<0.05). (J) Th22 cells enhance colon cancer sphere formation. Sphere assay was performed with autologous colon tumor cells in the presence of activated colon cancer-associated T cells in a transwell system. Anti-IL-22 or isotype mAbs were added in the assay. Results are shown as the mean numbers of spheres in triplicates. (2 of 5 patients are shown. P<0.01). (K, L) Th22 cells stimulates colon cancer sternness. Primary colon cancer associated T cells were sorted and activated for 3 days. DLD-1 colon cancer cells were cultured with these T cell supernatants in the presence of anti-IL-22 or isotype mAbs. The mRNA of stem cell core genes was detected by real-time PCR after 6 hours (K) and ALDH activity was detected by FACS after 48 hours (L). (n=5, *P<0.05).

Following long-standing patent law convention, the terms "a", "an", and "the" refer to "one or more" when used in this application, including the claims. Thus, for example, reference to "a cell" or "a sample" includes a plurality of such cells or samples, respectively, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached exemplary claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" as used herein includes all members of the animal kingdom including mammals, and suitably refers to humans. Optionally, the term "subject" includes mammals that have been diagnosed with a colorectal cancer or are in remission.

As used herein the term "cancer stem cell" refers to a cell that is capable of self-renewal and differentiating into the lineages of cancer cells that comprise a tumor or hematological malignancy. Cancer stem cells are uniquely able to initiate and sustain the disease. Without being bound by theory, a cancer stem cell can have a variety of cellular properties. For instance, a cancer stem cell can re-grow a tumor. Cancer stem cells can divide asymmetrically and symmetrically and can show variable rates of proliferation. Additionally, a cancer stem cell can grow in vitro under established cancer stem cell conditions such as in a serum-free medium and/or in suspension or on low-attachment plates. "Activated cancer stem cells" refers generally to cancer stem cells that are actively self-renewing and/or actively expanding.

As used herein "biomarker associated with cancer stem cells" refers to a biomarker such as a nucleic acid, polypeptide or fragment thereof, whose expression, or lack thereof, by a cell is indicative of the cell being a cancer stem cell.

The term "biomolecule" refers to a molecule that is produced by a cell or tissue in an organism. Such molecules include, but are not limited to, molecules comprising nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, and combinations thereof (e.g., glycoproteins, ribonucleoproteins, lipoproteins). Furthermore, the terms "nucleotide", "oligonucleotide" or polynucleotide" refer to DNA or RNA of genomic or synthetic origin which may be single-stranded or double-stranded and may represent the sense or the antisense strand. Included as part of the definition of "oligonucleotide" or "polynucleotide" are peptide polynucleotide sequences (e.g., peptide nucleic acids; PNAs), or any DNA-like or RNA-like material (e.g., morpholinos, ribozymes).

The term "molecular entity" refers to any defined inorganic or organic molecule that is either naturally occurring or is produced synthetically. Such molecules include, but are not limited to, biomolecules as described above, simple and complex molecules, acids and alkalis, alcohols, aldehydes, arenas, amides, amines, esters, ethers, ketones, metals, salts, and derivatives of any of the aforementioned molecules.

The term "fragment" refers to a portion of a polynucleotide or polypeptide sequence that comprises at least a series (e.g., about 10, 15, 20, 30, etc.) consecutive nucleotides or 5 consecutive amino acid residues, respectively.

The terms "biological sample" and "test sample" refer to all biological fluids and excretions isolated from any given subject (e.g., a human patient diagnosed with colorectal cancer). In the context of the invention such samples include, but are not limited to, blood, serum, plasma, urine, semen, seminal fluid, seminal plasma, pre-ejaculatory fluid (Cowper's fluid), nipple aspirate, vaginal fluid, excreta, tears, saliva, sweat, biopsy, ascites, cerebrospinal fluid, lymph, marrow, hair or tissue extract samples.

The term "specific binding" refers to the interaction between two biomolecules that occurs under specific conditions. The binding of two biomolecules is considered to be specific when the interaction between said molecules is substantial. Moreover, the phrase "specific conditions" refers to reaction conditions that permit, enable, or facilitate the binding of said molecules such as pH, salt, detergent and other conditions known to those skilled in the art.

The term "interaction" relates to the direct or indirect binding or alteration of biological activity of a biomolecule.

The term "colorectal cancer" refers to a malignant neoplasm of the large intestine/colon within a given subject, wherein the neoplasm is of epithelial origin and is also referred to as a carcinoma of the large intestine/colon. According to the invention, colorectal cancer is defined according to its type, stage and/or grade. Typical staging systems known to those skilled in the art such as the Gleason Score (a measure of tumor aggressiveness based on pathological examination of tissue biopsy), the Jewett-Whitmore system and the TNM system (the system adopted by the American Joint Committee on Cancer and the International Union Against Cancer). The term "colorectal cancer", when used without qualification, includes both localized and metastasised colorectal cancer. The term "colorectal cancer" can be qualified by the terms "localized" or "metastasised" to differentiate between different types of tumor as those words are defined herein. The terms "colorectal cancer" and "malignant disease of the large intestine/colon" are used interchangeably herein. The term "colorectal cancer" includes, but is not limited to, colon cancer, rectal cancer, and bowel cancer.

The terms "neoplasm" or "tumor" may be used interchangeably and refer to an abnormal mass of tissue wherein growth of the mass surpasses and is not coordinated with the growth of normal tissue. A neoplasm or tumor may be defined as "benign" or "malignant" depending on the following characteristics: degree of cellular differentiation including morphology and functionality, rate of growth, local invasion and metastasis. A "benign" neoplasm is generally well differentiated, has characteristically slower growth than a malignant neoplasm and remains localized to the site of origin. In addition a benign neoplasm does not have the capacity to infiltrate, invade or metastasize to distant sites. A "malignant" neoplasm is generally poorly differentiated (anaplasia), has characteristically rapid growth accompanied by progressive infiltration, invasion and destruction of the surrounding tissue. Furthermore, a malignant neoplasm has to capacity to metastasize to distant sites.

The term "metastasis" refers to the spread or migration of cancerous cells from a primary (original) tumor to another organ or tissue, and is typically identifiable by the presence of a "secondary tumor" or "secondary cell mass" of the tissue type of the primary (original) tumor and not of that of the organ or tissue in which the secondary (metastatic) tumor is located. For example, a colorectal cancer that has migrated to bone is said to be metastasised colorectal cancer, and consists of cancerous colorectal cancer cells in the large intestine/colon as well as cancerous colorectal cancer cells growing in bone tissue.

The phrase "neoplastic transformation of a cell" refers an alteration in normal cell physiology and includes, but is not limited to, self-sufficiency in growth signals, insensitivity to growth-inhibitory (anti-growth) signals, evasion of programmed cell death (apoptosis), limitless replicative potential, sustained angiogenesis, and tissue invasion and metastasis.

The term "differentially present" refers to differences in the quantity of a biomolecule present in samples taken from colorectal cancer patients as compared to samples taken from subjects having a non-malignant disease of the large intestine/colon or healthy subjects. Furthermore, a biomolecule is differentially present between two samples if the quantity of said biomolecule in one sample population is significantly different (defined statistically) from the quantity of said biomolecule in another sample population. For example, a given biomolecule may be present at elevated, decreased, or absent levels in samples of taken from subjects having colorectal cancer compared to those taken from subjects who do not have a colorectal cancer.

The term 'biological activity' may be used interchangeably with the terms 'biologically active', 'bioactivity' or 'activity' and, for the purposes herein, means an effector or antigenic function that is directly or indirectly performed by a biomarker of the invention (whether in its native or denatured conformation), derivative or fragment thereof. Effector functions include phosphorylation (kinase activity) or activation of other molecules, induction of differentiation, mitogenic or growth promoting activity, signal transduction, immune modulation, DNA regulatory functions and the like, whether presently known or inherent. Antigenic functions include possession of an epitope or antigenic site that is capable of cross-reacting with antibodies raised against a naturally occurring or denatured biomarker of the invention, derivative or fragment thereof. Accordingly, a biological activity of such a protein can be that it functions as regulator of a signaling pathway of a target cell. Such a signaling pathway can, for example, modulate cell differentiation, proliferation and/or migration of such a cell, as well as tissue invasion, tumor development and/or metastasis. A target cell according to the invention can be a neoplastic or cancer cell.

The terms 'neoplastic cell' and 'neoplastic tissue' refer to a cell or tissue, respectively, that has undergone significant cellular changes (transformation). Such cellular changes are manifested by an escape from specific control mechanisms, increased growth potential, alteration in the cell surface, karyotypic abnormalities, morphological and biochemical deviations from the norm, and other attributes conferring the ability to invade, metastasize and kill.

The term "diagnostic assay" can be used interchangeably with "diagnostic method" and refers to the detection of the presence or nature of a pathologic condition.

The term "adsorbent" refers to any material that is capable of accumulating (binding) a given biomolecule. The adsorbent typically coats a biologically active surface and is composed of a single material or a plurality of different materials that are capable of binding a biomolecule. Such materials include, but are not limited to, anion exchange materials, cation exchange materials, metal chelators, polynucleotides, oligonucleotides, peptides, antibodies, naturally occurring compounds, synthetic compounds, etc.

The phrase "biologically active surface" refers to any two- or three-dimensional extensions of a material that biomolecules can bind to, or interact with, due to the specific biochemical properties of this material and those of the biomolecules. Such biochemical properties include, but are not limited to, ionic character (charge), hydrophobicity, or hydrophilicity.

The term "binding biomolecule" refers to a molecule that displays an affinity for another biomolecule.

The term "immunogen" may be used interchangeably with the phrase "immunizing agent" and refers to any substance or organism that provokes an immune response when introduced into the body of a given subject. All immunogens are considered as antigens and, in the context of the invention, can be defined on the basis of their immunogenicity, wherein "immunogenicity" refers to the ability of the immunogen to induce either a humoral or a cell-mediated immune response. In the context of the invention an immunogen that induces a "humoral immune response" activates antibody production and secretion by cells of the B-lymphocyte lineage (B-cells) and thus can be used to for antibody production as described herein. Such immunogens may be polysaccharides, proteins, lipids or nucleic acids, or they may be lipids or nucleic acids that are complexed to either a polysaccharide or a protein. The term "solution" refers to a homogeneous mixture of two or more substances. Solutions may include, but are not limited to buffers, substrate solutions, elution solutions, wash solutions, detection solutions, standardization solutions, chemical solutions, solvents, etc.

The phrase "coupling buffer" refers to a solution that is used to promote covalent binding of biomolecules to a biological surface.

The phrase "blocking buffer" refers to a solution that is used to (prevent) block unbound binding sites of a given biological surface from interacting with biomolecules in an unspecific manner.

The term "chromatography" refers to any method of separating biomolecules within a given sample such that the original native state of a given biomolecule is retained. Separation of a biomolecule from other biomolecules within a given sample for the purpose of enrichment, purification and/or analysis, may be achieved by methods including, but not limited to, size exclusion chromatography, ion exchange chromatography, hydrophobic and hydrophilic interaction chromatography, metal affinity chromatography, wherein "metal" refers to metal ions (e.g. nickel, copper, gallium, zinc, iron or cobalt) of all chemically possible valences, or ligand affinity chromatography wherein "ligand" refers to binding molecules, preferably proteins, antibodies, or DNA. Generally, chromatography uses biologically active surfaces as adsorbents to selectively accumulate certain biomolecules.

The phrase "mass spectrometry" refers to a method comprising employing an ionization source to generate gas phase ions from a biological entity of a sample presented on a biologically active surface, and detecting the gas phase ions with an ion detector. Comparison of the time the gas phase ions take to reach the ion detector from the moment of ionization with a calibration equation derived from at least one molecule of known mass allows the calculation of the estimated mass to charge ratio of the ion being detected.

The phrases "mass to charge ratio", "m/z ratio" or "m/z" can be used interchangeably and refer to the ratio of the molecular weight (grams per mole) of an ion detected by mass spectrometry to the number of charges the ion carries. Thus a single biomolecule can be assigned more than one mass to charge ratio by a mass spectrometer if that biomolecule can be ionized into more than one species each of which carries a different number of charges.

The acronym "TOF" refers to the time-of-flight of a biomolecule or other molecular entity, and particularly that of an ion in a time-of-flight type mass spectrometer. TOF values are derived by measuring the duration of flight of an ion, typically between its entry into and exit from a time-of-flight analyzer tube. Alternatively, the accuracy of TOF values can be improved by methods known to those skilled in the art, for example through the use of reflectrons and/or pulsed-laser ionization. TOF values for a given ion can be applied to previously established calibration equations derived from the TOF values for ions of known mass in order to calculate the mass to charge ratio of these ions.

The phrase "laser desorption mass spectrometry" refers to a method comprising the use of a laser as an ionization source to generate gas phase ions from a biomolecule presented on a biologically active surface, and detecting the gas phase ions with a mass spectrometer.

The term "mass spectrometer" refers to a gas phase ion spectrometer that includes an inlet system, an ionization source, an ion optic assembly, a mass analyzer, and a detector.

Within the context of the invention, the terms "detect", "detection" or "detecting" refer to the identification of the presence, absence, or quantity of a given biomolecule.

The term "antibody immunoassay" refers to any analytical test that can generate a signal from an analyte present in a biological liquid, typically serum or urine, by using antibodies complementary to the antigens present on the analyte. Antibodies are very selective and only bind to their specific target, even in the presence of a multitude of alternative proteins or materials in a sample. Generally, an antibody immobilized onto a surface, usually a microtiter plate, captures the teat analyte from the sample and a different antibody, specific for another part of the analyte, binds and acts as the detector molecule. The signal output by the detector antibody is proportional to the amount of analyte in the sample; the concentration of analyte can be quantified by comparing signal outputs to those of known standard concentrations.

The term "antibody" is used in the broadest sense and specifically includes monoclonal antibodies (including full length monoclonal antibodies), multispecific antibodies (e.g., bispecific antibodies), and antibody fragments that exhibit a desired biological activity or function. Antibodies can be chimeric, humanized, or mammalian, including mouse or human. Antibodies can also be an antibody fragment.

"Antibody fragments" comprise a portion of a full length antibody, generally the antigen binding or variable region thereof. Examples of antibody fragments include Fab, Fab', $F(ab)_2$, and Fv fragments; diabodies; linear antibodies; single-chain antibody molecules; and multispecific antibodies formed from antibody fragments. "Functional fragments" substantially retain binding to an antigen of the full length antibody, and retain a biological activity.

DETAILED DESCRIPTION OF THE INVENTION

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991).

IL-22(interleukin-22) is a newly identified cytokine which shares 22% homology with IL-10 (see, e.g., Dumoutier, L., et al., (2000) Journal of immunology 164, 1814-1819). The expression oft L-22 is restricted to immune cells, mainly produced by Innate Lymphoid cells (called"ILC-22") and Th22 cells (CD4+IL-22+) (see, e.g., Lee, J. S., et al., (2012) Nat Immunol 13, 144-151; Spits, H., and Di Santo, J. P. (2011) Nat Immunol 12, 21-27; Basu, R., et al., (2012) Immunity 37, 1061-1075; Honda, K. (2012) Immunity 37, 952-954). IL-22 is critical in protecting epithelial mucosal from bacterial infection and inflammation damage in mouse models (see, e.g., Aujla, S. J., et al., (2008) Nat Med 14, 275-281; Zheng, Y., et al., (2008) Nature medicine 14, 282-289; Pickert, G., et al., (2009) J Exp Med 206, 1465-1472), since its receptor is only expressed on epithelial cells (see, e.g., Wolk, K., et al., (2004) Immunity 21, 241-254), which makes it an attractive target with fewer side effects. IL-22 drives proliferation in hepatocytes, colonic and airway epithelium by inducing pro-survival and cell cycle-related molecules (see, e.g., Cella, M., et al., (2009) Nature 457, 722-725; Jiang, R., et al., (2011) Hepatology 54, 900-909; Kirchberger, S., et al., (2013) The Journal of experimental medicine 210, 917-931).

The interaction between tumor cells and the immune system results in immunoediting of the tumor which molds the cancer into either a dormant state (see, e.g., Dunn, G. P. et al. (2002) Nat Immunol 3, 991-998; Matsushita, H. et al. (2012) Nature 482, 400-404), or fosters tumor immune evasion (see, e.g., Pardoll, D. M. (2012) Nat Rev Cancer 12, 252-264; Zou, W. (2005) Nat Rev Cancer 5, 263-274). The roles of tumor infiltrating $CD8^+$ T cells and regulatory T cells (see, e.g., Curiel, T. J. et al. (2004) Nat Med 10, 942-949; Galon, J. et al. (2006) Science 313, 1960-1964) have been extensively studied in human cancers. Although $IL-22^+CD4^+$ (Th22) cells (see, e.g., Duhen, T. et al. (2009) Nat Immunol 10, 857-863; Trifari, S., et al. (2009) Nat Immunol 10, 864-871) and IL-22 expressing innate leukocytes (ILC22) (see, e.g., Cella, M. et al. (2009) Nature 457, 722-725) are identified in humans (see, e.g., Spits, H., and Cupedo, T. (2012) Annu Rev Immunol 30, 647-675), the role of $IL-22^+$ immune cells is poorly defined in the human cancer microenvironment.

IL-22 producing immune cells could have a role in molding cancer, particularly colon cancer. The cytokine IL-22 has been shown to protect intestinal epithelial cells from bacterial infection and inflammation damage in mice (see, e.g., Aujla, S. J., et al. (2008) Nat Med 14, 275-281; Basu, R. et al. (2012) Immunity 37, 1061-1075; Hanash, A. M. et al. (2012) Immunity 37, 339-350; Pickert, G., et al. (2009) J Exp Med 206, 1465-1472; Sonnenberg, G. F., et al. (2012) Science 336, 1321-1325; Sonnenberg, G. F., et al. (2010) J Exp Med 207, 1293-1305; Zheng, Y. et al. (2008) Nat Med 14, 282-289) and supports thymic repair (see, e.g., Dudakov, J. A. et al. (2012) Science 336, 91-95). Recent mouse studies have revealed that $IL-22^+$ cells stimulate tumor cell proliferation in a bacteria-induced colon cancer model (see, e.g., Kirchberger, S. et al. (2013) J Exp Med. 6; 210(5):917-31) and IL-22 binding protein (IL-22BP) reduces chemical carcinogen-induced colon cancer development (see, e.g., Huber, S. et al. (2012) Nature 491, 259-263). Interestingly, IL-22 polymorphisms may be associated with an increased risk of colon carcinoma development (see, e.g., Thompson, C. L., et al. (2010) Cancer Causes Control 21, 1165-1170). This data suggests a potential link between $IL-22^+$ cells and colorectal cancer development and progression in humans. However, the nature and clinical relevance of $IL-22^+$ cells is poorly defined in patients with colorectal cancer. It is not known if and how $IL-22^+$ cells impact human colon cancer.

It has been demonstrated that cancer-initiating cells or cancer stem cells play an important role in shaping the invasive cancer phenotype by contributing to tumor initiation, metastasis/relapse, and therapeutic resistance (see, e.g., Brabletz, T., J et al. (2005) Nat Rev Cancer 5, 744-749; Dean, M. et al. (2005) Nat Rev Cancer 5, 275-284; Pardal, R., et al. (2003) Nat Rev Cancer 3, 895-902; Reya, T., et al. (2001) Nature 414, 105-111; Vermeulen, L., et al. (2012) Lancet Oncol 13, e83-89). A key issue in cancer stem cell biology is understanding the mechanisms by which cancer cells control self-renewal and expansion. Recent evidence points to a level of external control from the microenvironment that defines the stem cell niche (see, e.g., Zou, W., et al. (1997) J Virol 71, 1227-1236; Bendall, S. C., et al. (2007) Nature 448, 1015-1021; Scadden, D. T. (2006) Nature 441, 1075-1079).

Experiments conducted during the course of developing embodiments for the present invention hypothesized that colon cancer infiltrating $IL-22^+$ cells contribute to cancer stem cell renewal and expansion, reshape the tumor invasive phenotype, and affect colon cancer patient outcomes. In such experiments, the interaction between $IL-22^+$ cells and cancer (stem) cells was investigated at the molecular, cellular and clinical level in patients with colon cancer. Indeed, IL-22 was shown to increase tumor sphere formation within a colorectal cancer model, and increase the expression of core cancer stem cell genes (NANOG, SOX2 and OCT3/4) and a human cancer stem cell marker (aldehyde dehydrogenase 1 (ALDH1)). IL-22 was shown to promote cancer stemness by STAT3 activation which directly targets and induces the expression of disruptor of telomeric 1 like (DOT1L), a histone 3 lysine 79 (H3K79) methyltransferase. IL-22 was shown to induce DOT1L expression in colon cancer cells and selectively increase H3K79 dimethylation (H3K79me2) at the promoter of core stem cell genes (SOX2, NANOG, OCT3/4). Thus, such experiments demonstrate that IL-22 signaling activates STAT3 which induces the expression of cancer stem cell genes by promoting a transcriptionally chromatin environment via DOT1L-mediated H3K79 methylation at gene promoters. Blocking DOT1L activity by using a chemical inhibitor and/or shRNA knockdown was shown to decrease IL-22 dependent colon cancer stemness and tumorigenic potential. Increased levels of DOT1L and H3K79me2 correlated with poor survival among colon cancer patients. In addition, increased levels of tumor associated DOT1L and H3K79me2 were found to be independent predictors of poor survival among colon cancer patients. As such, the present invention contemplates the use of IL-22 and DOT1L as cancer stem cell (CSC) biomarkers and solid tumor prognostic markers, and as targets for immunotherapy to reduce the tumorigenic and metastatic potential of CSC in solid tumors.

Moreover, considering that both JAK-STAT signaling and Polycomb Repression complex (PRC) 2 play crucial roles in epithelial proliferation, the mechanism by which IL-22 induces colon cancer proliferation was investigated. Colon cancer cells proliferation was detected by FACS and H3 Thymidine Incorporation. Cell cycle related genes were tested by Real-Time PCR. Lentiviral vector encoding gene specific shRNAs (STAT3, EZH2, SUZ12) and scramble particles (Puromycin resistant) were used to transfect colon cancer cells. ChIP assays were performed to detect the binding of different protein and DNA. IL-22 was shown to significantly induce colon cancer cells proliferation through STAT3 signaling. This increased proliferation involved the inhibition of p16 and p18 through aberrant promoter histone methylation H3K27me3. PRC2 catalyzes promoter H3K27me3 of p16 and p18, which can be up-regulated by IL-22. Furthermore, STAT3 can bind to PRC2 members (SUZ12 and EED), which also can be up-regulated by IL-22 stimulation. It was concluded that IL-22 can induce human colon cancer cells proliferation by activation of STAT3, which was phosphorylated and directed bind to the PRC2 complex, especially SUZ12 and EED, and consequently catalyzed the H3K27m3 of cell cycle check-point genes p16 and p18.

Accordingly, the present invention relates to compositions and methods for the detecting, treating, and empirically investigating the interaction between a subject's immune system and cancer stem cells. In particular, the present invention provides compositions and methods for using IL-22 cytokine signaling and/or downstream targets of IL-22 cytokine signaling (e.g., STAT3, DOT1L, SUZ12, EED) in the diagnosis, treatment, and empirical investigation of cancers characterized with cancer stem cells activated through IL-22 cytokine signaling.

The embodiments of the present invention are not limited to particular types of cancer. In some embodiments, the cancers include, but are not limited to, colorectal cancer (e.g., any cancer or cancerous lesion associated with tissue or cells of colonic or rectal origin and can include precursors to colorectal cancer, for example, adenomatous colonic polyps or inflammatory bowel disease) (e.g., colon cancer, rectal cancer, bowel cancer).

The embodiments of the present invention are not limited to a particular manner of cancer stem cell activation. In some embodiments, cancer stem cell activation includes, but is not limited to, cancer stem cell self-renewal, and/or cancer stem cell expansion.

The embodiments of the present invention are not limited to a particular type of cell that produces IL-22 signalling. In some embodiments, the IL-22 signalling is derived from Th22 cells.

In certain embodiments, detecting the interaction between a subject's immune system and cancer stem cells involves quantifying and/or detecting the presence of cancer stem cells activated through IL-22 signalling derived from IL-22 producing cells. In some embodiments, such quantifying and/or detecting is accomplished through quantifying and/or detecting IL-22 signaling and/or quantifying and/or detecting downstream targets of IL-22 signaling (e.g., STAT3 expression and/or activity, DOT1L expression and/or activity, SUZ12 expression and/or activity, EED expression and/or activity) within cancer cells (e.g., tumor cells) (e.g., colorectal cancer tumor cells).

As noted, experiments conducted during the course of developing embodiments determined that increased levels of DOT1lL and H3K79 within cancer cells correlated with poor survival among colon cancer patients. In addition, such experiments demonstrated that increased levels of tumor associated DOT1L and H3K79me2 were found to be independent predictors of poor survival among colon cancer patients. Moreover, experiments demonstrated that increased levels of tumor associated SUZ12, EED and H3K27me3 were found to be independent predictors of poor survival among colon cancer patients. Accordingly, the present invention contemplates the use of IL-22, STAT3, DOT1L, SUZ12, and/or EED as CSC biomarkers and solid tumor prognostic markers.

In certain embodiments, the present invention provides methods for monitoring the progression of and/or prognosing a diagnosed colorectal cancer in a subject comprising detecting the presence of cancer stem cells activated through IL-22 signalling derived from IL-22 producing cells in a sample comprising colorectal cancer cells (e.g., tumor cells). In some embodiments, the detected presence of such activated cancer stem cells indicates a poor prognosis. In some embodiments, an increase in the amount of such activated cancer stem cells over multiple time points indicates a poor prognosis. In some embodiments, a decrease in the amount of such activated cancer stem cells over multiple time points indicates an improving prognosis. In some embodiments, the prognosis is provided through comparing the detection results of control subjects having activated cancer stem cells and various stages of a particular cancer. In such embodiments, the comparison allows for characterizing the severity of the cancer and its likely outcome.

The present invention is not limited to a particular manner of detecting the presence of cancer stem cells activated through IL-22 signaling within colorectal cancer cell (e.g., tumor cells). In some embodiments, the presence of such activated cancer stem cells within colorectal cancer cells (e.g., tumor cells) is accomplished through detecting the presence of IL-22 signaling and/or downstream targets of IL-22 signaling (e.g., STAT3 expression and/or activity, DOT1L expression and/or activity, SUZ12 expression and/or activity, EED expression and/or activity) within such colorectal cancer cells (e.g., tumor cells).

In some embodiments, detecting the presence of IL-22 signaling and/or downstream targets of IL-22 signaling (e.g., STAT3 expression and/or activity, DOT1L expression and/or activity, SUZ12 expression and/or activity, EED expression and/or activity) within such colorectal cancer cells (e.g., tumor cells) is accomplished through administering reagents specific for IL-22, STAT3, DOT1L, SUZ12, and/or EED to a sample comprising cancer cells obtained from a subject under conditions conducive for binding. In such embodiments, detection of a complex between IL-22, STAT3, DOT1L, SUZ12, and/or EED and such a reagent specific for IL-22, STAT3, DOT1L, SUZ12, and/or EED indicates the presence of cancer stem cells activated through IL-22 signaling within such colorectal cancer cells. Such methods are not limited to particular reagents specific for IL-22, STAT3, DOT1L, SUZ12, and/or EED. In some embodiments, the reagents include any type of reagent specific for IL-22, STAT3, DOT1L, SUZ12, and/or EED (e.g., nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, or combinations thereof (e.g. glycoproteins, ribonucleoproteins, lipoproteins), compounds or synthetic molecules).

In some embodiments, detecting the presence of IL-22 signaling and/or downstream targets of IL-22 signaling (e.g., STAT3 expression and/or activity, DOT1L expression and/or activity, SUZ12 expression and/or activity, EED expression and/or activity) within such colorectal cancer cells (e.g., tumor cells) is accomplished through contacting a biological sample comprising colorectal cancer cells with an adsorbent present on a biologically active surface under specific binding conditions, allowing IL-22, STAT3, DOT1L, SUZ12, and/or EED (if present) within the biological sample to bind to the adsorbent, detecting one or more bound IL-22, STAT3, DOT1L, SUZ12, and/or EED with a detection method, wherein the detection method generates a profile of said sample, transforming the profile generated into a computer-readable form, and comparing the profile of said sample with a database containing profiles from comparable samples specific for subjects having different stages of colorectal cancer and varying amounts of cancer stem cells activated through IL-22 signaling. The outcome of said comparison will allow for the determination of whether the subject from which the biological sample was obtained has a poor prognosis based on the presence, absence or comparative quantity of IL-22, STAT3, DOT1L, SUZ12, and/or EED. The level of the IL-22, STAT3, DOT1L, SUZ12, and/or EED can be compared in time in the same subject (e.g., human patient) to measure progression of disease or impact of treatment of the disease in that subject over time.

In some embodiments, a detected presence of IL-22, STAT3, DOT1L, SUZ12, and/or EED within colorectal cancer cells (i.e., thereby indicating the presence of cancer stem cells activated through IL-22 signaling) may be used in combination with another diagnostic tool to diagnose the severity of the cancer and/or the prognosis. For example, detected presence of IL-22, STAT3, DOT1L, SUZ12, and/or EED within colorectal cancer cells may be used in combination with other diagnostic tools specific for colorectal cancer detection such as, but not limited to, large intestine/colon specific antigen (PSA) testing, DRE, rectal palpitation, biopsy evaluation using Gleason scoring, radiography and symptomological evaluation by a qualified clinician.

In some embodiments, detecting the presence of IL-22 signaling and/or downstream targets of IL-22 signaling (e.g., STAT3 expression and/or activity, DOT1L expression and/or activity, SUZ12 expression and/or activity, EED expression and/or activity) within such colorectal cancer cells (e.g., tumor cells) is accomplished with an in vitro binding assay. For example, the presence of IL-22, STAT3, DOT1L, SUZ12, and/or EED can be detected within a biological sample having colorectal cancer cells by contacting the biological sample from a given subject with specific binding molecule(s) under conditions conducive for an interaction between the given binding molecule(s) and IL-22, STAT3, DOT1L, SUZ12, and/or EED. If a given biomolecule is present in the biological sample, it will form a complex with its binding molecule. To determine if the quantity of the detected biomolecule in a biological sample is comparable to a given quantity for subjects having varying stages of the colorectal cancer, an amount of a complex formed between the binding molecule and IL-22, STAT3, DOT1L, SUZ12, and/or EED can be determined by comparing to a standard. For example, if the amount of the complex falls within a quantitative value for a subject having a particular stage of a colorectal cancer, then the sample can be considered to be obtained from a subject having a similar stage of colorectal cancer. In vitro binding assays that are included within the scope of the invention are those known to the skilled in the art (e.g., ELISA, western blotting).

Thus, the present invention includes methods for characterizing the severity and/or stage of a colorectal cancer through detecting the presence of cancer stem cells activated through IL-22 signalling derived from IL-22 producing cells within cancer cells (e.g., tumor cells) obtained from a subject (e.g., human patient). Such methods comprise obtaining a biological sample from a subject, contacting said sample with a binding molecule specific for a differentially expressed biomolecule (e.g., IL-22, STAT3, DOT1L, SUZ12, and/or EED), detecting an interaction between the binding molecule and its specific biomolecule, wherein the detection of an interaction indicates the presence or absence of said biomolecule, thereby allowing for the characterization of the colorectal cancer (e.g., increased severity due to a detected presence of cancer stem cells activated through IL-22 signalling derived from IL-22 producing cells). Binding molecules include, but are not limited to, nucleic acids, nucleotides, oligonucleotides, polynucleotides, amino acids, peptides, polypeptides, proteins, monoclonal and/or polyclonal antibodies, antigens, sugars, carbohydrates, fatty acids, lipids, steroids, or combinations thereof (e.g. glycoproteins, ribonucleoproteins, lipoproteins), compounds or synthetic molecules. Preferably, binding molecules are antibodies specific for IL-22, STAT3, DOT1L, SUZ12, and/or EED.

For example, in vivo, antibodies or fragments thereof may be utilized for the detection of IL-22, STAT3, DOT1L, SUZ12, and/or EED in a biological sample having colorectal cancer cells, for example, by applying a labeled antibody directed against IL-22, STAT3, DOT1L, SUZ12, and/or EED to said biological sample under conditions that favor an interaction between the labeled antibody and its corresponding biomolecule. Depending on the nature of the biological sample, it is possible to determine not only the presence of a biomolecule, but also its cellular distribution. For example, in a blood serum sample, only the serum levels of a given biomolecule can be detected, whereas its level of expression and cellular localization can be detected in histological samples. It will be obvious to those skilled in the art, that a wide variety of methods can be modified in order to achieve such detection.

In another example, an antibody directed against a biomolecule of the invention (e.g., IL-22, STAT3, DOT1L, SUZ12, and/or EED) that is coupled to an enzyme is detected using a chromogenic substrate that is recognized and cleaved by the enzyme to produce a chemical moiety, which is readily detected using spectrometric, fluorimetric or visual means. Enzymes used to for labeling include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Detection may also be accomplished by visual comparison of the extent of the enzymatic reaction of a substrate with that of similarly prepared standards. Alternatively, radiolabelled antibodies can be detected using a gamma or a scintillation counter, or they can be detected using autoradiography. In another example, fluorescently labeled antibodies are detected based on the level at which the attached compound fluoresces following exposure to a given wavelength. Fluorescent compounds typically used in antibody labeling include, but are not limited to, fluorescein isothiocynate, rhodamine, phycoerthyrin, phycocyanin, allophycocyani, o-phthaldehyde and fluorescamine. In yet another example, antibodies coupled to a chemi- or bioluminescent compound can be detected by determining the presence of luminescence. Such compounds include, but are not limited to, luminal, isoluminal, theromatic acridinium ester, imidazole, acridinium salt, oxalate ester, luciferin, luciferase and aequorin.

Furthermore, in vivo techniques for detecting a biomolecule of the invention include introducing into a subject (e.g., human patient suffering from colorectal cancer) a labeled antibody directed against IL-22, STAT3, DOT1L, SUZ12, and/or EED.

In addition, methods of the present invention for characterizing a cancer (e.g., through detecting the presence of cancer stem cells activated through IL-22 signaling) described herein may be combined with other diagnostic methods to improve the outcome of such characterization. Other diagnostic methods are known to those skilled in the art.

In some embodiments, biomolecules of the invention (e.g., IL-22, STAT3, DOT1L, SUZ12, and/or EED) can be detected in blood, serum, plasma, urine, semen, seminal fluid, seminal plasma, pre-ejaculatory fluid (Cowper's fluid), nipple aspirate, vaginal fluid, excreta, tears, saliva, sweat, biopsy, ascites, cerebrospinal fluid, lymph, or tissue extract (biopsy) samples. Preferably, biological samples used to detect IL-22, STAT3, DOT1L, SUZ12, and/or EED include colorectal cancer cells (e.g., tumor cells).

A subject of the invention that is said to have colorectal cancer possesses morphological, biochemical, and functional alterations of their colorectal tissue such that the tissue can be characterized as a malignant neoplasm. The stage to which a colorectal cancer has progressed can be determined using known methods currently available to those skilled in the art (see, e.g., Union Internationale Conte Cancer (UICC) system or American Joint Committee on Cancer (AJC)). Currently, the most widely used method for determining the extent of malignancy of a colorectal neoplasm is the Gleason Grading system. Gleason grading is based exclusively on the architectural pattern of the glands of a colorectal neoplasm, wherein the ability of neoplastic cells to structure themselves into glands resembling those of the normal large intestine/colon is evaluated using a scale of 1 to 5. For example, neoplastic cells that are able to architecturally structure themselves such that they resemble normal large intestine/colon gland structure are graded 1-2, whereas neoplastic cells that are unable to do so are graded 4-5. As known to those skilled in the art, a colorectal neoplasm whose tumor structure is nearly normal will tend to behave, biologically, as normal tissue and therefore it is unlikely that it will be aggressively malignant.

Biologically active surfaces of the invention include, but are not limited to, surfaces that contain adsorbents with anion exchange properties (adsorbents that are positively charged), cation exchange properties (adsorbents that are negatively charged), hydrophobic properties, reverse phase chemistry, groups such as nitriloacetic acid that immobilize metal ions such as nickel, gallium, copper, or zinc (metal affinity interaction), or biomolecules such as proteins, antibodies, nucleic acids, or protein binding sequences, covalently bound to the surface via carbonyl diimidazole moieties or epoxy groups (specific affinity interaction). These surfaces may be located on matrices like polysaccharides such as sepharose, e.g. anion exchange surfaces or hydrophobic interaction surfaces, or solid metals, e.g. antibodies coupled to magnetic beads or a metal surface. Surfaces may also include gold-plated surfaces such as those used for Biacore Sensor Chip technology. Other surfaces known to those skilled in the art are also included within the scope of the invention.

Biologically active surfaces are able to adsorb biomolecules like nucleotides, nucleic acids, oligonucleotides, polynucleotides, amino acids, polypeptides, proteins, monoclonal and/or polyclonal antibodies, steroids, sugars, carbohydrates fatty acids, lipids, hormones, and combinations thereof (e.g., glycoproteins, ribonucleoproteins, lipoproteins).

In another embodiment, devices that use biologically active surfaces to selectively adsorb biomolecules may be chromatography columns for Fast Protein Liquid Chromatography (FPLC) and High Pressure Liquid Chromatography (HPLC), where the matrix, e.g. a polysaccharide, carrying the biologically active surface, is filled into vessels (usually referred to as "columns") made of glass, steel, or synthetic materials like polyetheretherketone (PEEK).

In yet another embodiment, devices that use biologically active surfaces to selectively adsorb biomolecules may be metal strips carrying thin layers of a biologically active surface on one or more spots of the strip surface to be used as probes for gas phase ion spectrometry analysis, for example the Sax2 of Q10 ProteinChip® array for (Ciphergen Biosystems, Inc.) for SELDI analysis.

In some embodiments, a profile of a biological sample may be generated using an array-based assay in which the biomolecules of a given sample (e.g., IL-22, STAT3, DOT1L, SUZ12, and/or EED) are bound by biochemical or affinity interactions to an adsorbent present on a biologically active surface located on a solid platform ("chip"). After the biomolecules (e.g., IL-22, STAT3, DOT1L, SUZ12, and/or EED) have bound to the adsorbent, they are co-crystallized with an energy absorbing molecule and subsequently detected using gas phase ion spectrometry. This includes, e.g., mass spectrometers, ion mobility spectrometers, or total ion current measuring devices. Quantity and characteristics of a biomolecule (e.g., IL-22, STAT3, DOT1L, SUZ12, and/or EED) can be determined using gas phase ion spectrometry. Other substances in addition to a biomolecule of interest can also be detected by gas phase ion spectrometry.

In one embodiment, a mass spectrometer can be used to detect a biomolecule(s) on a chip. In a typical mass spectrometer, a chip with a bound biomolecule(s) co-crystallized with an energy absorbing molecule is introduced into an inlet system of the mass spectrometer. The energy absorbing molecule:biomolecule crystals are then ionized by an ionization source, such as a laser. The ions generated are then collected by an ion optic assembly, and then a mass analyzer disperses and analyzes the passing ions. The ions exiting the mass analyzer are then detected by an ion detector. The ion detector then translates the information into mass-to-charge ratios. Detection of the presence of a biomolecule(s) (e.g., IL-22, STAT3, DOT1L, SUZ12, and/or EED) or other substances will typically involve detection of signal intensity. This, in turn, can reflect the quantity and character of a biomolecule bound to the probe.

In another embodiment, the mass profile of a sample may be generated using a liquid-chromatography (LC)-based assay in which biomolecule(s) of a given sample (e.g., IL-22, STAT3, DOT1L, SUZ12, and/or EED) are bound by biochemical or affinity interactions to an adsorbent located in a vessel made of glass, steel, or synthetic material; known to those skilled in the art as a chromatographic column. The biomolecule(s) (e.g., IL-22, STAT3, DOT1L, SUZ12, and/or EED) are eluted from the biologically active adsorbent surface by washing the vessel with appropriate solutions known to those skilled in the art. Such solutions include but are not limited to, buffers, e.g. Tris(hydroxymethyl)aminomethane hydrochloride (TRIS-HCl), buffers containing salt, e.g., sodium chloride (NaCl), or organic solvents, e.g., acetonitrile. Mass profiles of these biomolecules (e.g., IL-22, STAT3, DOT1L, SUZ12, and/or EED) are generated by application of the eluting biomolecules of the sample by direct connection via an electrospray device to a mass spectrometer (LC/ESI-MS).

MALDI is a well known technique (see, e.g., Brummell et al. (1994) Science 264: 399-402). In MALDI, a sample is partially purified to obtain a fraction that comprises a biomolecule by employing such separation methods as: two-dimensional gel electrophoresis (2D-gel) or high performance liquid chromatography (HPLC). Specifically, sample(s) and matrix with a positive charge are mixed together and flashed with a laser. The matrix becomes ionized (MH+) with an extra proton and then the proton is transferred to the sample to create a positively charged sample(s). The charged sample(s) is then run through a detector where the smaller ions reach the detector first and then the larger ions. This is the time of flight (TOF), and the mass to charge ratio (M/Z) is proportional to the square of the drift time.

In another embodiment, surface-enhanced laser desorption/ionization mass spectrometry (SELDI) can be used to detect a biomolecule (e.g., IL-22, STAT3, DOT1L, SUZ12, and/or EED), and uses a substrate comprising adsorbents to capture biomolecules, which can then be directly desorbed and ionized from the substrate surface during mass spectrometry. Since the substrate surface in SELDI captures biomolecules, a sample need not be partially purified as in MALDI. However, depending on the complexity of a sample and the type of adsorbents used, it may be desirable to prepare a sample to reduce its complexity prior to SELDI analysis. The SELDI is described, inter alia, in U.S. Pat. Nos. 5,719,060, 6,225,047, 6,579,719, and 6,818,411.

Conditions that promote binding of a biomolecule(s) to an adsorbent are known to those skilled in the art and ordinarily include parameters such as pH, the concentration of salt, organic solvent, or other competitors for binding of the biomolecule to the adsorbent.

There are many techniques readily available in the field for detecting the presence, absence, and/or level of an allele, transcript, or other biomarker, including mRNA microarrays. For example, enzymatic amplification of nucleic acid from an individual may be used to obtain nucleic acid for subsequent analysis (e.g., polymerase chain reaction (PCR) and reverse transcriptase-PCR (RT PCR)). The presence or absence of allele, transcript or other biomarker may also be determined directly from the individual's nucleic acid without enzymatic amplification.

Similarly, there are any number of techniques that may be employed to isolate and/or fractionate biomarkers (e.g., IL-22, STAT3, DOT1L, SUZ12, and/or EED). For example, a biomarker (e.g., IL-22, STAT3, DOT1L, SUZ12, and/or EED) may be captured using biospecific capture reagents, such as antibodies, aptamers, or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer, and hybrids of these.

Alternatively, for example, the presence of biomarkers (e.g., IL-22, STAT3, DOT1L, SUZ12, and/or EED) such as polypeptides may be detected using traditional immunoassay techniques. Immunoassay requires biospecific capture reagents, such as antibodies, to capture the analytes. The assay may be designed to specifically distinguish protein and modified forms of protein, which can be done by employing a sandwich assay in which a first antibody captures more than one form and a second distinctly-labeled antibody specifically binds and provide distinct detection of the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers (e.g., IL-22, STAT3, DOT1L, SUZ12, and/or EED) may be fractionated to isolate them from other components in a solution or blood that may interfere with detection. Fractionation may include platelet isolation from other blood components, sub-cellular fractionation of platelet components, and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface to which a capture reagent (also called an adsorbent or affinity reagent) is attached. Frequently, the surface of a biochip comprises a plurality of addressable locations, each of which has the capture reagent bound there.

With respect to protein-based testing, antibodies can be generated to the biomarkers (e.g., IL-22, STAT3, DOT1L, SUZ12, and/or EED) using standard immunological techniques, fusion proteins or synthetic peptides as described herein. Monoclonal antibodies can also be produced using now conventional techniques (see, e.g., Harlow and Lane (1988) Antibodies: A Laboratory Manual. Cold Spring Harbor Laboratory). It will also be appreciated that antibody fragments, e.g., Fab' fragments, can be similarly employed. Immunoassays, for example ELISAs, in which a test sample is contacted with antibody and binding to the biomarker detected, can provide a quick and efficient method of determining the presence and quantity of the biomarker. For example, antibodies can be used to test effects of pharmaceuticals in subjects enrolled in clinical trials.

Thus, the present invention also provides polyclonal and/or monoclonal antibodies and fragments thereof, and immunologic binding equivalents thereof, which are capable of specifically binding to biomarkers of the invention (e.g., IL-22, STAT3, DOT1L, SUZ12, and/or EED) and fragments thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule and injected over several months into a host mammal. A host's sera can be tested for immunoreactivity to a subject polypeptide or fragment. Monoclonal antibodies may be made by injecting mice with the protein polypeptides, fusion proteins, or fragments thereof. Monoclonal antibodies are screened by ELISA and tested for specific immunoreactivity with subject biomarkers or fragments thereof (see, e.g., Harlow and Lane (1988) Antibodies: A Laboratory Manual. Cold Spring Harbor Laboratory). These antibodies are useful in assays as well as a therapeutic drug.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical routes for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art.

Monoclonal antibodies with affinities of $10^8$ $M^{-1}$ or preferably $10^9$ to $10^{10}$ $M^{-1}$ or stronger will typically be made by standard procedures (see, e.g., Harlow and Lane (1988) Antibodies: A Laboratory Manual. Cold Spring Harbor Laboratory; Goding (1996) Monoclonal Antibodies: Principles and Practice, Academic Press, pp. 59-103). Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to antigenic biomarkers, or alternatively, to selection of libraries of antibodies in phage or similar vectors (see, e.g., Huse et al., (1989) Science, 246: 1275-81).

Polypeptides and antibodies of the present invention may be used with or without modification. Polypeptides and antibodies can be labeled by joining, either covalently or non-covalently, a substance, which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced (see, e.g., U.S. Pat. No. 4,816, 567).

Monoclonal antibodies can be generated according to various methods known to those skilled in the art. For example, any technique that provides for the production of antibody molecules by continuous cell lines in culture may be used. These include but are not limited to the hybridoma technique originally developed by Kohler and Milstein (1975), Nature, 205:495, as well as the trioma technique, the human B-cell hybridoma technique (see, e.g., Kozbor et al. (1983) Immunology Today 4: 72-79; Cote et al., (1983) Proc. Natl. Acad. Sci. U.S.A. 80:2026-2030), and the EBV-hybridoma technique to produce human monoclonal antibodies (Cole et al., (1985) in Monoclonal Antibodies and Cancer Therapy, Alan R. Liss, Inc., pp. 77-96). In fact, techniques developed for producing "chimeric antibodies" (see, e.g., Morrison et al., (1984) PNAS USA, 81:6851-6855; Neuberger et al., (1984) Nature, 312: 604-608) by splicing genes from a mouse antibody molecule specific for a given biomarker of the invention together with genes from a human antibody molecule of appropriate biological activity can be used. Such human or humanized chimeric antibodies are preferred for use in therapy of human diseases or disorders since the human or humanized antibodies are much less likely than xenogeneic antibodies to induce an immune response, in particular an allergic response.

The following example of monoclonal antibody production is meant for clarity and is not intended to limit the scope of the invention. One method to producing antibodies of the invention is by inoculating a host mammal with an immunogen comprising the intact subject biomarker (e.g., IL-22, STAT3, DOT1L, SUZ12, and/or EED) or its peptides (wild or mutant). The host mammal may be any mammal and is preferably a host mammal such as a mouse, rat, rabbit, guinea pig, hamster, or a mouse. By inoculating the host mammal it is possible to elicit the generation of antibodies directed towards the immunogen introduced into the host mammal. Several inoculations may be required to elicit an immune response.

To determine if the host mammal has developed antibodies directed towards the immunogen, serum samples are taken from the host mammal and screened for the desired antibodies (e.g., IL-22, STAT3, DOT1L, SUZ12, and/or EED). This can be accomplished by techniques known in the art such as radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immnunofluorescence assays, protein A assays, and immunoelectrophoresis assays, etc. In some embodiments, antibody binding is detected by detecting a label on the primary antibody. In some embodiments, the primary antibody is detected by detecting binding of a secondary antibody or reagent to the primary antibody. In some embodiments, the secondary antibody is labeled.

In some embodiments, once antibody generation is established in the host mammal, it is selected for hybridoma production. In some embodiments, the spleen is removed and a single cell suspension is prepared (see, e.g., Harlow and Lane (1988) Antibodies: A Laboratory Manual. Cold Spring Harbor Laboratory). Cell fusions are performed essentially as described by Kohler and Milstein (1975) Nature 256, 495-497.

Sandwich assays for detecting IL-22, STAT3, DOT1L, SUZ12, and/or EED within colorectal cancer cells can be used for characterizing a subject's cancer severity. In some embodiments, for example, sandwich assays consist of attaching a monoclonal antibody to a solid surface such as a plate, tube, bead, or particle, wherein the antibody is preferably attached to the well surface of a 96-well microtitre plate. A pre-determined volume of sample (e.g., serum, urine, tissue cytosol) containing the subject biomarker is added to the solid phase antibody, and the sample is incubated for a period of time at a pre-determined temperature conducive for the specific binding of the subject markers within the given sample to the solid phase antibody. Following, the sample fluid is discarded and the solid phase is washed with buffer to remove any unbound material. In some embodiments, one hundred µl of a second monoclonal antibody (to a different determinant on the subject biomarker) is added to the solid phase. This antibody is labeled with a detector molecule or atom (e.g., enzyme, fluorophore, chromophore, or $^{125}$I), and the solid phase with the second antibody is incubated for two hrs at room temperature. The second antibody is decanted and the solid phase is washed with buffer to remove unbound material. In some embodiments, the amount of bound label, which is proportional to the amount of subject biomarker present in the sample is quantitated.

In some embodiments, IL-22, STAT3, DOT1L, SUZ12, or EED peptides can be used to produce antibodies or similar IL-22, STAT3, DOT1L, SUZ12, or EED binding proteins. IL-22, STAT3, DOT1L, SUZ12, or EED peptides useful in producing antibodies can be made from the IL-22, STAT3, DOT1L, SUZ12, or EED polypeptide containing amino acids. Examples of inventive peptides of length X (in amino acids), as indicated by polypeptide positions with reference to, for example a recognized wild type amino acid sequence for IL-22, STAT3, DOT1L, SUZ12, or EED, include those corresponding to sets of consecutively overlapping peptides of length X, where the peptides within each consecutively overlapping set (corresponding to a given X value) are defined as the finite set of Z peptides from amino acid positions:

n to (n+(X−1));

where n=1, 2, 3, . . . (Y−(X−1));
where Y equals the length (amino acid or base pairs);
where X equals the common length (in amino acid) of each peptide in the set (e.g., X=10 for a set of consecutively overlapping 10-mers); and where the number (Z) of consecutively overlapping oligomers of length X for a given sequence of length Y is equal to Y−(X−1).

In certain embodiments, the present invention provides methods for treating colorectal cancer cells characterized with activated cancer stem cells (e.g., resulting from IL-22 signalling derived from IL-22 producing cells) through inhibiting cancer stem cell activation within such colorectal cancer cells.

The methods are not limited to a particular form or type of treating colorectal cancer cells characterized with activated cancer stem cells (e.g., resulting from IL-22 signaling) through inhibiting cancer stem cell activation within such colorectal cancer cells. In some embodiments, the treatment is a medical form of treatment, while in other embodiments, the treatment is an empirical (e.g., research based) form of treatment.

The methods are not limited to a particular manner for inhibiting cancer stem cell activation within such colorectal cancer cells. In some embodiments, inhibiting cancer stem cell activation within such colorectal cancer cells is accomplished through modulating (e.g., reducing, inhibiting) IL-22 signaling and/or downstream targets of IL-22 signaling (e.g., STAT3, DOT1L, SUZ12, EED) within such colorectal cancer cells. In some embodiments, the treatment involves the modulation (e.g., reduction, inhibition) of IL-22 signaling and/or downstream targets of IL-22 signaling combined with an addition form of treatment (e.g., chemotherapeutic treatment).

Such methods are not limited to particular techniques for modulating (e.g., reducing, inhibiting) IL-22 signaling and/or downstream targets of IL-22 signaling (e.g., STAT3, DOT1L, SUZ12, EED) within such colorectal cancer cells. In some embodiments, the present invention provides IL-22, STAT3, DOT1L, SUZ12, and/or EED modulators. In some embodiments, the present invention provides compositions comprising one or more modulators of IL-22, STAT3, DOT1L, SUZ12, and/or EED.

In some embodiments, the present invention provides methods that employ one or more modulators of IL-22, STAT3, DOT1L, SUZ12, and/or EED in in vivo, ex vivo, and in vitro applications where it is advantageous to reduce or eliminate cancer stem cell activation resulting from IL-22 signaling. IL-22, STAT3, DOT1L, SUZ12, and/or EED modulators may find use as drugs for supplementing cancer therapeutics and other agents. IL-22, STAT3, DOT1L, SUZ12, and/or EED modulators may also find use in other diseases of hyperproliferation (e.g., characterized with IL-22 signaling).

The present invention is not limited to a particular IL-22 modulator. Examples of IL-22 modulators (e.g., inhibitors) include soluble fragments of IL-22 polypeptides. The soluble fragments can be provided as fusion proteins (e.g., as IgG fusion proteins). IL-22 modulators can additionally include antibodies to IL-22 polypeptides, antisense molecules having a nucleotide sequence at least partially complementary to IL-22, proteins and/or peptides, as well as small molecule inhibitors of IL-22 polypeptides. The small molecules can act by inhibiting the expression and/or activity of an IL-22 polypeptide. In some embodiments, the IL-22 modulator is ARGX112 (arGEN-X). In some embodiments, the IL-22 modulator is Interleukin 22RA mAb (Merck). In some embodiments, the IL-22 modulator is a IL-22 blocking antibody. In some embodiments, the IL-22 modulator is a novel IL-22 modulator generated with any of the methods described in the present invention (e.g., a novel IL-22 antibody).

The present invention is not limited to a particular STAT3 modulator. Examples of STAT3 modulators (e.g., inhibitors) include soluble fragments of STAT3 polypeptides. The soluble fragments can be provided as fusion proteins (e.g., as IgG fusion proteins). STAT3 modulators can additionally include antibodies to STAT3 polypeptides, antisense molecules having a nucleotide sequence at least partially complementary to STAT3, proteins and/or peptides, as well as small molecule inhibitors of STAT3 polypeptides. STAT3 modulators can additionally include antibodies to STAT3 polypeptides, as well as small molecule inhibitors of STAT3 polypeptides. The small molecules can act by inhibiting the expression and/or activity of an STAT3 polypeptide. Examples of STAT3 inhibitors include, but are not limited to, PY*LKTK (see, e.g., Turkson, et al., J Biol Chem. 2001; 276(48):45443-55; Vutur, et al., Oncogene. 2004; 2315: 2600-16), Y*LPQTV (see, e.g., Ren, et al., Bioorg Med Chem Lett. 2003; 13(4):633-6; Coleman et al., J Med Chem. 2005; 48(21):6661-70), SS 610 (see, e.g., Turkson, et al., Mol Cancer Ther. 2004; 3(3):261-9), S3I-M2001 (see, e.g., Siddiquee, et al., ACS Chem Biol. 2007; 2(12):787-98), STA-21 (see, e.g., Song, et al., Proc Natl Acad Sci USA. 2005; 102(13):4700-5; Chen, et al., BMC Cancer. 2007; 7:111), S3I-201 (see, e.g., Sidiquee, et al., Proc Natl Acad Sci USA. 2007; 104(18):7391-6), Stattic (see, e.g., Schust (see, e.g., Chem Biol. 2006; 13(11):1235-42), catechol-containing compounds (see, e.g., Hao, et al., Bioorg Med Chem Lett. 2008; 18(18):4988-92), IS3 295 (see, e.g., Turkson, et al., J Biol Chem. 2005; 280(38):32979-88), CPA-1 and/or CPA-7 (see, e.g., Turkson, et al., Mol Cancer Ther. 2004; 3(12):1533-42), Galiellalactone (see, e.g., Weidler, et al., FEBS Lett. 2000; 484(1):1-6; Hellsten, et al., Prostate. 2008; 68(3):269-80), Peptide aptamers (see, e.g., Borghouts, et al., Mol Cancer Res. 2008; 6(2):267-81; Nagel-Wolfrum et al., Mol Cancer Res. 2004; 2(3):170-82), Decoy ODN (see, e.g., Leong, et al., Proc Natl Acad Sci USA. 2003; 100(7):4138-43; Xi, et al., Oncogene. 2005; 24(6):970-9), G-quartet ODN (see, e.g., Jing, et al., Cancer Res. 2004; 64(18):6603-9; Jing, et al., Mol Cancer Ther. 2006; 5(2):279-86; Weerasinghe, et al., Int J Oncol. 2007; 31(1):129-36), and peptides (see, e.g., Timofeeva, et al., ACS Chem Biol. 2007; 2(12):799-809). Additional examples of STAT3 modulators include, but are not limited to, pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(-1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof. In some embodiments, the STAT3 modulator is a novel STAT3 modulator generated with any of the methods described in the present invention (e.g., a novel STAT3 antibody).

The present invention is not limited to a particular DOT1L modulator. Examples of DOT1L modulators (e.g., inhibitors) include soluble fragments of DOT1L polypeptides. The soluble fragments can be provided as fusion proteins (e.g., as IgG fusion proteins). DOT1L modulators can additionally include antibodies to DOT1L polypeptides, antisense molecules having a nucleotide sequence at least partially complementary to DOT1L, proteins and/or peptides, as well as small molecule inhibitors of DOT1L polypeptides. DOT1L modulators can additionally include antibodies to DOT1L polypeptides, as well as small molecule inhibitors of DOT1L polypeptides. The small molecules can act by inhibiting the expression and/or activity of an DOT1L polypeptide. In some embodiments, the DOT1L modulator is the DOT1L inhibitor AURIGENE (Aurigene Discovery Technologies). In some embodiments, the DOT1L modulator is EPZ5676 (Epizyme). In some embodiments, the DOT1L modulator is a novel DOT1L modulator generated with any of the methods described in the present invention (e.g., a novel DOT1L antibody).

Compositions may be administered parenterally, topically, orally, or locally for therapeutic treatment. Preferably, the compositions are administered orally or parenterally, i.e., intravenously, intraperitoneally, intradermally, or intramuscularly.

Inventive compositions will include one or more IL-22, STAT3, DOT1L, SUZ12, and/or EED modulators and may further comprise a pharmaceutically-acceptable carrier or excipient. A variety of aqueous carriers may be used, e.g., water, buffered water, 0.4% saline, 0.3% glycine, and the like, and may include other proteins for enhanced stability, such as albumin, lipoprotein, globulin, etc., subjected to mild chemical modifications or the like.

IL-22, STAT3, DOT1L, SUZ12, and/or EED modulators useful in the treatment of disease (e.g., colorectal cancer) in mammals will often be prepared substantially free of naturally-occurring immunoglobulins or other biological molecules. Preferred IL-22, STAT3, DOT1L, SUZ12, and/or EED modulators will also exhibit minimal toxicity when administered to a mammal.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The selection of the appropriate method for administering IL-22, STAT3, DOT1L, SUZ12, and/or EED modulators of the present invention will depend on the nature of the application envisioned as well as the nature of the IL-22, STAT3, DOT1L, SUZ12, and/or EED modulator. Thus, for example, the precise methodology for administering a IL-22, STAT3, DOT1L, SUZ12, and/or EED modulator will depend upon whether it is an antisense molecule, a protein and/or peptide, an antibody or antibody fragment, or a small molecule. Other considerations include, for example, whether the IL-22, STAT3, DOT1L, SUZ12, and/or EED modulator will be used to regulate tumor cell initiation, growth, invasion, or metastasis, or as an adjunct to other cancer therapeutics.

In some embodiments, the IL-22, STAT3, DOT1L, SUZ12, and/or EED modulator is an antisense molecule. A variety of methods are available in the art for the administration of antisense molecules. Exemplary methods include gene delivery techniques, including both viral and non-viral based methods as well as liposome-mediated delivery methods.

Gene delivery methodologies will be effective to, for example, reduce tumor cell proliferation, or supplement radiation and/or chemotherapeutic treatment of tumors (see, e.g., Wheldon, T E et al., Radiother Oncol 1998; 48(1):5-13 (gene delivery methodologies for enhancement of fractionated radiotherapy)). By these methodologies, substantial therapeutic benefit may be achieved despite transfection efficiencies significantly less than 100%, transient retention of the transfected inhibitor, and/or existence of a subpopulation of target cells refractory to therapy.

Alternatively, gene delivery methodology may be used to directly knock-out endogenous IL-22, STAT3, DOT1L, SUZ12, and/or EED within tumor cells for purposes of preventing cancer stem cell activation resulting from IL-22 signaling within colorectal cancer cells. For example, the DOT1L gene may be targeted by transfection of a gene delivery vector carrying a DOT1L modulator. Preferential transfection into or expression within tumor cells may be achieved through use of a tissue-specific or cell cycle-specific promoter or through the use of trophic viruses that are confined to particular organs or structures, such as, e.g., a replication selective and neurotrophic virus that can only infect proliferating cells in the central nervous system.

Thus, to achieve therapeutic benefit, IL-22, STAT3, DOT1L, SUZ12, and/or EED within the tumor cells (e.g., colorectal cancer tumor cells) should be preferentially modulated. This can be accomplished by transfecting a gene expressing a IL-22, STAT3, DOT1L, SUZ12, and/or EED inhibitor, a IL-22, STAT3, DOT1L antisense molecule, a IL-22, STAT3, DOT1L, SUZ12, and/or EED gene-specific repressor, or an inhibitor of the protein product of the IL-22, STAT3, DOT1L, SUZ12, and/or EED gene.

As used herein, the phrase "gene delivery vector" refers generally to a nucleic acid construct that carries and, within certain embodiments, is capable of directing the expression of an antisense molecule of interest, as described in, for example, Molecular Biotechnology: Principles and Applications of Recombinant DNA, Ch. 21, pp. 555-590 (ed. B P Glick and J J Pasternak, $2^{nd}$ ed. 1998); Jolly, Cancer Gene Ther. 1994; 1:51-64; Kimura, Human Gene Ther. 1994; 5:845-852; Connelly, Human Gene Ther. 1995; 6:185-193; and Kaplitt, Nat. Gen. 1994; 6:148-153.

A number of virus- and non-virus-based gene delivery vector systems have been described that are suitable for the administration of IL-22, STAT3, DOT1L, SUZ12, and/or EED modulators. Virus-based gene delivery systems include, but are not limited to, retrovirus such as Moloney murine leukemia virus, spumaviruses, and lentiviruses; adenovirus; adeno-associated virus; and herpes-simplex virus vector systems. Viruses of each type are readily available from depositories or collections such as the American Type Culture Collection (ATCC; 10801 University Boulevard, Manassas, Va. 20110-2209) or may be isolated from known sources using commonly available materials and techniques.

The gene delivery vector systems of the present invention will find applications both in in vivo as well as ex vivo therapeutic regimens. Methods for gene delivery systems are well known in the art (e.g., retroviral gene delivery vector systems, adeno-associated viral gene delivery vector systems, and non-viral gene delivery vectors).

In certain embodiments, the present invention provides methods (e.g., therapeutic applications) for treating and/or preventing disorders related to activated cancer stem cell through IL-22 signaling (e.g., colorectal cancer) (e.g., colon cancer, rectal cancer, bowel cancer). In some embodiments, the methods involve administering one or more modulators of IL-22, STAT3, DOT1L, SUZ12, and/or EED for purposes of inhibiting (e.g., reducing, eliminating) cancer stem cell activation within colorectal cancer cells.

It is contemplated that the modulators described herein (e.g., modulators of IL-22, STAT3, DOT1L, SUZ12, and/or EED) are useful in the preparation of medicaments to treat a variety of conditions associated with cancer stem cells activated through IL-22 signaling within colorectal cancer cells. The methods and techniques for preparing medicaments of modulators described herein (e.g., modulators of IL-22, STAT3, DOT1L, SUZ12, and/or EED) are well-known in the art. Exemplary pharmaceutical formulations and routes of delivery are described below.

One of skill in the art will appreciate that any one or more of the modulators described herein (e.g., modulators of IL-22, STAT3, DOT1L, SUZ12, and/or EED) are prepared by applying standard pharmaceutical manufacturing procedures. Such medicaments can be delivered to the subject by using delivery methods that are well-known in the pharmaceutical arts.

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In some embodiments, the modulators described herein (e.g., modulators of IL-22, STAT3, DOT1L, SUZ12, and/or EED) are provided in unsolvated form or are in non-aqueous solutions (e.g., ethanol). The agents may be generated to allow such formulations through the production of specific crystalline polymorphs compatible with the formulations.

Various delivery systems are known and can be used to administer modulators described herein (e.g., modulators of IL-22, STAT3, DOT1L, SUZ12, and/or EED), e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the modulators described herein (e.g., modulators of IL-22, STAT3, DOT1L, SUZ12, and/or EED) can be administered to subjects or individuals susceptible to or at risk of developing a variety of conditions associated with cancer stem cell activation through IL-22 signaling within colorectal cancer cells. When the modulator is administered to a subject such as a mouse, a rat or a human patient, the modulator can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, any of the modulators described herein may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the modulator should be administered to achieve peak concentrations of the active modulators at sites of disease (e.g., colorectal cancer cells characterized with IL-22 signaling). This may be achieved, for example, by the intravenous injection of the modulator, optionally in saline, or orally administered, for example, as a tablet, capsule or syrup containing the active ingredient.

In certain embodiments, the present invention provides methods for inhibiting cancer stem cell activation within colorectal cancer cells (e.g., cancer stem cells activated through IL-22 signaling within colorectal cancer cells)) through expressing anti-sense constructs directed against IL-22, STAT3, DOT1L, SUZ12, and/or EED polynucleotides, and administering them to tumor cells, to inhibit gene function (e.g., gene function of IL-22, STAT3, DOT1L, SUZ12, and/or EED) and prevent the tumor cell from growing or progressing and/or cancer stem cells activated through IL-22 signaling within such colorectal cancer cells.

Anti-sense constructs may be used to inhibit gene function to prevent growth or progression in a proliferative cell. Antisense constructs, i.e., nucleic acid, such as RNA, constructs complementary to the sense nucleic acid or mRNA, are described in detail in U.S. Pat. No. 6,100,090, and Neckers et al., 1992, Crit Rev Oncog 3(1-2):175-231.

For example, in some embodiments, colorectal cancer characterized with cancer stem cells activated through IL-22 signaling may be treated or prevented by reducing the amount, expression or activity of IL-22, STAT3, DOT1L, SUZ12, and/or EED in whole or in part, for example by siRNAs capable of binding to and destroying IL-22, STAT3, DOT1L, SUZ12, and/or EED mRNA.

Indeed, in some embodiments, the present invention provides for an anti-IL-22 agent which downregulates IL-22 by RNA interference. In some embodiments, the present invention provides for an anti-STAT3 agent which downregulates STAT3 by RNA interference. In some embodiments, the present invention provides for an anti-DOT1L agent which downregulates DOT1L by RNA interference. The anti-IL-22 agent, anti-STAT3 agent, and/or anti-DOT1L agent may comprise a Small Interfering RNA (siRNA) or Short Hairpin RNA (shRNA).

For example, as described in Examples IV and VI, in some embodiments, the anti-STAT3 agent may comprise the following shRNA sequence (sense oligonucleotide sequence 5'-ATTGCTGCAGGTCGTTGGT-3' (SEQ ID NO: 1)), or shRNA sequence (sense oligonucleotide sequence 5'-TACCTAAGGCCATGAACTT-3' (SEQ ID NO: 2)). In some embodiments, as described in Examples IV and VI, the anti-DOT1L agent may comprise the following shRNA sequence (sense oligonucleotide sequence 5'-AGTTGTTGAGCTTCTCGGG-3' (SEQ ID NO: 3)). Methods of producing such shRNAs are described below.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded.

Suitable methods for RNAi in vitro are described herein. One such method involves the introduction of siRNA (small interfering RNA). Current models indicate that these 21-23 nucleotide dsRNAs can induce PTGS. RNA precursors such as Short Hairpin RNAs (shRNAs) can also be encoded by all or a part of a IL-22, STAT3, DOT1L, SUZ12, and/or EED nucleic acid sequence.

Alternatively, double-stranded (ds) RNA is a powerful way of interfering with gene expression in a range of organisms that has recently been shown to be successful in mammals (see, e.g., Wianny and Zernicka-Goetz, 2000, Nat Cell Biol 2:70-75). Double stranded RNA corresponding to the sequence of a IL-22, STAT3, DOT1L, SUZ12, and/or EED polynucleotide can be introduced into or expressed in oocytes and cells of a candidate organism to interfere with IL-22, STAT3, DOT1L, SUZ12, and/or EED activity.

Other methods of modulating IL-22, STAT3, DOT1L, SUZ12, and/or EED gene expression are known to those skilled in the art and include dominant negative approaches. Thus, another approach is to use non-functional variants of a IL-22, STAT3, DOT1L, SUZ12, and/or EED polypeptide that compete with the endogenous gene product resulting in inhibition of function.

IL-22, STAT3, DOT1L, SUZ12, and/or EED gene expression may also be modulated by introducing peptides or small molecules which inhibit gene expression or functional activity. Thus, compounds identified by the assays described here as binding to or modulating, such as down-regulating, the amount, activity or expression of a IL-22, STAT3, DOT1L, SUZ12, and/or EED polypeptide may be administered to tumor or proliferative cells to prevent the function of the respective IL-22, STAT3, DOT1L, SUZ12, and/or EED polypeptide. Such a compound may be administered along with a pharmaceutically acceptable carrier in an amount effective to down-regulate expression or activity IL-22, STAT3, DOT1L, SUZ12, and/or EED, or by activating or down-regulating a second signal which controls IL-22, STAT3, DOT1L, SUZ12, and/or EED expression, activity or amount, and thereby alleviating the abnormal condition (e.g., inhibiting cancer stem cell activation within colorectal cancer cells).

Alternatively, gene therapy may be employed to control the endogenous production of IL-22, STAT3, DOT1L, SUZ12, and/or EED by the relevant cells such as colorectal cells in the subject. For example, a polynucleotide encoding a IL-22, STAT3, DOT1L, SUZ12, and/or EED siRNA or a portion of this may be engineered for expression in a replication defective retroviral vector. The retroviral expression construct may then be isolated and introduced into a packaging cell transduced with a retroviral plasmid vector containing RNA encoding an anti-IL-22, STAT3, DOT1L, SUZ12, and/or EED siRNA such that the packaging cell now produces infectious viral particles containing the sequence of interest. These producer cells may be administered to a subject (e.g., human patient suffering from colorectal cancer characterized with cancer stem cells activated through IL-22 signaling) for engineering cells in vivo and regulating expression of the IL-22, STAT3, DOT1L, SUZ12, and/or EED polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of IL-22, STAT3, DOT1L, SUZ12, and/or EED is decreased in a colorectal cell. Furthermore, in such embodiments, treatment may be targeted to, or specific to, colorectal cells. The expression of IL-22, STAT3, DOT1L, SUZ12, and/or EED may be specifically decreased only in diseased colorectal cells (i.e., colorectal cancer cells characterized with cancer stem cells activated through IL-22 signaling), and not substantially in other non-diseased colorectal cells. In these methods, expression of IL-22, STAT3, DOT1L, SUZ12, and/or EED may be not substantially reduced in other cells, i.e., cells which are not colorectal cells. Thus, in such embodiments, the level of IL-22, STAT3, DOT1L, SUZ12, and/or EED remains substantially the same or similar in non-colorectal cells in the course of or following treatment.

Colorectal cell specific reduction of IL-22, STAT3, DOT1L, SUZ12, and/or EED levels may be achieved by targeted administration, i.e., applying the treatment only to the colorectal cells and not other cells. However, in other embodiments, down-regulation of IL-22, STAT3, DOT1L, SUZ12, and/or EED expression in colorectal cells (and not substantially in other cell or tissue types) is employed. Such methods may advantageously make use of colorectal specific expression vectors, for colorectal specific expression of for example siRNAs.

The present invention also includes methods involving co-administration of the modulators described herein (e.g., modulators of IL-22, STAT3, DOT1L, SUZ12, and/or EED) with one or more additional active agents. Indeed, it is a further aspect of this invention to provide methods for enhancing prior art therapies and/or pharmaceutical compositions by co-administering a modulator of this invention. In co-administration procedures, the agents may be administered concurrently or sequentially. In one embodiment, the modulators described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is associated with cancer stem cells activated through IL-22 signaling, the agent is known to treat cancer (e.g., colorectal cancer). A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anti-cancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORA- SONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein include one or more agents provided herein and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 7 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 7

| | |
|---|---|
| Aldesleukin (des-alanyl-1, serine-125 human interleukin-2) | Proleukin |
| Alemtuzumab (IgG1κ anti CD52 antibody) | Campath |
| Alitretinoin (9-cis-retinoic acid) | Panretin |
| Allopurinol (1,5-dihydro-4H-pyrazolo[3,4-d]pyrimidin-4-one monosodium salt) | Zyloprim |
| Altretamine (N,N,N',N',N'',N''-hexamethyl-1,3,5-triazine-2,4,6-triamine) | Hexalen |
| Amifostine (ethanethiol, 2-[(3-aminopropyl)amino]-, dihydrogen phosphate (ester)) | Ethyol |
| Anastrozole (1,3-Benzenediacetonitrile, a,a,a',a'-tetramethyl-5-(1H-1,2,4-triazol-1-ylmethyl)) | Arimidex |
| Arsenic trioxide | Trisenox |
| Asparaginase (L-asparagine amidohydrolase, type EC-2) | Elspar |
| BCG Live (lyophilized preparation of an attenuated strain of *Mycobacterium bovis* (*Bacillus Calmette*-Gukin [BCG], substrain Montreal) | TICE BCG |
| bexarotene capsules (4-[1-(5,6,7,8-tetrahydro-3,5,5,8,8-pentamethyl-2-napthalenyl) ethenyl] benzoic acid) | Targretin |
| bexarotene gel | Targretin |
| Bleomycin (cytotoxic glycopeptide antibiotics produced by *Streptomyces verticillus*; bleomycin $A_2$ and bleomycin $B_2$) | Blenoxane |
| Capecitabine (5'-deoxy-5-fluoro-N-[(pentyloxy)carbonyl]-cytidine) | Xeloda |

TABLE 7-continued

| | |
|---|---|
| Carboplatin (platinum, diammine [1,1-cyclobutanedicarboxylato(2-)-0,0']-,(SP-4-2)) | Paraplatin |
| Carmustine (1,3-bis(2-chloroethyl)-1-nitrosourea) | BCNU, BiCNU |
| Carmustine with Polifeprosan 20 Implant | Gliadel Wafer |
| Celecoxib (as 4-[5-(4-methylphenyl)-3-(trifluoromethyl)-1H-pyrazol-1-yl] benzenesulfonamide) | Celebrex |
| Chlorambucil (4-[bis(2chlorethyl)amino]benzenebutanoic acid) | Leukeran |
| Cisplatin ($PtCl_2H_6N_2$) | Platinol |
| Cladribine (2-chloro-2'-deoxy-b-D-adenosine) | Leustatin, 2-CdA |
| Cyclophosphamide (2-[bis(2-chloroethyl)amino] tetrahydro-2H-13,2-oxazaphosphorine 2-oxide monohydrate) | Cytoxan, Neosar |
| Cytarabine (1-b-D-Arabinofuranosylcytosine, $C_9H_{13}N_3O_5$) | Cytosar-U |
| cytarabine liposomal | DepoCyt |
| Dacarbazine (5-(3,3-dimethyl-1-triazeno)-imidazole-4-carboxamide (DTIC)) | DTIC-Dome |
| Dactinomycin, actinomycin D (actinomycin produced by *Streptomyces parvullus*, $C_{62}H_{86}N_{12}O_{16}$) | Cosmegen |
| Darbepoetin alfa (recombinant peptide) | Aranesp |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox (recombinant peptide) | Ontak |
| Dexrazoxane ((S)-4,4'-(1-methyl-1,2-ethanediyl)bis-2,6-piperazinedione) | Zinecard |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex |
| doxorubicin | Adriamycin PFS Intravenous injection |
| doxorubicin liposomal | Doxil |
| dromostanolone propionate (17b-Hydroxy-2a-methyl-5a-androstan-3-one propionate) | Dromostanolone |
| dromostanolone propionate | Masterone injection |
| Elliott's B Solution | Elliott's B Solution |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence |
| Epoetin alfa (recombinant peptide) | Epogen |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate (4'-Demethylepipodophyllotoxin 9-[4,6-O-(R)-ethylidene-(beta)-D-glucopyranoside], 4'-(dihydrogen phosphate)) | Etopophos |
| etoposide, VP-16 (4'-demethylepipodophyllotoxin 9-[4,6-0-(R)-ethylidene-(beta)-D-glucopyranoside]) | Vepesid |

TABLE 7-continued

| | |
|---|---|
| Exemestane (6-methylenandrosta-1,4-diene-3,17-dione) | Aromasin |
| Filgrastim (r-metHuG-CSF) | Neupogen |
| floxuridine (intraarterial) (2'-deoxy-5-fluorouridine) | FUDR |
| Fludarabine (fluorinated nucleotide analog of the antiviral agent vidarabine, 9-b-D-arabinofuranosyladenine (ara-A)) | Fludara |
| Fluorouracil, 5-FU (5-fluoro-2,4(1H,3H)-pyrimidinedione) | Adrucil |
| Fulvestrant (7-alpha-[9-(4,4,5,5,5-penta fluoropentylsulphinyl) nonyl]estra-1,3,5-(10)-triene-3,17-beta-diol) | Faslodex |
| Gemcitabine (2'-deoxy-2',2'-difluorocytidine monohydrochloride (b-isomer)) | Gemzar |
| Gemtuzumab Ozogamicin (anti-CD33 hP67.6) | Mylotarg |
| Goserelin acetate | Zoladex Implant |
| Hydroxyurea | Hydrea |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide (3-(2-chloroethyl)-2-[(2-chloroethyl)amino]tetrahydro-2H-1,3,2-oxazaphosphorine 2-oxide) | IFEX |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a (recombinant peptide) | Roferon-A |
| Interferon alfa-2b (recombinant peptide) | Intron A (Lyophilized Betaseron) |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar |
| Letrozole (4,4'-(1H-1,2,4-Triazol-1-ylmethylene) dibenzonitrile) | Femara |
| Leucovorin (L-Glutamic acid, N[4[[(2amino-5-formyl1,4,5,6,7,8-hexahydro4oxo6-pteridinyl)methyl]amino]benzoyl], calcium salt (1:1)) | Wellcovorin, Leucovorin |
| Levamisole HCl ((−)-(S)-2,3,5,6-tetrahydro-6-phenylimidazo [2,1-b] thiazole monohydrochloride $C_{11}H_{12}N_2S$•HCl) | Ergamisol |
| Lomustine (1-(2-chloro-ethyl)-3-cyclohexyl-1-nitrosourea) | CeeNU |
| Meclorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl) amino]-L-phenylalanine) | Alkeran |
| Mercaptopurine, 6-MP (1,7-dihydro-6H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methylamino]benzoyl]-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl) ethane) | Lysodren |

TABLE 7-continued

| Drug | Brand |
|---|---|
| Mitoxantrone (1,4-dihydroxy-5,8-bis[[2-[(2-hydroxyethyl)amino]ethyl]amino]-9,10-anthracenedione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N'] [oxalato(2-)-O,O'] platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R,3S)—N-benzoyl-3-phenylisoserine) | TAXOL |
| Pamidronate (phosphonic acid (3-amino-1-hydroxypropylidene) bis-, disodium salt, pentahydrate, (APD)) | Aredia |
| Pegademase ((monomethoxypolyethylene glycol succinimidyl) 11-17-adenosine deaminase) | Adagen (Pegademase Bovine) |
| Pegaspargase (monomethoxypolyethylene glycol succinimidyl L-asparaginase) | Oncaspar |
| Pegfilgrastim (covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin (antibiotic produced by *Streptomyces plicatus*) | Mithracin |
| Porfimer sodium | Photofrin |
| Procarbazine (N-isopropyl-μ-(2-methylhydrazino)-p-toluamide monohydrochloride) | Matulane |
| Quinacrine (6-chloro-9-(1-methyl-4-diethyl-amine) butylamino-2-methoxyacridine) | Atabrine |
| Rasburicase (recombinant peptide) | Elitek |
| Rituximab (recombinant anti-CD20 antibody) | Rituxan |
| Sargramostim (recombinant peptide) | Prokine |
| Streptozocin (streptozocin 2-deoxy-2-[[[(methylnitrosoamino)carbonyl]amino]-a(and b)-D-glucopyranose and 220 mg citric acid anhydrous) | Zanosar |
| Talc ($Mg_3Si_4O_{10}(OH)_2$) | Sclerosol |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex |
| Temozolomide (3,4-dihydro-3-methyl-4-oxoimidazo[5,1-d]-as-tetrazine-8-carboxamide) | Temodar |
| teniposide, VM-26 (4'-demethylepipodophyllotoxin 9-[4,6-0-(R)-2-thenylidene-(beta)-D-glucopyranoside]) | Vumon |
| Testolactone (13-hydroxy-3-oxo-13,17-secoandrosta-1,4-dien-17-oic acid [dgr]-lactone) | Teslac |
| Thioguanine, 6-TG (2-amino-1,7-dihydro-6H-purine-6-thione) | Thioguanine |
| Thiotepa (Aziridine, 1,1',1''-phosphinothioylidynetris-, or Tris (1-aziridinyl) phosphine sulfide) | Thioplex |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin |
| Toremifene (2-(p-[(Z)-4-chloro-1,2-diphenyl-1-butenyl]-phenoxy)-N,N-dimethylethylamine citrate (1:1)) | Fareston |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar |

TABLE 7-continued

| | |
|---|---|
| Trastuzumab (recombinant monoclonal IgG$_1$ kappa anti-HER2 antibody) | Herceptin |
| Tretinoin, ATRA (all-trans retinoic acid) | Vesanoid |
| Uracil Mustard | Uracil Mustard Capsules |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar |
| Vinblastine, Leurocristine ($C_{46}H_{56}N_4O_{10} \cdot H_2SO_4$) | Velban |
| Vincristine ($C_{46}H_{56}N_4O_{10} \cdot H_2SO_4$) | Oncovin |
| Vinorelbine (3',4'-didehydro-4'-deoxy-C'-norvincaleukoblastine [R-(R*,R*)-2,3-dihydroxybutanedioate (1:2)(salt)]) | Navelbine |
| Zoledronate, Zoledronic acid ((1-Hydroxy-2-imidazol-1-yl-phosphonoethyl) phosphonic acid monohydrate) | Zometa |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, Gl7DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering one or more modulators provided herein (e.g., modulators of IL-22, STAT3, DOT1L, SUZ12, and/or EED) with radiation therapy. The methods provided herein are not limited by the types, amounts, or delivery and administration systems used to deliver therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in therapeutic period. In one embodiment, radiation is initiated in week 1 or week 2, and is administered for the remaining duration of therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

In some embodiments of the methods provided herein, one or more modulators provided herein (e.g., modulators of IL-22, STAT3, DOT1L, SUZ12, and/or EED) and one or more therapeutic agents or anticancer agents are administered to an animal under one or more of the following conditions: at different periodicities, at different durations, at different concentrations, by different administration routes, etc. In some embodiments, the modulator is administered prior to therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of therapeutic or anticancer agent. In some embodiments, the modulator is administered after therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the modulator and therapeutic or anticancer agent are administered concurrently but on different schedules, e.g., the modulator is administered daily while therapeutic or anticancer agent is administered once a week, once every two weeks, once every three weeks, or once every four weeks. In other embodiments, the modulator is administered once a week while therapeutic or anticancer agent is administered daily, once a week, once every two weeks, once every three weeks, or once every four weeks.

In certain embodiments, the present invention provides a method of drug screening including providing a model comprising a quantity of colorectal cancer cells constitutively expressing IL-22, STAT3, DOT1L, SUZ12, and/or EED, or a transgenic animal that overexpresses IL-22, STAT3, DOT1L, SUZ12, and/or EED within colorectal cancer cells, administering one or more drugs to the model, and detecting a change in the model to determine if the one or more drugs has an effect of interest on the model (e.g., preventing cancer cell activation within such colorectal cancer cells resulting from IL-22 signalling within such colorectal cancer cells). In some embodiments, the cells expressing IL-22, STAT3, DOT1L, SUZ12, and/or EED also express a fluorescent marker. In some embodiments, the fluorescent marker is green fluorescent protein (GFP), enhanced green fluorescent protein (EGFP), red fluorescent protein (RFP), blue fluorescent protein (BFP), yellow fluorescent protein (YFP), or GFP-luciferase fusion protein. The present invention also provides a method of drug screening including providing an animal model as described herein, administering one or more drugs to the animal, and detecting a change in or reaction by the animal to determine if the drug has an effect of interest.

In certain embodiments, the present invention provides kits for the detection, characterization, and/or treatment of cancers characterized with cancer stem cells activated through IL-22 signalling (e.g., colorectal cancer) (e.g., colon cancer, bowel cancer, rectal cancer). In some embodiments, the kits contain antibodies specific for IL-22, STAT3, DOT1L, SUZ12, and/or EED. In some embodiments, kits contain modulators (e.g., inhibitors) of IL-22, STAT3, DOT1L, SUZ12, and/or EED. In some embodiments, the kits further contain detection reagents and buffers. In other embodiments, the kits contain reagents specific for the detection of nucleic acids (e.g., DNA, RNA, mRNA or cDNA, oligonucleotide probes or primers). In preferred embodiments, the kits contain all of the components necessary and/or sufficient to perform a detection assay, including all controls, directions for performing assays, and any necessary software for analysis and presentation of results.

EXPERIMENTAL

The following examples are provided in order to demonstrate and further illustrate certain preferred embodiments and aspects of the present invention and are not to be construed as limiting the scope thereof.

Example I

This example demonstrates that IL-22 in the tumor environment promotes colon cancer sternness.

As IL-22 protects intestinal stem cells from immune-mediated tissue damage in mice (see, e.g., Hanash, A. M. et al. (2012) Immunity 37, 339-350), it was hypothesized that IL-22$^+$ cells might support cancer sternness in patients with colon cancer. High levels of IL-22 mRNA were initially detected in primary colon cancer tissues as compared to peripheral blood (FIG. 1A). The effects of endogenous IL-22 on primary tumor formation in a female NOD/Shi-scid/IL-2Rγnull (NSG) mouse model (see, e.g., Curiel, T. J. et al. (2004) Nat Med 10, 942-949; Kryczek, I. et al. (2012) Int J Cancer 130, 29-39; Kryczek, I., et al. (2011) Sci Transl Med 3, 104ra100; Zou, W., et al. (1997) J Virol 71, 1227-1236) were next examined. To this end, single cell suspensions were made from fresh colon cancer tissues. These cells were equally divided into two groups and injected into NSG mice with one-time treatment of either anti-IL-22 monoclonal antibody (mAb) or isotype mAb. Interestingly, anti-IL-22 mAb dramatically reduced primary tumor volume (FIG. 1B) and tumor incidence (FIG. 1C), and increased mouse survival (FIG. 1D). The data indicates that IL-22 in the colon cancer environment promote colon tumorigenesis in vivo.

Figure 13:
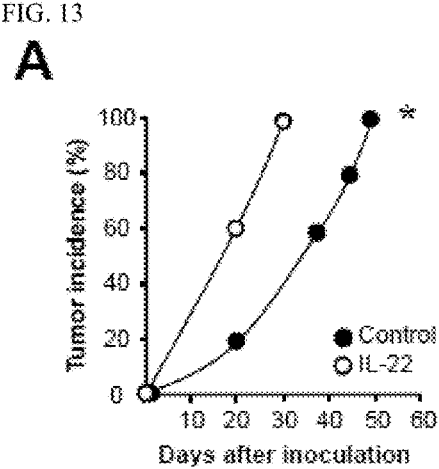
FIG. 13A-B demonstrates that IL-22 promotes colon cancer development and growth. IL-22 treated $10^6$ DLD-1 cells were inoculated into NSG mice. Tumor incidence (A) and tumor growth (B) were recorded. n=5 per group, P<0.05.
Figure 13:
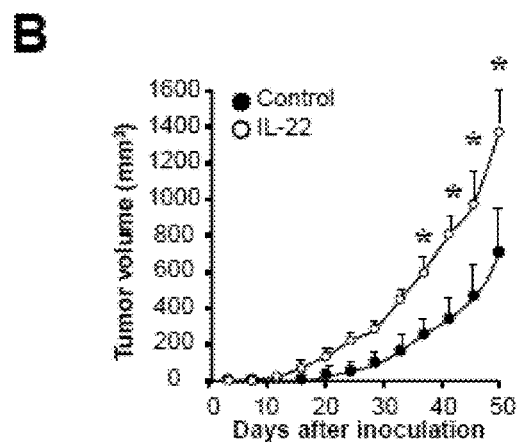

To confirm the tumorigenic potential of endogenous IL-22, different concentrations of a colorectal adenocarcinoma cancer cell line, DLD-1 cells, were injected into the NSG mice to determine a nontumorigenic concentration. It was found that $10^5$ DLD-1 cells failed to form a tumor in the NSG mouse model. However, exogenous IL-22 administration enabled tumor formation with $10^5$ DLD-1 cells as shown by increased tumor volume (FIG. 1E) and incidence (FIG. 1F) and decreased mouse survival (FIG. 1G). When $10^6$ DLD-1 cells were inoculated into mice, IL-22 accelerated tumor development (FIG. 13A) and growth as well (FIG. 13B). Thus, IL-22 may enhance tumorigenesis by altering cancer stem cell properties.

In support of this notion, IL-22 promoted tumor sphere formation in a dose dependent manner (FIG. 1H, I) and increased aldehyde dehydrogenase (ALDH1) activity in DLD-1, HT29 and two primary colon cancer cell lines (FIG. 1J). ALDH1 is an operative marker of human cancer stem cells (see, e.g., Carpentino, J. E. et al. (2009) Cancer Res 69, 8208-8215; Kryczek, I. et al. (2012) Int J Cancer 130, 29-39). Furthermore, IL-22 enhanced the mRNA (FIG. 1K) and protein (FIG. 1L, M) levels of multiple stem cell core genes including NANOG, SOX2, and POU5F1 (OCT3/4). Altogether, IL-22 promotes colon cancer sternness and tumorigenicity.

Example II

This example demonstrates that Th22 cells are recruited into the tumor and promote cancer sternness via IL-22.

Figure 3:
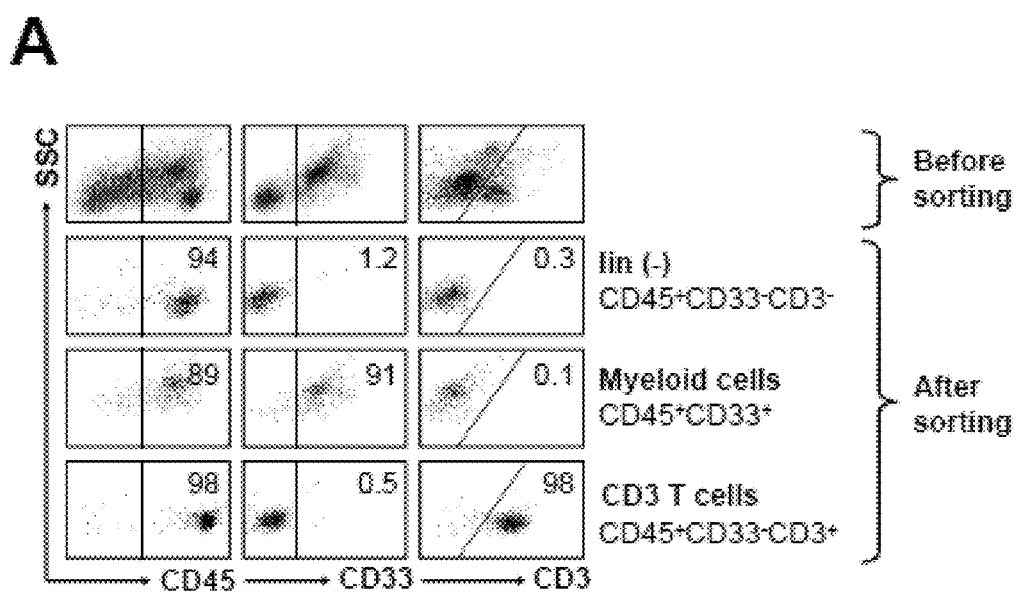
FIG. 3A-B presents immune cell subsets in the colon cancer microenvironment. Single cells were prepared from fresh colon cancer tissues and were stained for the following markers: immune cells (CD45), myeloid cells (CD33), T cells (CD3), and NK/NKT cells (CD56). (A) Immune cell subsets were shown before and after sorting. n=5. (B) Percentage of immune cell subsets is shown as the mean±SEM. n=10, *P<0.05.
Figure 3:
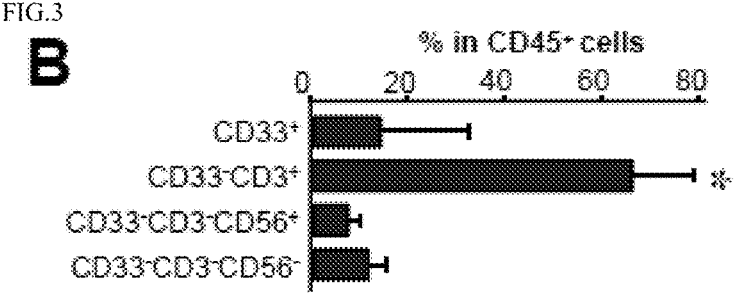

Given that IL-22 promotes colon cancer sternness, the cellular source of IL-22 and the phenotype of IL-22$^+$ cells in the human colon cancer environment were examined. Real-time PCR revealed that IL-22 was expressed by CD45$^+$ immune cells in the colon cancer environment (FIG. 2A). Based on polychromatic flow cytometry analysis (FIG. 3A), CD3$^+$ T cells were the major immune component in the colon cancer CD45$^+$ cells (FIG. 3B). To further define the phenotype of the IL-22$^+$ cells, colon cancer associated CD45$^+$ immune cells were sorted into four populations, lineage negative cells (lin$^-$), CD33$^-$CD3$^-$CD56$^+$ cells (potential NK/ILCs), CD33$^+$ myeloid cells and CD3$^+$ T cells. It was found that IL-22 mRNA expression was confined to the CD3$^+$ T cells (FIG. 2B). Furthermore, sorted colon cancer associated CD45$^+$CD3$^+$ T cells, but not colon CD45$^+$CD3$^-$ and blood CD45$^+$ CD3$^-$ cells, spontaneously released IL-22 (FIG. 2E). Once activated, the colon cancer associated CD45$^+$CD3$^+$ T cells produced IL-22 (FIG. 2D) and expressed high levels of intracellular IL-22 (FIG. FIG. 2E). Thus, IL-22 is predominantly expressed by Th22 cells in colorectal cancer patients.

Figure 4:
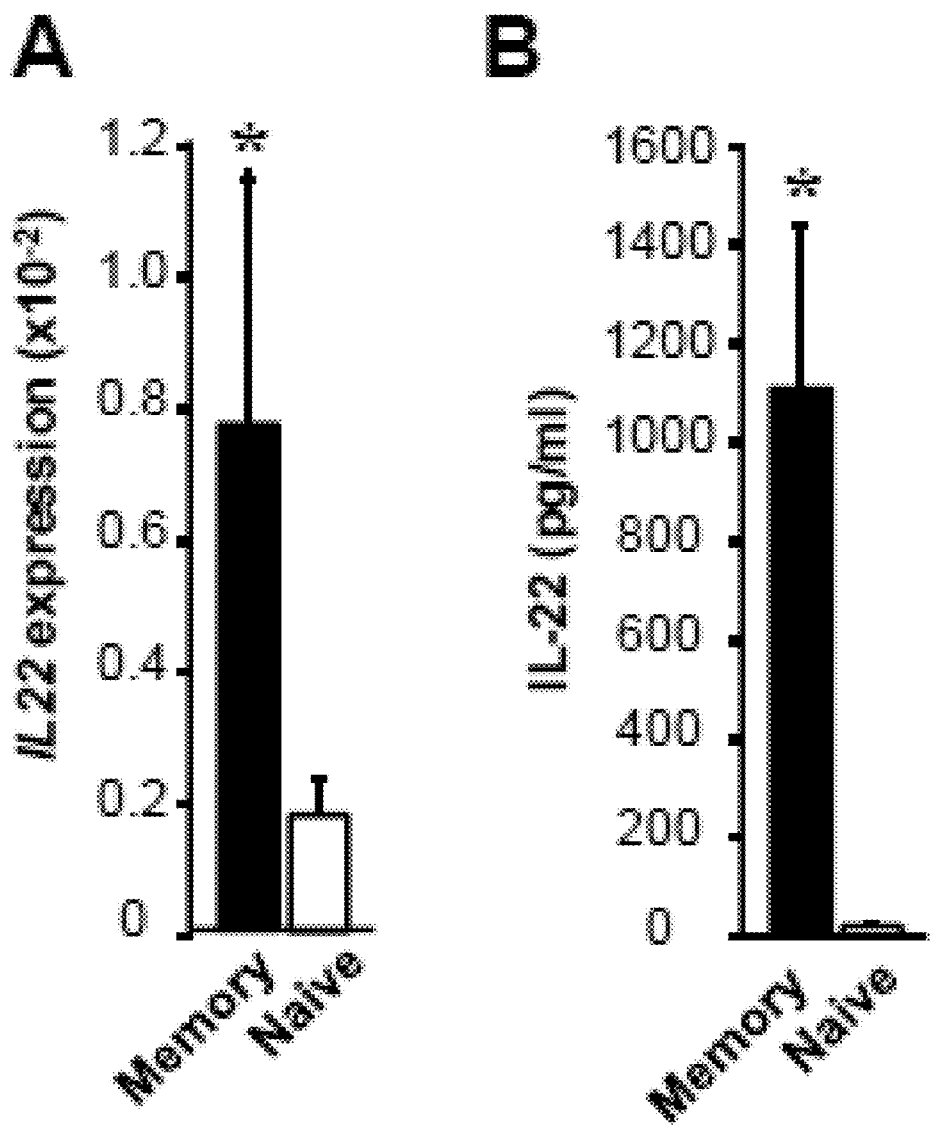
FIG. 4A-B demonstrats that memory CD4$^+$ T cells expresses IL-22. CD45RA$^-$CD45RO$^-$ (naïve) and CD45RA$^-$CD45RO$^+$ (memory) CD4$^+$ T cells were sorted from peripheral blood. (A) The expression of IL-22 was measured by real time PCR in freshly sorted cells. (B) The sorted cells were activated for 3 days with anti-CD3 and anti-CD28. IL-22 was detected in the culture supernatants by ELISA. n=5, * P<0.05.
Figure 5:
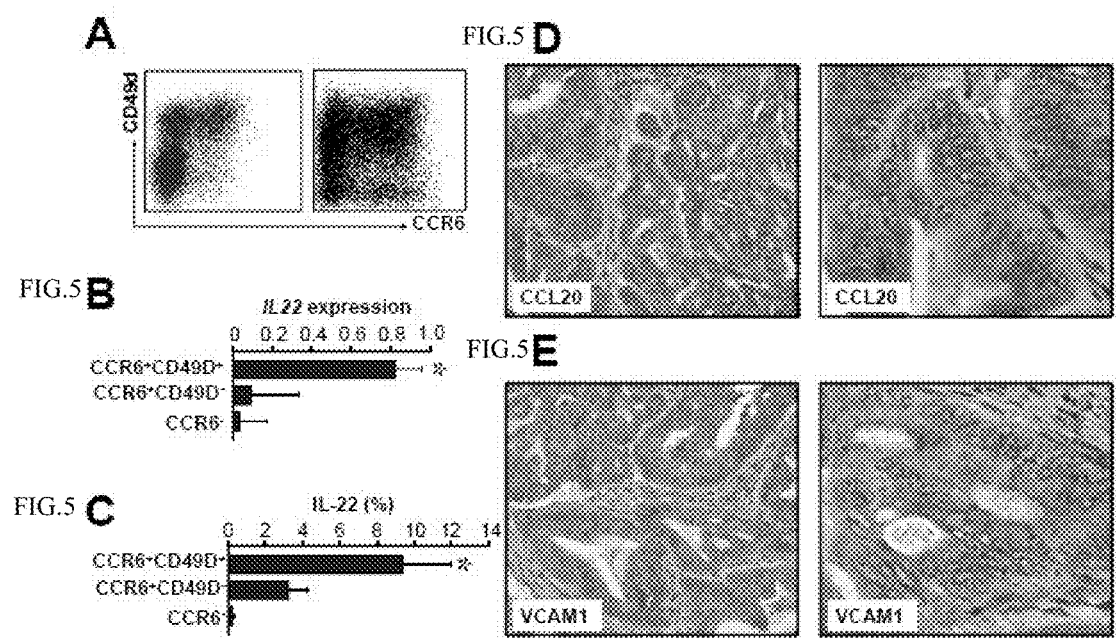
FIG. 5A-E demonstrates that Th22 cells are CCR6$^+$ CD49D$^+$ and traffic into the colon cancer microenvironment. (A) CCR6 and CD49D are co-expressed in CD4$^+$ T cells. Expression of CCR6 and CD49D was analyzed in CD4$^+$ T cells by FACS. One of 4 donors is shown. (B, C) CCR6$^+$ CD49d$^+$CD4$^+$ T cells expressed IL-22. CCR6$^+$CD49d$^+$ T cells were sorted and activated with anti-CD3 and anti-CD28 and antigen presenting cells (APC). IL-22 mRNA was detected by real time PCR (B). IL-22 protein was detected by intracellular staining (C). 5 different donors (P<0.05). (D, E) Colon cancer tissues expresses CCL20 and VCAM-1. Immunohistochemistry staining was performed with anti-CCL20 (d) and anti-VCAM-1 (E) mAbs. n=5. Magnification: ×100 (left panel) and ×400 (right panel).

How peripheral blood Th22 cells traffic into the colon cancer microenvironment was next examined. The expression of cell trafficking associated molecules including chemokine receptors and integrins on Th22 cells in blood and colon cancer was analyzed. It was found that IL-22 was expressed by memory, but not naïve, CD4$^+$ T cells in blood (FIG. 4). Blood CD4$^+$ T cells was sorted into CCR6$^-$ and CCR6$^+$ populations, and subsequently examined IL-22 expression. Intracellular staining was not performed as this staining affects the detection of surface antigens. It was found CCR6$^+$, but not CCR6$^-$ cells expressed high levels of IL-22 mRNA (FIG. 2F) and protein (FIG. 2G). CCR6$^+$ T cells largely co-expressed CD49D integrin, the ligand for VCAM1 (FIG. 5A). Among CCR6$^+$ cells, IL-22 was predominantly expressed by primary (FIG. 5B) and activated (FIG. 5C) CD49D$^+$ cells. Thus, Th22 cells are enriched in the CCR6$^+$CD49D$^+$ memory T cell pool.

Whether Th22 cells could migrate toward primary tumor tissues through CCL20, the ligand for CCR6, was next investigated. It was observed that T cells efficiently migrated in response to CCL20, and that the migrating cells were enriched for IL-22$^+$ T cells (FIG. 2H), expressing CCR6 and CD49D (FIG. 2I). Furthermore, high levels of CCL20 (FIG. 5D), and VCAM1 (FIG. 5E) were detected in colon cancer tissues. The data suggest that CCR6 and CD49D signaling promotes homing of Th22 cells to the colon cancer microenvironment.

The potential effects of primary colon cancer associated Th22 cells on colon cancer sternness was investigated. To this end, colon cancer cell sphere assay was performed with autologous colon cancer associated CD4$^+$ T cells. It was shown that these T cells enhanced primary colon cancer cell sphere formation while anti-IL-22 abrogated this effect (FIG. 2J). In line with this, these T cells also increased core stem cell gene expression (FIG. 2K) and ALDH1 activity (FIG. 2L) in colon cancer cells. This increase in stemness was reduced with IL-22 blockade (FIG. 2K, L). Thus, Th22 cells traffic into the tumor, and promote colon cancer sternness via secreting IL-22 in the colon cancer microenvironment.

Example III

This example demonstrates that IL-22 promotes colon cancer sternness via STAT3 activation.

Figure 6:
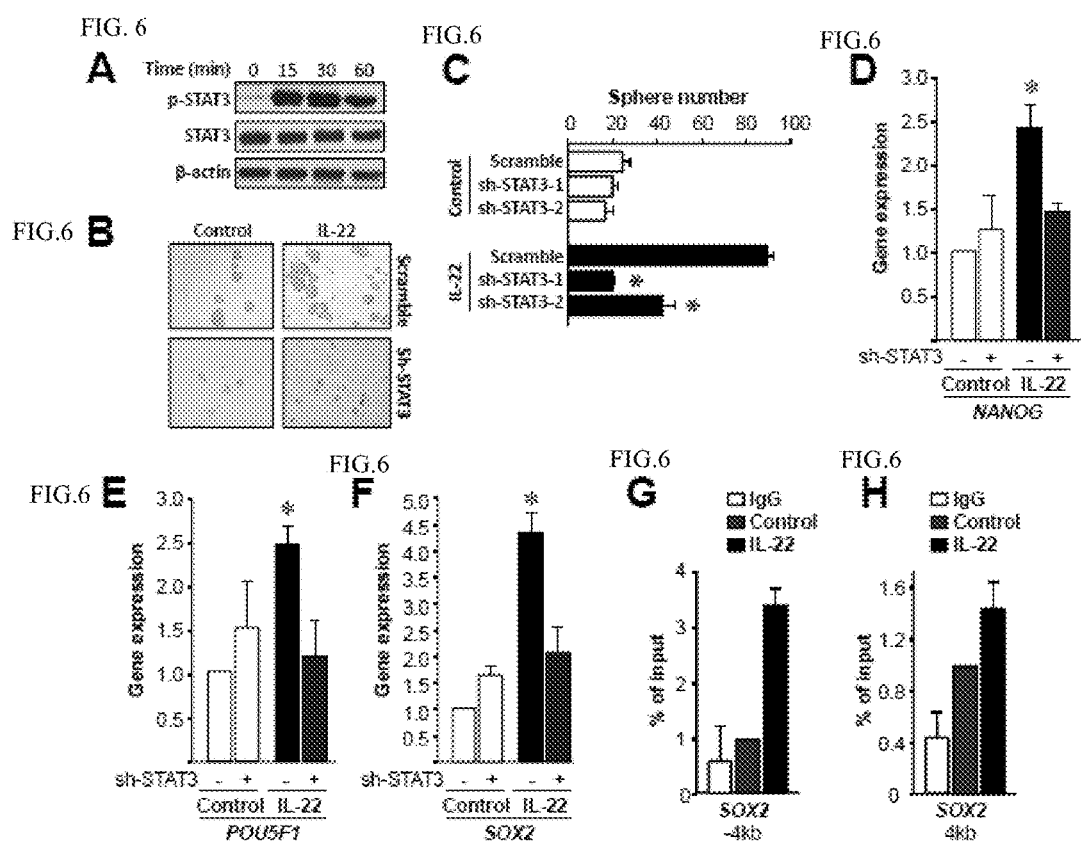
FIG. 6A-H demonstrates that IL-22 promotes colon cancer sternness via STAT3 activation. (A) IL-22 induced STAT3 phosphorylation. Colon cancer cells were treated with IL-22 for different time points. The protein levels of phosphorylated STAT3 and STAT3 were detected by Western blotting. (B, C) IL-22 induced colon cancer spheres via STAT3. Sphere assay was performed with shSTAT3 colon cancer cells in the presence of IL-22. Results were shown as sphere images (b) and the mean numbers of spheres in triplicate (c). (n=5. P<0.01). (D-F) IL-22 stimulated colon cancer sternness gene expression via STAT3. Colon cancer cells expressing shSTAT3 or scrambled vector were cultured with IL-22. Stem cell core gene mRNAs were detected by real-time PCR after 6 hours (n=5, *P<0.05). (G, H) IL-22 causes STAT3 occupancy on SOX2 promoter areas. STAT3-ChIP assay was performed in DLD-1 cells cultured with or without IL-22. One of at least three experiments is shown.
Figure 7:
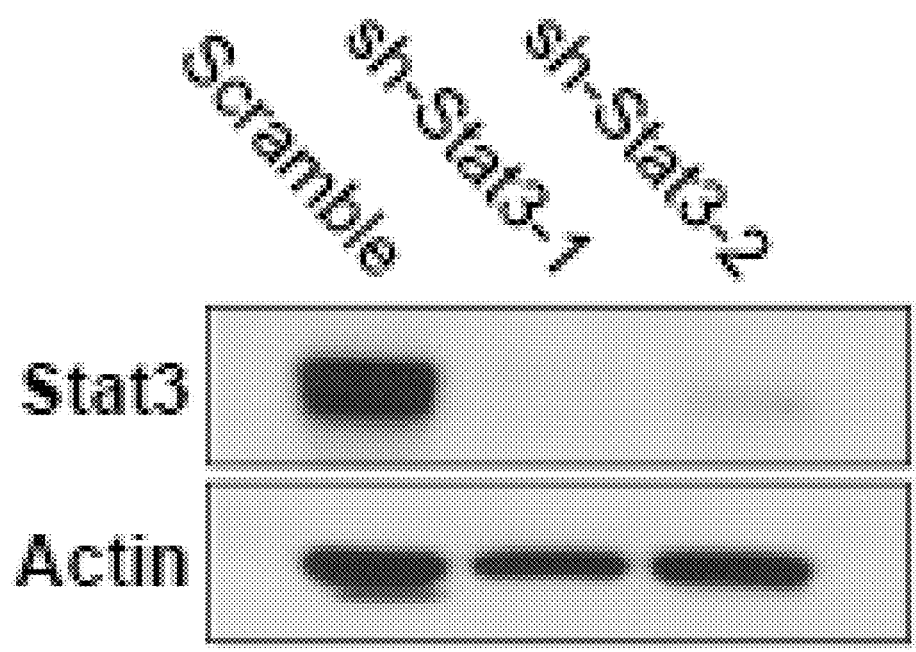
FIG. 7 demonstrates STAT3 expression knock down via shRNA. DLD1 cells were transfected with control vectors or sh-STAT3-1 and sh-STAT3-2. STAT3 expression was detected by western blot.

The molecular mechanisms by which IL-22 promotes colon cancer sternness was next investigated. STAT3 plays a key role in the crosstalk between cancer and immune cells in the tumor microenvironment (see, e.g., Lee, H., et al. (2009) Cancer Cell 15, 283-293; Yu, H., et al. (2007) Nat Rev Immunol 7, 41-51). In line with previous reports (see, e.g., Lejeune, D. et al. (2002) J Biol Chem 277, 33676-33682; Pickert, G., et al. (2009) J Exp Med 206, 1465-1472), it was observed that IL-22 activated STAT3 in colon cancer cells (FIG. 6A). The effect of IL-22 on sternness was STAT3 dependent as STAT3 knockdown (sh-STAT3) (FIG. 7) resulted in reduced colon cancer sphere numbers (FIG. 6B, C) and core stem cell gene expression (FIG. 6D-F). It was speculated that STAT3 may directly bind to the promoters of core stem cell genes and subsequently induce their expression. Chromatin immunoprecipitation (ChIP) assay demonstrated that IL-22 increased STAT3 binding in several sites on the SOX2 promoter area (FIG. 6G, H) and suggests that STAT3 directly activates stemness genes. Thus, IL-22 promotes colon cancer stemness via STAT3 activation.

Example IV

This example demonstrates that DOT1L regulates IL-22 dependent colon cancer stemness via H3K79 methylation.

Figure 9:
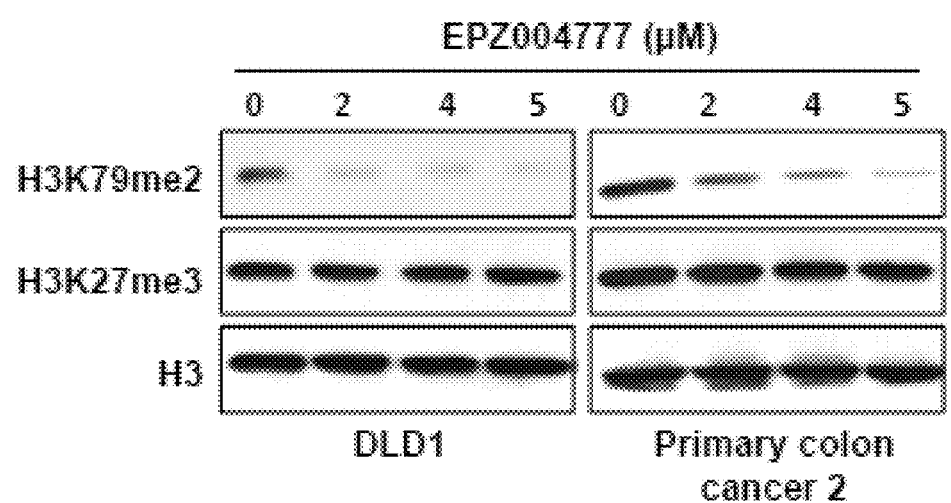
FIG. 9 demonstrates that EPZ004777 specifically inhibits H3K79 methylation. DLD1 and primary colon cancer cells (#2) were cultured with different concentrations of EPZ004777. Histone marks were detected by western blot. One of 4 experiments is shown.
Figure 10:
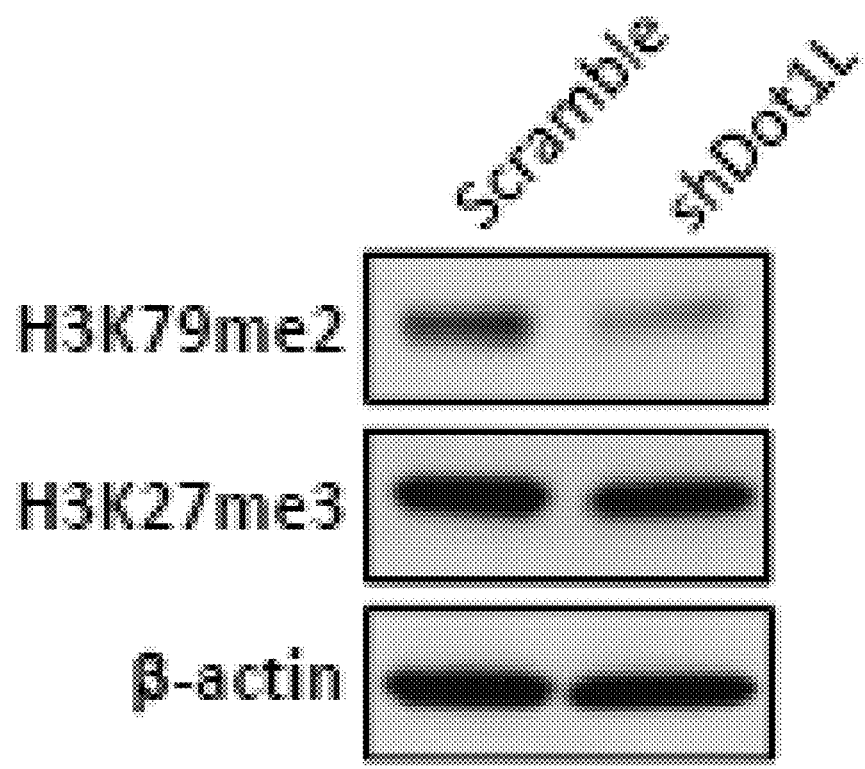
FIG. 10 demonstrates DOT1L knock down via shRNA. Colon cancer cells were transfected with control vectors or the shDOT1L vector. Histone marks were detected by Western blot. One of 4 experiments is shown.
Figure 11A:
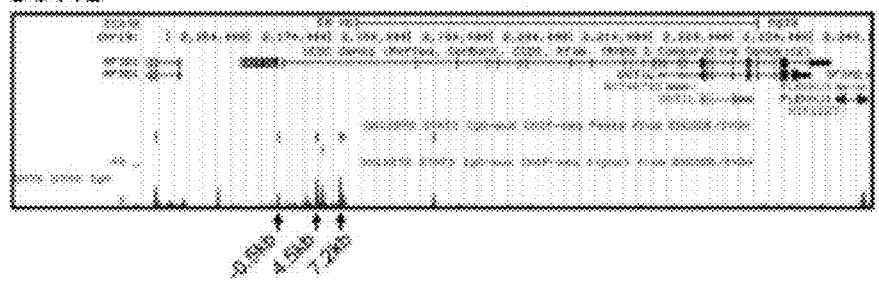
FIG. 11A-D demonstrates ENCODE STAT3-ChIP-Seq data base analysis. Based on the ENCODE STAT3-ChIP-Seq data base (Access number: GSM935557), STAT3 occupancy in the proximal promoter areas of DOT (A), AFF4 (B), MLLT3 (C) and MLLT10 (D) shown.
Figure 11B:
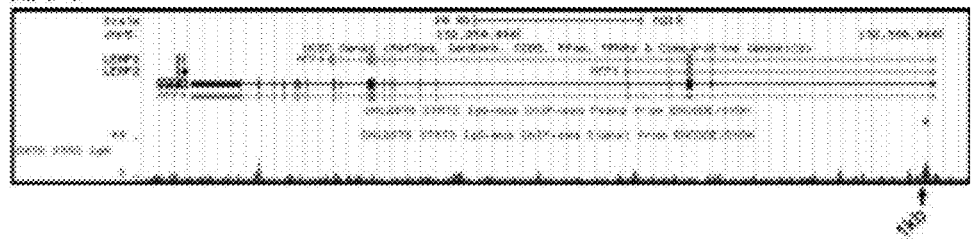
Figure 11C:
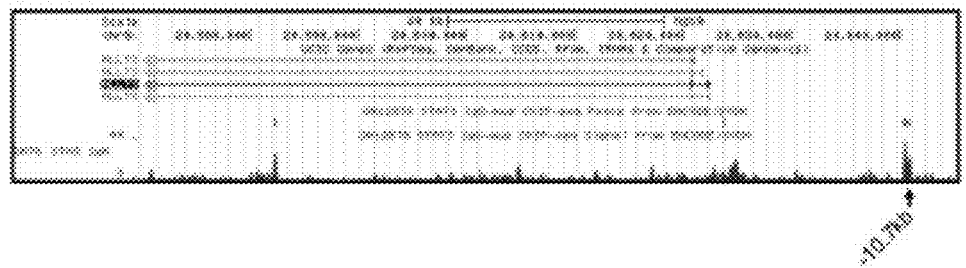
Figure 11D:
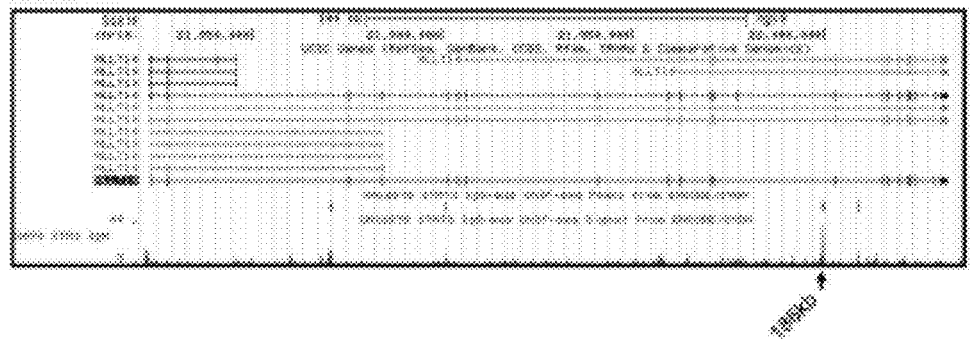

Epigenetic modifications of chromatin as well as crosstalk with transcription factors play an important role in the regulation of gene expression. STAT3 binding to the promoters of core stem cell genes is highly context dependent (see, e.g., Hutchins, A. P. et al. (2013) Nucleic Acids Res 41, 2155-2170). Thus, STAT3 activation may not explain the increase in stemness completely. As transcription factors and epigenetic modifications often guide external signals to a specific genetic response, it was wondered whether epigenetic control, including histone modifications, is involved in controlling IL-22 induced stemness gene expression. To this end, the global changes in several histone marks in IL-22 treated colon cancer cells were examined. Among several histone marks, it was observed that IL-22 selectively increased dimethylation of histone 3 lysine 79 (H3K79me2) (FIG. 8A). DOT1L is the sole H3K79 methyltransferase (see, e.g., Min, J., et al. (2003) Cell 112, 711-723; Ng, H. H. et al. (2002) Genes Dev 16, 1518-1527). EPZ004777 (see, e.g., Daigle, S. R. et al. (2011) Cancer Cell 20, 53-65; Yu, W. et al. (2012) Nat Commun 3, 1288), a selective inhibitor of DOT1L, reduced H3K79me2 (FIG. 9) and suppressed DLD-1 (FIG. 8B) and primary colon cancer (FIG. 8C) sphere formation. Several proteins recruit DOT1L to mediate methylation at H3K79 including AFF4 (MCEF), MLLT3 (AF9) and MLLT10 (AF10) (see, e.g., Mohan, M. et a. (2010) Genes Dev 24, 574-589). IL-22 consistently promoted the expression of DOT1L, AFF4, but not MLLLT10 in DLD-1 (FIG. 8D) and primary colon cancer cells (FIG. 8e). To further determine the role of DOT1L in colon cancer stemenss, DOT1L was inactivated with sh-DOT1L (FIG. 10). Similar to EPZ004777, DOT1L knockdown reduced colon cancer sphere formation (FIG. 8F). It was also explored whether IL-22 regulates H3K79me2 in core stem cell gene promoters. ChIP assays with H3K79me2 revealed an increase in H3K79me2 binding in the proximal promoter areas of NANOG (FIG. 8G), SOX2 (FIG. 8H) and POU5F1 (FIG. 8I) in an IL-22 dependent manner. Moreover, EPZ004777 treatment resulted in reduced H3K79me2 binding in the stem cell gene promoter sites (FIG. 8J-L). This data indicates that IL-22 regulates colon cancer stemness in a DOT1L/H3K79me2 dependent manner.

Example V

This example demonstrates that STAT3 and DOT1L cooperatively control IL-22-induced cancer stemness.

Both STAT3 (FIG. 6) and DOT1L/H3K79 signaling (FIG. 8) are involved in the control of IL-22-induced cancer stemness. It was hypothesized that IL-22-activated STAT3 causes H3K79 methylation. The ENCODE ChIP-sequence (ChIP-Seq) database revealed that STAT3 binds to the proximal promoters of DOT1L, AFF4, MLLT3 and MLLT10 in a lymphoblastoid cell line (Access number: GSM935557) (FIG. 11) (see, e.g., Birney, E., et al. (2007) Nature 447, 799-816). IL-22 treatment increased STAT3 binding to the DOT1L promoter area (FIG. 12A) and two other elements of the DOT1L complex, AFF4 (FIG. 12B) and MLLT3 (FIG. 12C), but not MLLT10. Thus, IL-22 promotes the interaction between the transcription factor STAT3 and the DOT1L complex to control colon cancer stemness.

Figure 12:
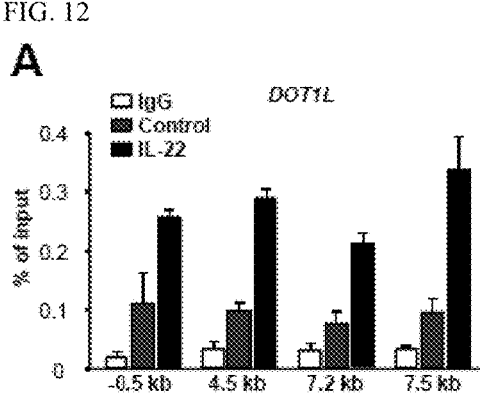
FIG. 12A-F demonstrates that STAT3 and DOT1L cooperatively control IL-22-induced cancer sternness. (A-C)IL-22 increases STAT3 occupancy on the DOT1L (A), AFF4 (B), and MLLT3 (C) proximal promoter. STAT3-ChIP assay was performed in DLD-1 colon cancer cells cultured with or without IL-22. One of three experiments is shown. (D-F) STAT3 knock down reduces H3K79me2 occupancy at proximal promoters of core stem cell genes. H3K79me2-ChIP was performed in colon cancer cells cultured with IL-22 for 24 hours. One of three experiments is shown.
Figure 12:
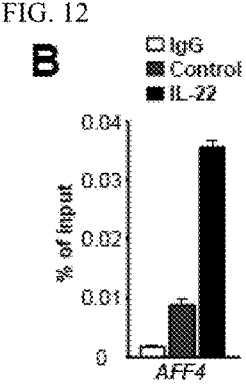
Figure 12:
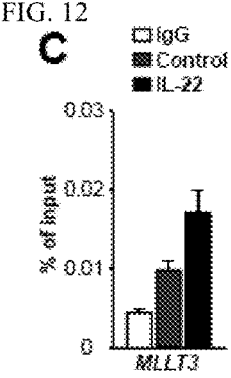
Figure 12:
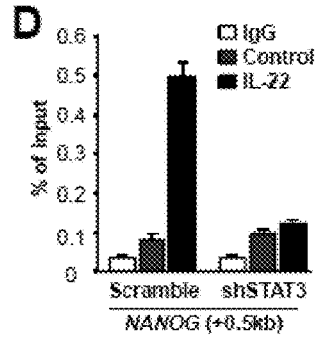
Figure 12:
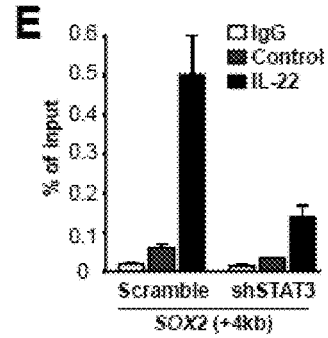
Figure 12:
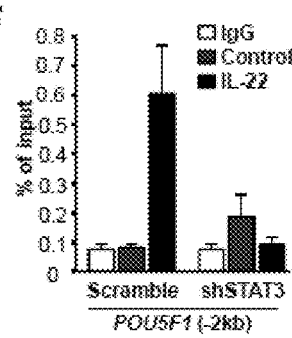

To determine whether STAT3 regulates stem cell core gene expression through DOT1L dependent H3K79 methylation we performed a ChIP assay with H3K79me2 in sh-STAT3 IL-22 treated colon cancer cells. STAT3 knock down abrogated IL-22-induced H3K79 methylation on the stem cell core gene promoters of NANOG, SOX2 and POU5F1 (FIG. 12D-F). Altogether, the data indicates that STAT3 directly regulates DOT1L expression and subsequently induces H3K79 methylation at the stemness genes, facilitating and accelerating stemness gene activation.

Example VI

This example demonstrates the clinical relevance of IL-22/DOT1L signaling pathway in cancer stemness.

The clinical relevance of the IL-22/DOT1L signaling pathway in colon cancer patients was investigated. To this end, the relationship between IL-22, DOT1L, and stem cell gene transcripts in patients with colorectal cancer from the National Center for Biotechnology Information Gene Expression Omnibus database (GSE17536) (see, e.g., Smith, J. J., et al. (2010) Gastroenterology 138, 958-968) was first examined. The GSE17536 data base includes 177 colorectal cancer patients with clinic and pathological information. It was showed that IL-22 expression correlated with DOT1L (FIG. 14A).

Figure 14:
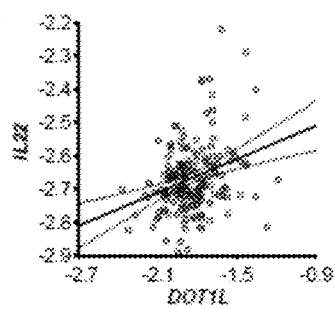
FIG. 14A-G demonstrates clinical relevance of H3K79/DOT1L in colon cancer stemness. (A, B) Correlation between IL-22, DOT1L and SOX2 transcripts in patients with colorectal cancer. The analyses were conducted in 177 colorectal cancer patients (GSE17536), P<0.05. (C) SOX2 transcripts are associated with patient survival. The analyses were conducted in 177 colon cancer patients (GSE17536), P<0.05. (D) Correlation between DOT1L and H3K79me2 in patients with colon cancer. n=144, P=0.005. (E, F) Tumor DOT1L (E) and H3K79me2 (F) expression levels are prognostic indicators of colon cancer overall survival. n=151, P=0.001 (E), n=144, P=0.039 (F). (G) Schematic figure shows how Th22 cells target STAT3 and DOT1L and control colon cancer stemness.
Figure 14:
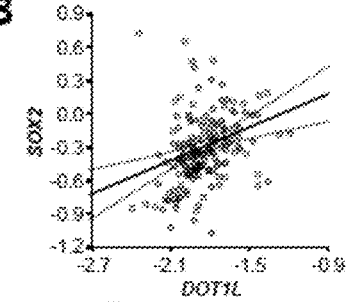
Figure 14:
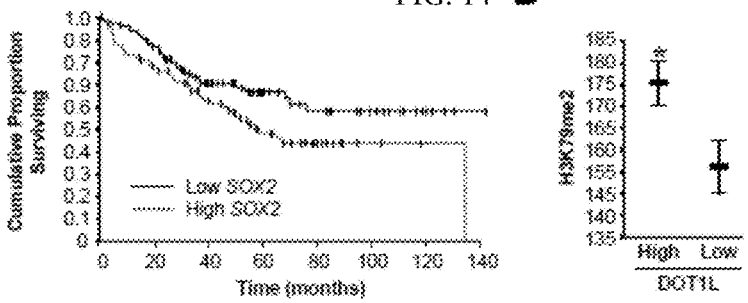
Figure 14:
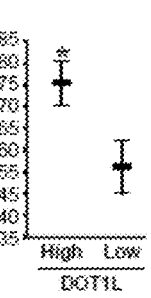
Figure 14:
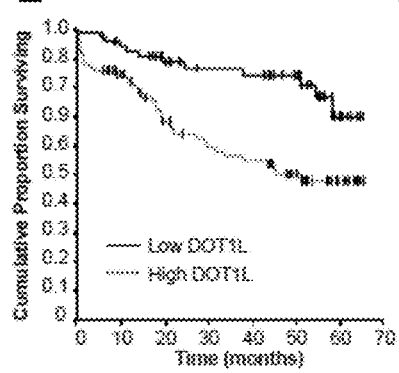
Figure 14:
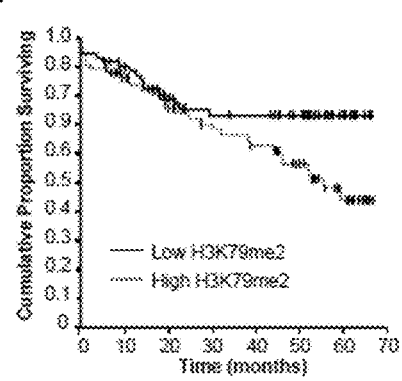
Figure 14:
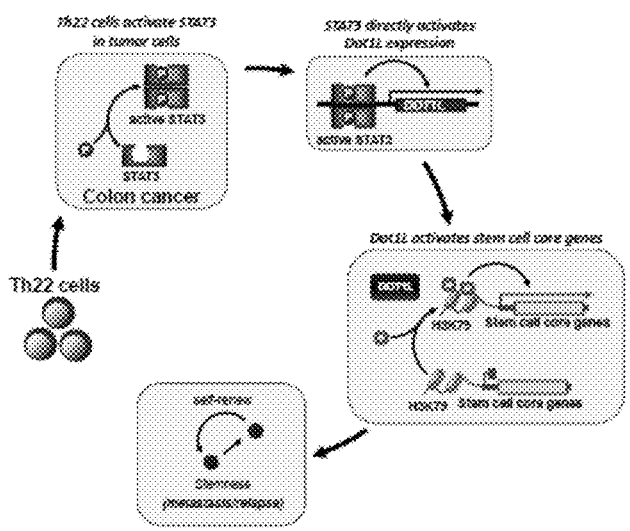
Figure 15:
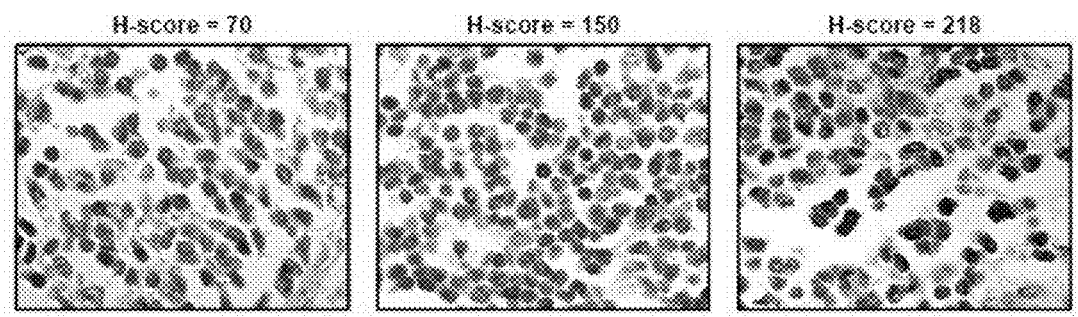
FIG. 15 demonstrates that immunohistochemical DOT1L scoring in colorectal cancers tissues. Colon cancer tissues were stained with anti-DOT1L antibody. Nuclear DOT1L+ tumor cells were quantified with the H-score as described in Methods. <the median values were considered low DOT expression, and ≥the median values were considered high DOT expression. Magnification: 400×.
Figure 16:
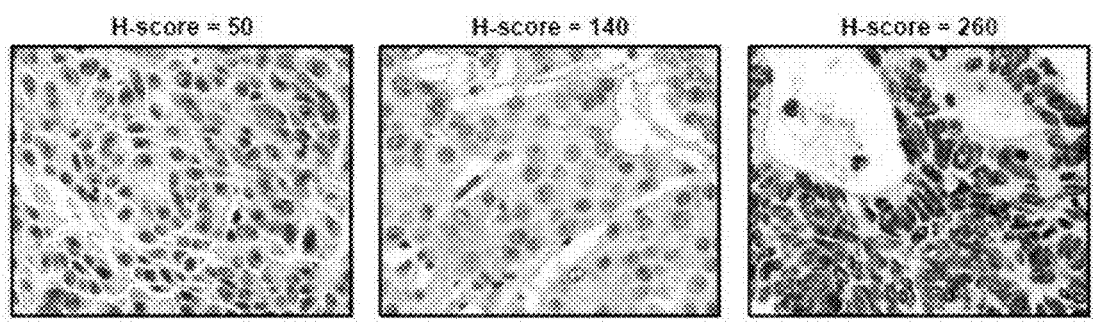
FIG. 16 demonstrates that immunohistochemical H3K79me2 scoring in colorectal cancers tissues Colon cancer tissues were stained with anti-H3K79me2 antibody. Nuclear H3K79me2+ tumor cells were quantified with the H-score as described in Methods. <the median values were considered low H3K79me2 expression, and ≥the median values were considered high H3K79me2 expression. Magnification: 400×.

Moreover, the expression levels of DOT1L correlated with SOX2 (FIG. 14B). Furthermore, when patients were divided into "low" and "high" groups based on the median value of SOX2, high levels of SOX2 associated with poor patient survival were observed (FIG. 14C). Then, the nuclear DOT1L (FIG. 15) and H3K79me2 levels (FIG. 15) were quantified via immunohistochemistry in paraffin-fixed colorectal cancer tissues from patients with available clinical and pathological information (Table 1). The expression of DOT1L highly correlated with that of H3K79me2 in the same tumor (FIG. 14D). Furthermore, based on the median values of DOT1L intensity, patients divided into "low" and "high" groups (FIG. 15). Overall survival was shorter in patients with high DOT1L staining compared to low DOT1L expression (Table 2, FIG. 14E). Age, and tumor stage (TNM) were important prognostic factors for colon cancer survival (Table 3). After adjusting for the clinical factors, overall survival remained shorter in patients with high DOT1L expression (Table 3). The data strongly suggest that increased tumor DOT1L abundance is a significant and independent predictor for poor survival in colorectal cancer. The relationship between tumor H3K79me2 expression and survival was further analyzed. Similar results were observed with H3K79 methylation (FIG. 16, FIG. 14F). Overall survival was shorter in patients with high H3K79 dimethylation (Table 2, FIG. 14F). Therefore, DOT1L/H3K79me2 could be a novel oncogenic predictor for poor survival in colorectal cancer. Altogether, Th22 cells produce IL-22 and shape colon cancer stemness via a coordinate interaction among STAT3, DOT1L and stem cell core genes (FIG. 14G).

TABLE 1

Colorectal cancer patient characteristics

|  |  | Overall survival | | |
|---|---|---|---|---|
|  |  | N (%) | P | HR (95% CI) |
| Age | ≤60 | 50 (33%) | <0.0009 | 1.045 (1.018, 1.073) |
|  | >60 | 101 (67%) |  |  |
| Gender | Female | 62 (41%) | NS | 1.049 (0.596, 1.848) |
|  | Male | 89 (59%) |  |  |
| T stage | T1 + T2 | 29 (19%) | 0.036 | 0.287 (0.089, 0.924) |
|  | T3 + T4 | 123 (81%) |  |  |
| N stage | N0 | 100 (66%) | 0.0008 | 0.383 (0.218, 0.673) |
|  | N1 + N2 + N3 | 51 (34%) |  |  |
| M stage | M0 | 125 (83%) | 0.016 | 0.456 (0.241, 0.864) |
|  | M1 | 26 (17%) |  |  |
| Differentiation | Well/moderate | 144 (95%) | NS | 0.894 (0.379, 2.106) |
|  | Poor | 5 (3%) |  |  |
| Localization of tumor | Distal colon | 25 (17%) | NS | 1.476 (0.763, 2.854) |
|  | Proximal colon | 100 (66%) |  |  |
|  | rectum | 26 (17%) |  | 0.916 (0.440, 1.906) |
| DOT1L | Low (<median) | 65 | 0.0018 | 2.820 (1.469, 5.413) |
|  | High (≥median) | 86 |  |  |
| H3K79me2 | Low (<median) | 70 | 0.045 | 1.835 (1.015, 3.316) |
|  | High (≥median) | 74 |  |  |

TABLE 2

Colorectal cancer patient characteristics

|  |  | DOT1L | | H3K79me2 | |
|---|---|---|---|---|---|
|  |  | Low | High | Low | High |
| Age | <60 | 25 (38%) | 25 (29%) | 24 (34%) | 22 (30%) |
|  | >60 | 40 (62%) | 61 (71%) | 46 (66%) | 52 (70%) |
| Gender | Female | 22 (34%) | 40 (47%) | 28 (40%) | 33 (45%) |
|  | Male | 43 (66%) | 46 (43%) | 42 (60%) | 41 (55%) |
| T stage | T1 + T2 | 8 (12%) | 20 (23%) | 12 (17%) | 16 (20%) |
|  | T3 + T4 | 57 (88%) | 66 (77%) | 58 (83%) | 59 (80%) |
| N stage | N0 | 39 (60%) | 61 (71%) | 41 (59%) | 52 (70%) |
|  | N1 + N2 + N3 | 26 (40%) | 25 (29%) | 29 (41%) | 22 (30%) |
| M stage | M0 | 53 (82%) | 72 (84%) | 58 (83%) | 61 (82%) |
|  | M1 | 12 (18%) | 14 (16%) | 12 (17%) | 13 (18%) |
| Differentiation | Well/moderate | 64 (98%) | 82 (95%) | 68 (97%) | 73 (97%) |
|  | Poor | 1 (2%) | 4 (5%) | 2 (3%) | 2 (3%) |
| Localization of tumor | Distal colon | 27 (42%) | 20 (23%) | 24 (34%) | 22 (30%) |
|  | Proximal colon | 22 (34%) | 25 (29%) | 27 (39%) | 19 (26%) |
|  | Rectum | 16 (25%) | 41 (48%) | 19 (27%) | 33 (45%) |

TABLE 3

Multivariate survival analysis

|  | P | HR (95% CI) |
|---|---|---|
| Age | <.0001 | 1.069 (1.037, 1.102) |
| Gender | NS | 0.775 (0.420, 1.432) |
| T stage | NS | 0.420 (0.122, 1.444) |
| N stage | 0.001 | 0.333 (0.170, 0.651) |
| M stage | 0.051 | 0.479 (0.228, 1.004) |
| Differentiation | NS | 1.141 (0.455, 2.864) |
| DOT1L | 0.0008 | 3.347 (1.646, 6.806) |
| H3K79me2 | NS | 1.003 (0.997, 1.010) |

Example VII

This example describes the materials and methods used for Examples I-VI.

Human Subjects

Patients diagnosed with colon carcinomas were recruited in the study. 151 formalin-fixed, paraffin-embedded tumor tissue blocks were obtained during surgery. These patients underwent resection of the primary tumor. The follow-up period was an average 2.8 years. Additional 177 patients with colon cancer were evaluated from the National Center for Biotechnology Information Gene Expression Omnibus database (GSE17536) (see, e.g., Smith, J. J., et al. (2010) Gastroenterology 138, 958-968). 36 fresh cancer tissues were collected from patients with colon cancer newly diagnosed. Primary colon cancer cells, immune cell subsets and all the in vitro and in vivo functional assays were performed with single cells from fresh colon cancer tissues and peripheral healthy donor blood.

Cell Isolation and FACS Analysis

Single cell suspension were prepared from fresh colon cancer tissues as previously described (see, e.g., Curiel, T. J. et al. (2004) Nat Med 10, 942-949; Curiel, T. J. et al. (2003) Nat Med 9, 562-567; Kryczek, I., et al. (2006) J Exp Med 203, 871-881; Zou, W., et al. (2001) Nat Med 7, 1339-1346). Immune cells and tumor cells were enriched using paramagnetic beads (StemCell Technology, Vancouver, Canada). $Lin^-CD45^-EpCAM^+$ cells primary colon cancer cells and $CD4^+CD33^+CD45^+$ T cells were sorted from stained single cell suspensions using a high speed cell sorter (FACSaria, Becton Dickinson Immunocytometry Systems, San Jose, Calif.). Cell purity was >98% as confirmed by flow cytometry (LSR II, BD). Cytokine profile was determined with intracellular staining and analyzed by LSRII (BD).

Cell Culture and Sphere Formation

Three primary colon cancer cell lines (1, 2, 3) were established from fresh colon cancer tissues. DLD1 and HT29 cell lines (ATCC) were used in the experiments. Colon cancer cells were treated with recombinant IL-22 (R&D systems) and/or colon cancer infiltrating $CD4^+$ T cells for different time points. The DOT1L inhibitor EPZ004777 (10 uM) and relevant antibodies were added in conventional or sphere culture (see, e.g., Kryczek, I. et al. (2012) Int J Cancer 130, 29-39). Tumor cell sphere formation and gene expression were examined (see, e.g., Kryczek, I. et al. (2012) Int J Cancer 130, 29-39).

Lentiviral Transduction pGIPZ Lentiviral vector encoding gene specific shRNAs for STAT3, DOT1L (Table 4) or scrambled shRNA (Puromycin resistant) were used to transduce colon cancer cells and establish stable cell lines by Puromycin selection. The lentiviral transduction efficiency was confirmed by GFP which was co-expressed by the lentiviral vector. The knockdown efficiency was assessed by western blotting.

TABLE 4

Sh-RNA Sequences

| Target Gene | Clone ID | Sequence |
|---|---|---|
| STAT3 (1) | V3LHS_641819 | ATTGCTGCAGGTCGTTGGT |
| STAT3 (2) | V2LHS_88502 | TACCTAAGGCCATGAACTT |
| DOT1L | V3LHS_391519 | AGTTGTTGAGCTTCTCGGG |

Cytokine Detection

The protein level of cytokines was detected either by ELISA (R & D) or flow cytometry analyzer (FACS) as described previously (see, e.g., Curiel, T. J. et al. (2004) Nat Med 10, 942-949; Kryczek, I., et al. (2011) Sci Transl Med 3, 104ra100). All samples were acquired with LSR II (BD) and analyzed with DIVA software.

Real-Time Reverse-Transcriptase Polymerase Chain Reaction (RT-PCR)

The mRNA was quantified by real-time RT-PCR. Specific primers are included in the supplementary information (Table 5). SYBR Green Master Mix was used to detect fluorescence. Relative expression was calculated according to the Ct value with normalization to GAPDH.

Migration Assays

Migration assays were performed in a Transwell system with a polycarbonate membrane of 6.5-mm diameter with a 3-μm pore size as described (see, e.g., Curiel, T. J. et al. (2004) Nat Med 10, 942-949; Curiel, T. J. et al. (2003) Nat Med 9, 562-567). Purified T cell subsets were added to the upper chamber and CCL-20 (5 ng/ml, R&D) was added to the lower chamber. After 4 h incubation at 37° C., the phenotype and number of T cells in the upper and lower chambers was determined by FACS.

Chromatin Immunoprecipitation (ChIP)

ChIP assay was performed according to the protocol with exceptions stated below (Upstate, Millipore; http://www.(followed by) millipore.com/techpublications/tech1/mcproto407). Crosslinking was performed with 1% formaldehyde or 1% paraformaldehyde for 10 minutes. To enhance cell lysis, the lysate was run through a 27 g needle three times and flash frozen in −80° C. Sonication was then performed with the Misonix 4000 water bath sonication unit at 15% amplitude for 10 minutes. Protein/DNA complex was precipitated with specific antibodies against H3K79me2 (abcam, ab3594), STAT3 (Santa Cruz, SC-482) and IgG control (Millipore). DNA was then purified using a DNA Purification Kit (Qiagen). ChIP-enriched chromatin was used for Real-Time PCR with SYBR Green Master Mix, normalizing to input. Specific primers are listed in Table 6.

TABLE 5

Real-Time PCR Primers

| Target Gene | Forward primer | SEQ ID NO: | Reverse primer | SEQ ID NO: |
|---|---|---|---|---|
| GAPDH | CTGCCCCCTCTGCTGATG | 4 | TCCACGATACCAAAGTTGTCATG | 12 |
| NANOG | AGGAAGACAAGGTCCCGGTCAA | 5 | GGTGCTGAGGCCTTCTGCGT | 13 |
| SOX2 | ATGCACCGCTACGACG | 6 | CTTTTGCACCCCTCCCATTT | 14 |
| POU5F1 | GAAGGTATTCAGCCAAACGA | 7 | AAATTCTCCAGGTTGCCTCT | 15 |
| IL22 | CTGGCCAGGCTCAGCAACAGG | 8 | CTTTGCTCTGGTCAAATGCAGGC | 16 |
| DOT1L | TCAAGATGACCGACGACGAC | 9 | CACCTCAGGACCAAAGGCAA | 17 |
| AFF4 | CCTTCCCACCCTAGCTCTCCT | 10 | GGTGGTACTGTAGGCTTGGG | 18 |
| MLLT10 | CTCTCACCCACACAACCGTA | 11 | TGTGTTGGTCCAGGGATCTG | 19 |

Western Blot

Western Blot assays were performed with specific antibodies against human STAT3 (9132, Cell Signaling), phosphorylated STAT3 (9138, Cell Signaling), Oct3/4 (sc-5279, Santa Cruz biotechnology), NANOG (ab21624, Abcam), SOX2 (MAB4343, Millipore), H3K79me2 (ab3594, Abcam), H3K9me2 (ab1220, Abcam), H3K9me3 (ab8898, Abcam), H4K20me3 (07-463, Millipore), H3K27me3 (07-449, Millipore), H3K36me3 (ab9050, Abcam), acetyl-Histone H3 (06-599, Millipore), Histone H3 (9715, Cell Signaling), β-Actin (A5441, Sigma), and α-TUBULIN (Santa Cruz) and Cleaved Notch1 (NICD, ab52301, Abcam). Signals were detected by ECL reagents (GE Healthcare, Buckinghamshire, UK).

TABLE 6

ChIP Primers

| Target Gene | Forward primer | SEQ ID NO: | Reverse primer | SEQ ID NO: |
|---|---|---|---|---|
| SOX2 (−8 kb) | AGTGCCCAACTTTCTAGGGC | 20 | TGGGCCACCCACTTGTTTAG | 42 |
| SOX2 (−7 kb) | TCAGACGGGCAGATAAGCAC | 21 | TGGGCTCAATGGTGTCAAGT | 43 |

TABLE 6-continued

ChIP Primers

| Target Gene | Forward primer | SEQ ID NO: | Reverse primer | SEQ ID NO: |
|---|---|---|---|---|
| SOX2 (-4 kb) | TAAGGCCTTTTGGCTAGGGC | 22 | TTCCACGGGCAACAAAAAGC | 44 |
| SOX2 (4 kb) | ACCAGGAACCAACAATCGGG | 23 | CTCAAGGGTGGAAGACGCTG | 45 |
| SOX2 (6 kb) | TTGTGGGAGCTCCATTGACG | 24 | GCGGTATTTCTTGTCCCCCT | 46 |
| NANOG (-9 kb) | ATAGGAGACCAAACGCGAGAA | 25 | TCTCGGCTATGACGGTTGCT | 47 |
| NANOG (-7 kb) | GACTCATCACTTTTGTGTAGCACC | 26 | ATTATGTGTTGACTACTTGGCCCT | 48 |
| NANOG (-1 kb) | TGTTAGTGCTGGAACCCCAC | 27 | AGACTACTCCGTGCCCATCT | 49 |
| NANOG (0.5 kb) | GGCACCTGCCCTTTGAACTA | 28 | TTTCCACCATGCCTAAGCCC | 50 |
| NANOG (4 kb) | TACCTCAGCCTCCAGCAGAT | 29 | GAGGCGATGTACGGACACAT | 51 |
| POU5F1 (-9 kb) | GACGGCTCTGACTTTCACTCA | 30 | TTGTCCACAAGAGATGGCCC | 52 |
| POU5F1 (-7 kb) | GTTGTGTGCCATGATGCTCC | 31 | GCAAGCCCCTTACGAGTCT | 53 |
| POU5F1 (-4 kb) | TAGCGGGACAGGGAAAAGTG | 32 | CTAAAGCCCTGGTGTGGAGG | 54 |
| POU5F1 (-2 kb) | CCTGGCAGATTGAGGGATGT | 33 | ACTAGACCAGCAGCATGAGC | 55 |
| POU5F1 (1 kb) | AATTGCTTACACTTGTCGCCT | 34 | CCTGGCACCCCTTGTAGAAA | 56 |
| DOT1L (-0.5 kb) | GGACCGTGACTCTTATGGGG | 35 | GGTTCGAATCCCGTCCCAG | 57 |
| DOT1L (4.5 kb) | GAGCAGTTCGGAAGGGGTTT | 36 | CATGCGGGCTTGAGAAAAG | 58 |
| DOT1L (7.2 kb) | ATCCCTGCATTGAGCCCTTC | 37 | TTTGAACCTTCCAGGGCCAG | 59 |
| DOT1L (7.5 kb) | GGGGGTAGCCCTGCTTTTAT | 38 | GCAGCAAGCCTGGATCTTG | 60 |
| AFF4 (1 kb) | CACGCACAAGCTACTGGGAT | 39 | CTTCGACTTGCGAAGGGGAT | 61 |
| MLLT3 (10.7 kb) | AGTCGTCAACCACTGCAAAC | 40 | CCCCAATTCACCCAGTGGTAA | 62 |
| MLLT10 (186 kb) | CAGTCAGCCTACTCATGGGAC | 41 | ACCGCCAGTAAGGCTTCAAT | 63 |

Immunohistochemistry (IHC)

Immunohistochemical staining on colon cancer tissue sections was performed on a DAKO Autostainer (DAKO, Carpinteria, Calif.) using DAKO LSAB+ and diaminobenzadine (DAB) as the chromogen. Serial sections of deparaffinized tissue sections were labeled with rabbit polyclonal antibodies against human KMT4/Dot1L, H3K79me2 and CCL20 (AbCam), or mouse anti-human VCAM1 antibody (6G9, Abcam). H3K79me2 and DOT1L were localized in the nuclei, and were scored using the H-score method (see, e.g., Pirker, R., et al. (2012) Lancet Oncol 13, 33-42).

The H-score is a method of assessing the extent of nuclear immunoreactivity. The H score takes into account the percentage of positive cells (0-100%) in each intensity category (0-3+) and computes a final score, on a continuous scale between 0 and 300. The score is obtained by the formula: (3×percentage of strongly staining nuclei)+(2×percentage of moderately staining nuclei)+(1×percentage of weakly staining nuclei), giving a range from 0 to 300 (see, e.g., Pirker, R., et al. (2012) Lancet Oncol 13, 33-42). Any discrepancies were resolved by subsequent consultation with a diagnostic pathologist. The tissues were divided into high and low H3K79me2 and DOT1L expression based on the median value of H3K79me2 and DOT1L expression levels per tissue section.

In Vivo Tumor Formation

Colon cancer cells ($10^2$-$5×10^6$) in 100 μl of buffered saline were subcutaneously injected into dorsal tissues of female NOD/Shi-scid/IL-2Rγnull (NSG) mice (6-8 weeks old, Jackson Lab, Bar Harbor, Me.) (see, e.g., Curiel, T. J. et al. (2004) Nat Med 10, 942-949; Curiel, T. J. et al. (2003) Nat Med 9, 562-567; Kryczek, I. et al. (2012) Int J Cancer 130, 29-39). Tumor size was measured two times weekly using calipers fitted with a Vernier scale. Tumor volume was calculated based on three perpendicular measurements (see, e.g., Curiel, T. J. et al. (2004) Nat Med 10, 942-949; Curiel, T. J. et al. (2003) Nat Med 9, 562-567). Tumor incidence was monitored.

Statistical Analysis

Wilcoxon rank-sum tests were used to compare two independent groups; for paired groups, Wilcoxon signed rank tests were used for comparison. Correlation coefficients (Spearman correlation, denoted by r, for ordinal data and Pearson correlation, denoted by r, for continuous data), together with a P-value (null hypothesis is that r is in fact zero), were computed to measure the degree of association between biomarkers. Log-rank test was used to compare time to tumor initiation between two groups. Overall patient survival was defined from date of diagnosis to disease related death. Data was censored at the last follow-up for patients who were disease-free or alive at the time of analysis. Survival functions were estimated by Kaplan-Meier methods. Cox's proportional hazards regression was performed to model survival (all classified as low and high based on the median value), after adjusting for age, grade and stage. The adequacy of the Cox regression model was assessed using graphical and numerical methods. All analyses were done using SAS 9.3 software. $P<0.05$ considered as significant.

Example VIII

This example demonstrates that IL-22 induces colon cancer proliferation. It has been reported that human Th22 cells express chemokine receptor CCR6 and CCR4 (see, e.g., Duhen, T., et al., (2009) Nat Immunol 10, 857-863; Crellin, N. K., et al., (2010) J Exp Med 207, 281-290), which can help T cells trafficking into cancer microenvironment (see, e.g., Cook, D. N., et al., (2000) Immunity 12, 495-503). Another chemokine receptor CXCR3 plays an important role in colon cancer lymphoid metastasis (see, e.g., Kawada, K., et al., (2007) Oncogene 26, 4679-4688). The following experiments address the mechanism of how IL-22 exists in colon cancer microenvironment.

JAK-STAT signaling plays a crucial role in epithelial proliferation, differentiation and apoptosis. STAT3 is a major activator of IL-22 prodution in many cells, which may participate in cell proliferation (see, e.g., Zheng, Y., et al., (2007) Nature 445, 648-651; Rutz, S., et al., (2013) Immunological reviews 252, 116-132). Aberrant STAT3 signaling promotes tumorigenesis and tumor progression partly through dysregulating some critical genes that control cell growth and survival, migration, invasion or metastasis (see, e.g., Darnell, J. E. (2005) Nature medicine 11, 595-596; Yue, P., and Turkson, J. (2009) Expert opinion on investigational drugs 18, 45-56; Jing, N., and Tweardy, D. J. (2005) Anticancer drugs 16, 601-607). It is well known that STAT3 signaling pathway is persistently activated in colorectal cancers and plays an important role in colon cancer development and patient survival (see, e.g., Corvinus, F. M., et al., (2005) Neoplasia 7, 545-555).

Histone methylation is an example of epigenetic modification, playing an important role in cancer development (see, e.g., Dawson, M. A., and Kouzarides, T. (2012) Cell 150, 12-27). Trimethylation of histone H3 lysine 27 (H3K27me3), catalyzed by the PcG enhancer of zeste homolog 2 (EZH2), is mainly related to gene repression (see, e.g., Barski, A., et al., (2007) Cell 129, 823-837). Such catalyzation requires the presence of two additional proteins, embryonic ectoderm development (EED) and suppressor of zeste 12 (SUZ12). EED and SUZ12 constitute the Polycomb Repression complex (PRC) 2 (see, e.g., Cao, R., and Zhang, Y. (2004) Curr Opin Genet Dev 14, 155-164). EZH2 is a H3K27 methyltransferase and is required for cell proliferation and over expressed in many cancers such as prostate cancer, breast cancer and colon cancers (see, e.g., Varambally, S., et al., (2002) Nature 419, 624-629; Kleer, C. G., et al., (2003) Proc Natl Acad Sci USA 100, 11606-11611; Mimori, K., et al., (2005) Eur J Surg Oncol 31, 376-380). H3K79me2 methylation through DOT1L is more associated with gene activation (see, e.g., Barski, A., et al., (2007) Cell 129, 823-837).

To analyze whether IL-22 associated with cell proliferation pathways, GSEA using high throughput RNA-sequencing data of the GC cohort of The Cancer Genomic Atlas project (TCGA) was performed. GSEA is designed to detect coordinated differences in expression of predefined sets of functionally related genes (see, e.g., Subramanian, A., et al., (2007) Bioinformatics 23, 3251-3253). Notably, the most significantly enriched functional categories (P<0.05) upon IL-22 positive profile are associated with multiple processes involved in cell proliferation (FIG. 17A), validating IL-22 as a potential critical regulator of colon cancer cell proliferation.

The effect of IL-22 on colon cell proliferation was next examined. FACS showed an increased expression of Ki-67 (FIG. 17B). Both H3Thymidine Incorporation (FIG. 17C) and cell number counting (FIG. 17D) showed IL-22 increased cell proliferation, while anti-IL-22 had a reverse effection (FIG. 17E).

The identification of target genes for IL-22 is essential for the determination of the mechanism by which it promotes proliferation in colon cancer cells. As such, the relative mRNA levels in DLD-1 colon cancer cell line was examined by real time quantitative PCR. As expected, IL-22 reduced the expression of the cyclin-dependent kinase inhibitors: p16 (CDKN2A), p18 (CDKN2C), p19 (CDKN2D), p21 (CDKN1A), p27 (CDKN1B), p53 and p57 (CDKN1C).

Figure 20:
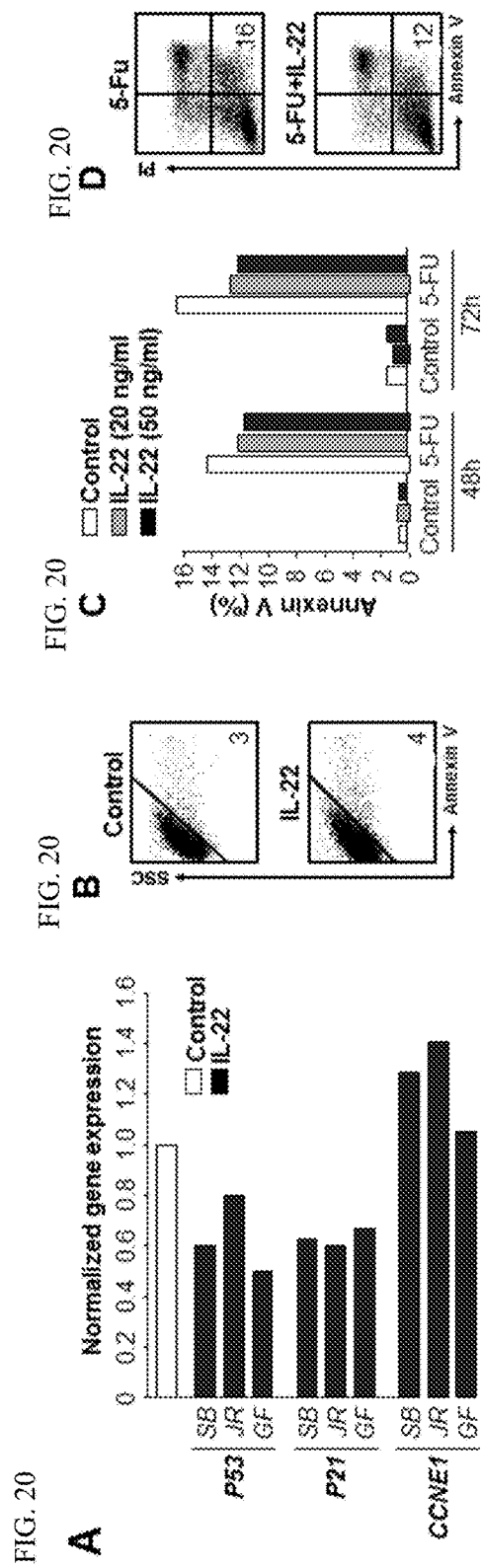
FIG. 20A-D A. Realtime PCR was used to detected the mRNA level of p53, p21, CCNE1 after stimulated with IL-22 in primary colon cancer cell lines. B. The effect of IL-22 on colon cancer cell apoptosis was analyzed by Annexin V using FACS. C.D The effect of IL-22 on 5-Fu induced apoptosis was also analyzed by Annexin V.

In addition, the expression of a number of 'positive regulatiors' of cell proliferation was tested. Consistently, IL-22 increased the mRNA levels of cyclin A1 (CCNA1), cyclin D1 (CCND1), cyclin D3 (CCND3), cyclin E1 (CCNE1), cyclin E2 (CCNE2) and CDK4 (FIG. 17F). These results were consistent with other primary colon cancer cell lines (FIG. 20A). The influence of IL-22 on cell apoptosis was tested, but no change was investigated after IL-22 stimulation alone or combined with 5-FU (FIGS. 20B, C and D).

Collectively, such results indicated IL-22 induces colon cancer proliferation.

Example IX

This example demonstrates that induction of colon cancer proliferation is H3K27m3 dependent.

To test whether DOT1L or EZH2 and SUZ12 are essential for proliferation, the inhibitor of DOT1L (EPZ00477) (see, e.g., Yu, W., et al., (2012) Nature communications 3, 1288), EZH2 (DZNep) (see, e.g., Tan, J., et al., (2007) Genes & development 21, 1050-1063), lentiviral vector encoding gene specific shRNAs (DOT1L, EZH2 and SUZ12), and scramble particles (Puromycin resistant) were used to transfect colon cancer cells and established stable cells. As shown in FIG. 18A, EPZ004777 had no influence on colon cancer cell proliferation induced by IL-22. shDOT1L was shown to specifically reduce H3K79m2, but also had no influence on cell proliferation stimulated by IL-22 (FIG. 18B, C). These results indicated that DOT1L was not involved in the cell proliferation induced by IL-22.

Thereafter, the correlation between EZH2 as well as SUZ12, EED and IL-22 on cell proliferation was investigated. As illustrated in FIG. 18D, IL-22 was shown to significantly increase the mRNA expression level of SUZ12, and EED was also increased to a lesser extent. Meanwhile, it was found that CBX8, a component of Polycomb PRC1, was increased (see, e.g., Tan, J., et al., (2011) Cancer cell 20, 563-575). Western blotting results showed that IL-22 increased EZH2 expression, while EED and SUZ12 was increased to a lesser extent (FIG. 18E). To further understand the relevance of PRC2 components and IL-22 in cell proliferation, DZNep was used to inhibit EZH2, and as shown in FIG. 18F, DZNep significantly blocked the cell proliferation induced by IL-22. Cells depleted for EZH2 and SUZ12 also showed reduced proliferation after IL-22 stimulation (FIG. 18G-J). To determine whether EZH2 and SUZ12 regulate the expression of p16 and p18, realtime PCR was used and the results showed knockdown of EZH2 or SUZ12 can increase the mRNA level of p16 and p18, no matter whether stimulated with IL-22 or not (FIG. 18K, L). Further more, as shown in FIG. 17F, IL-22 reduced the expression of p16 and p18. It was then found that the level of H3K27m3 in the promoter of p16 and p18 were both increased after IL-22 stimulation (FIG. 18M). These results were consistent with that of primary colon cancer cell line SBCA (FIG. 21). Taken together, all these data indicate that induction of colon cancer proliferation by IL-22 is H3K27m3, but not H3K79m2, dependent.

Example X

This example demonsrates that H3K27 methylation is STAT3 dependent.

Figure 19:
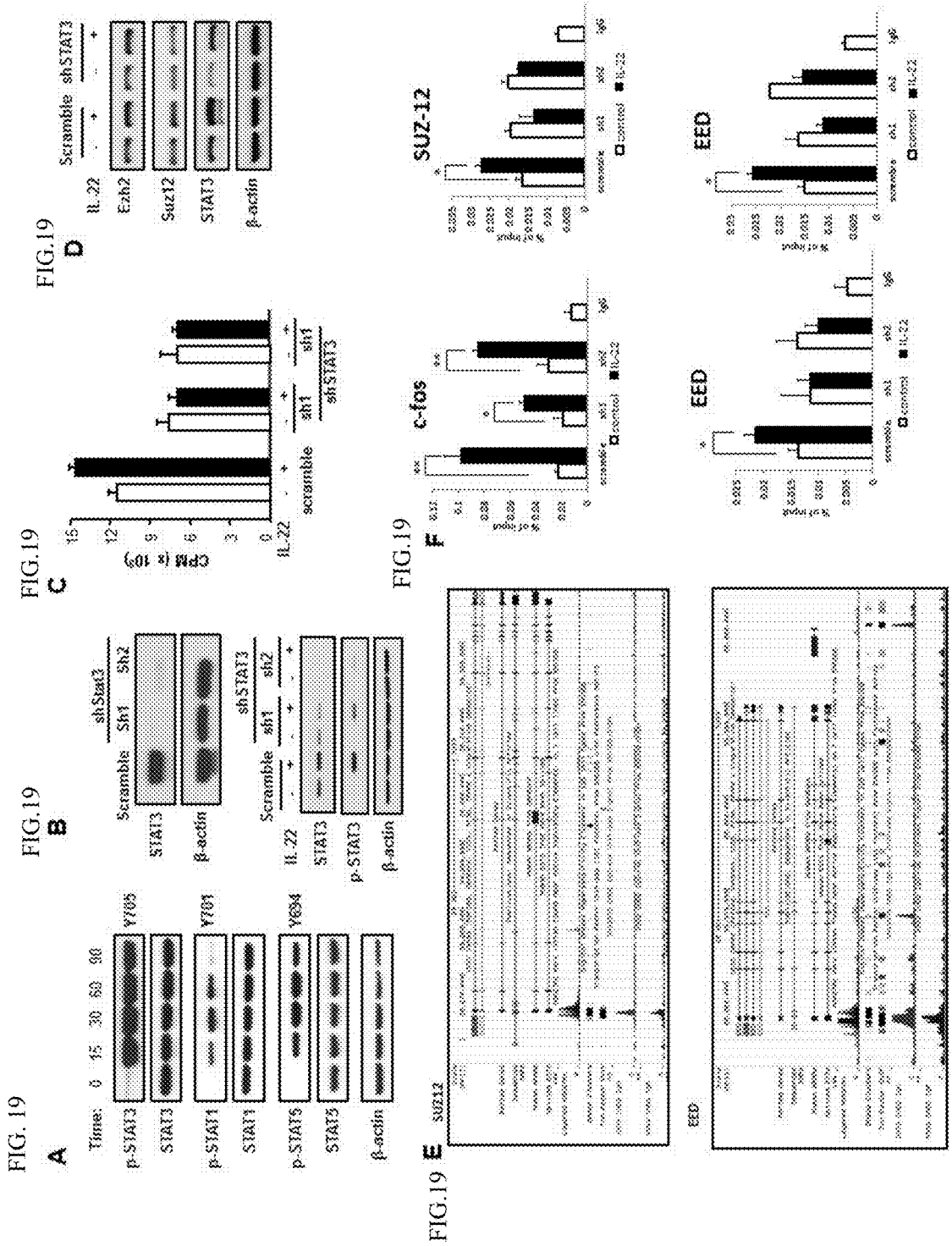
FIG. 19A-F demonstrates the effects of IL-22 on cell proliferation is Stat3 dependent. A. The protein level of phosphorylated STAT3, STAT1 and STAT5 were activated by IL-22. B. The effect of STAT3 knock down. C. The effect of IL-22 on cell proliferation was analyzed using $H^3$ Thymidine Incorporation in Stat3 knock down cells. D. Knock down of STAT3 reduced the expression of EZH2 and SUZ12. E. Based on the ENCODE STAT3-ChIP-Seq data base, STAT3 occupancy on the promoter areas of SUZ12 and EED is shown. F. SUZ12/EED DNA was detected by ChIP assay using an antibody against STAT3, c-fos was used as a positive control.

Previously, it was shown that IL-22 activated STAT3 strongly in colon cancer cells, and STAT1 and STAT5 to a smaller extent (FIG. 19A). To further examine whether the effect of IL-22 on colon cancer proliferation was STAT3 dependent, shSTAT3 was used to knock down the expression of STAT3 (FIG. 19B). shSTAT3 resulted in significant colon cancer cell proliferation reduction (FIG. 19C). IL-22 was shown to up regulate the protein level of EZH2 and SUZ12, while shSTAT3 reduced SUZ12 expression after IL-22 stimulated (FIG. 19D).

Figure 22:
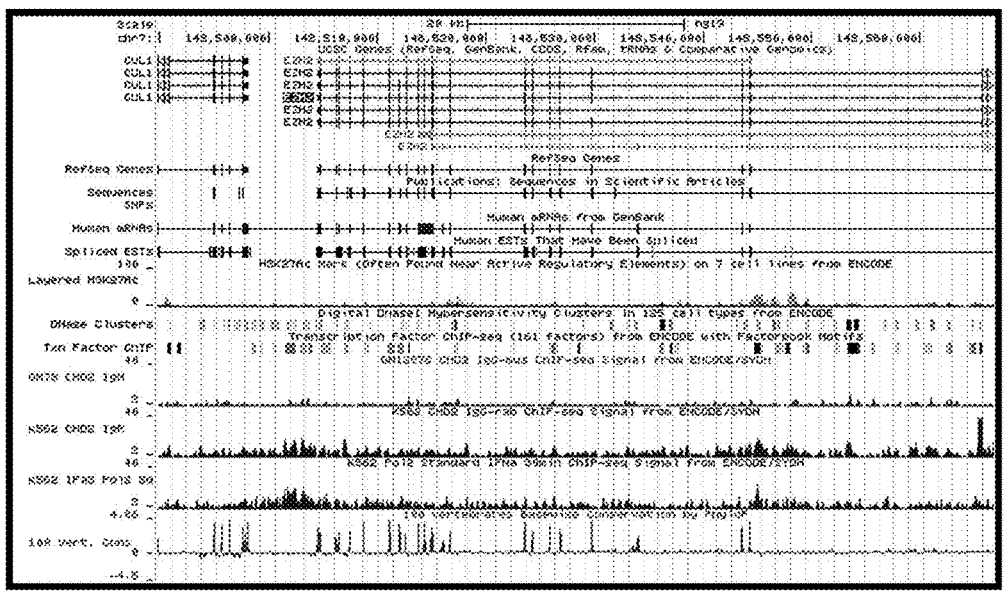
FIG. 22A-B A. EZH2 showed no binding position with STAT3 based on the ENCODE STAT3-ChIP-Seq data base. B. Knock down of EZH2 and SUZ12 had no influence on STAT3 activation.
Figure 22:
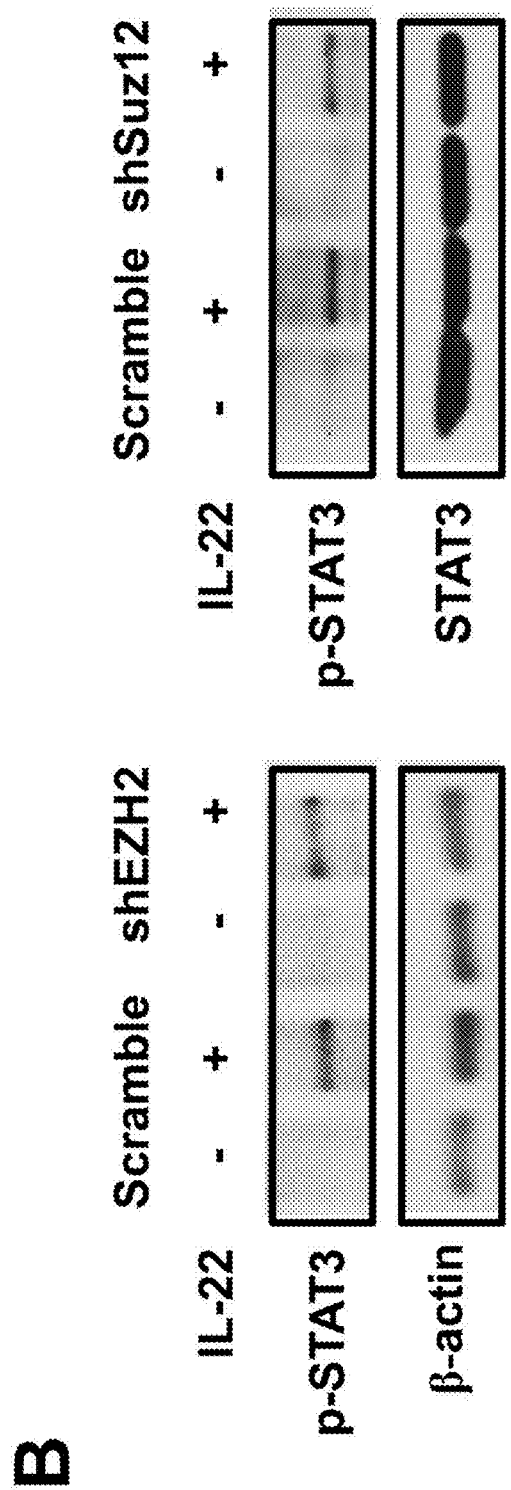

Bioinformatics analysis revealed that STAT3 had no binding position on EZH2 (FIG. 22A), but is able to bind to the promoter of other PRC2 genes such as SUZ12 and EED, which are thought to be the essential factors in cancer cell proliferation (FIG. 19E). This suggested that STAT3 may activate the SUZ12 and EED promoter. In ChIP assays, different pairs of primers in the SUZ12 and EED promoter were used, containing putative STAT3 binding sites. As shown in FIG. 19F, ChIP realtime PCR demonstrated that IL-22 significantly increased the recruitment of STAT3 to the SUZ12 and EED promoter. When STAT3 was knocked down, these effects were abrogated. It was further shown that EZH2 or SUZ12 knockdown didn't change the phosphorylation level of STAT3 after stimulated by IL-22 (FIG. 22).

Collectively, these data indicated that SUZ12 and EED was STAT3 dependent, which can be activated by IL-22.

Example XI

This example describes the materials and methods used for Examples VIII, IX and X.

Cell Culture and Sphere Formation

Three primary colon cancer cell lines (SB, WR, JR) were established from fresh colon tissues. These primary colon cancer cells and DLD1 (ATCC) were studied. Colon cancer cells were treated with recombinant IL-22 (R&D) for different time points. The EZH2 inhibitor DZNep was added in conventional or sphere culture (see, e.g., Kryczek, I., et al., (2012) International journal of cancer 130, 29-39). Tumor cell sphere formation and gene expression were examined (see, e.g., Kryczek, I., et al., (2012) International journal of cancer 130, 29-39).

Lentiviral Transduction

Lentiviral vector encoding gene specific shRNAs (STAT3, EZH2, SUZ12) and scramble particles (Puromycin resistant) were used to transduce colon cancer cells and established stable cells lines. The transduction efficiency was confirmed by vector GFP expression and Western blotting.

Real-Time Reverse-Transcriptase Polymerase Chain Reaction (RT-PCR)

The mRNAs were quantified by real-time RT-PCR. Specific primers are shown in Table 8. SYBR Green Master Mix was used to detect fluorescence. Relative expression was calculated according to the Ct value with normalization to GAPDH.

TABLE 8

Real-Time PCR primers

| Target gene | Forward primer | SEQ ID NO: | Reverse primer | SEQ ID NO: |
|---|---|---|---|---|
| GAPDH | GAAGGTGAAGGTCGGAGT | 64 | GAAGATGGTGATGGGATTTC | 84 |
| CCND1 | GGCCATGCTGAAGGCGGAGG | 65 | GCTCCAGCGACAGGAAGCGG | 85 |
| CCND3 | CCTCCAAGCTGCGCGAGACC | 66 | GGCAGAGAGAGCCGGTGCAG | 86 |
| CCNE1 | AGCCCCATCATGCCGAGGGA | 67 | TGGGGATCAGGGAGCAGGG | 87 |
| CCNE2 | TGAGCCGAGCGGTAGCTGGT | 68 | GGGATTCCGTCTGGCTGGGC | 88 |
| CCNA1 | GTGGAGTTGTGCTGGCTAC | 69 | TCAGGGAGTGCTTTCTTT | 89 |
| CDK4 | CACTCTGGTACCGAGCTCCCGA | 70 | GGCTCCACGGGGCAGGGATA | 90 |
| p16 | ATGCCGCGGAAGGTCCCTCA | 71 | AAAGCGGGGTGGGTTGTGGC | 91 |
| p18 | GGAACGAGTTGGCGTCCGCA | 72 | GGAAACCTGCTCTGGCCGCA | 92 |
| p19 | GAGCTGGTGCATCCCGACG | 73 | GGGCAGGAGAAACAAGAAGAGAAAG | 93 |
| p21 | GCCCAGTGGACAGCGAGCAG | 74 | GCCGGCGTTTGGAGTGGTAGA | 94 |
| p27 | GCGACCTGCAACCGACGATTCT | 75 | GAGGCCAGGCTTCTTGGGCG | 95 |
| p53 | TTTGAGGTGCGTGTTTGT | 76 | GGCGGGAGGTAGACTGA | 96 |
| p57 | CTGACCAGCTGCACTCGGGGATTTC | 77 | GCCGCCGGTTGCTGCTACATGA | 97 |
| EZH2 | TGCAGTTGCTTCAGTACCCATAAT | 78 | ATCCCCGTGTACTTTCCCATCATAAT | 98 |

TABLE 8-continued

Real-Time PCR primers

| Target gene | Forward primer | SEQ ID NO: | Reverse primer | SEQ ID NO: |
|---|---|---|---|---|
| Suz12 | TGGGAGACTATTCTTGATGGGAAG | 79 | GGAGCCGTAGATTTATCATTGGTC | 99 |
| EED | GCCTGCGGCCAAGAAGCAGA | 80 | TCCAGGTGCATTTGGCGTGT | 100 |
| BMI-1 | TGCTGATGCTGCCAATGG | 81 | TTACTTTCCGATCCAATCTGTTCTG | 101 |
| RIN1A | GAATACGAGGCCCATCAAGA | 82 | GCTCACATCTTCTCCATCCC | 102 |
| CBX8 | GATGGTCGCAGAAGTACAGCAC | 83 | GCTTTGAGGAGGAAGGTTTTGG | 103 |

Western Blot

Western Blot assay was performed with specific antibodies against human Stat3, phosphorylate Stat3 (Cell Signaling), Sox2, SUZ12(Santa Cruz biotechnology), EZH2 (Abcam), H3K27me3 and H3K79me2 (Millipore).

Chromatin Immunoprecipitation (ChIP)

ChIP assay was performed according to the protocol (Upstate, Millipore; htt, followed by, p://www.millip, followed by, ore.com/techpublica, followed by, tions/tech1/mcproto407). Crosslinking was performed with 1% formaldehyde or 1% paraformaldehyde for 10 min. To enhance cell lysis, we ran the lysate through a 27 g needle three times and flash froze it in −80° C. Sonication was then performed with the Misonix 4000 water bath sonication unit at 15% amplitude for 10 min. Protein/DNA complex was precipitated by specific antibodies against H3K79me2, H3K27me3 (Millipore), Stat3 (Cell Signaling) and IgG control (Millipore). Then DNA was purified using DNA Purification Kit (Qiagen). ChIP-enriched chromatin was used for Real-Time PCR, relative expression level is normalized to Input. Specific primers are listed in supplementary information (Table 9).

TABLE 9

ChIP primers

| Target gene | Forward primer | SEQ ID NO: | Reverse primer | SEQ ID NO: |
|---|---|---|---|---|
| SUZ12 (TSS) | CCCGGAATTCTGCTTTTTCTACCT | 104 | CAGTTTCACCTTCCAGACAGAAC | 108 |
| EED (TSS-1) | AGGGAGGCGGAGGAATATGT | 105 | CTTTCACTCCGCAGTCTCGT | 109 |
| EED (TSS-2) | ACTGTGGAATTTCTTAGGCTGATG | 106 | CAGAGGATGGCTCGTATTGCT | 110 |
| c-fos | GCAGCCCGCGAGCAGTT | 107 | GCCTTGGCGCGTGTCCTAATC | 111 |
| p16 (−0.3 kb) | | | | |
| p16 (−0.6 kb) | | | | |
| p18 | | | | |

Statistical Analyses

Statistical analyses were done with SAS 9.3 software. All Student's t tests were two-sided and p values less than 0.05 were considered significant.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method of treating colorectal cancer characterized with activated cancer stem cells in a subject, the method comprising administering to said subject an agent that down regulates the expression, amount or activity of DOT1L, wherein said administering inhibits cancer stem cell activation within colorectal cancer cells, wherein the agent is a DOT1L inhibiting agent, wherein the DOT1L inhibiting agent is a pharmaceutical composition comprising EPZ5676.

* * * * *

SEQUENCE LISTING

```
<160> NUMBER OF SEQ ID NOS: 111

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
attgctgcag gtcgttggt                                                  19

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
tacctaaggc catgaactt                                                  19

<210> SEQ ID NO 3
<211> LENGTH: 19
<212> TYPE: DNA
<213> ORGANISM: Artificial sequence
<220> FEATURE:
<223> OTHER INFORMATION: Synthetic

<400> SEQUENCE: 3
agttgttgag cttctcggg                                                  19

<210> SEQ ID NO 4
<211> LENGTH: 18
<212> TYPE: DNA
<213> ORGANISM: Artificial sequence
<220> FEATURE:
<223> OTHER INFORMATION: Synthetic

<400> SEQUENCE: 4
ctgccccctc tgctgatg                                                   18

<210> SEQ ID NO 5
<211> LENGTH: 22
<212> TYPE: DNA
<213> ORGANISM: Artificial sequence
<220> FEATURE:
<223> OTHER INFORMATION: Synthetic

<400> SEQUENCE: 5
aggaagacaa ggtcccggtc aa                                              22

<210> SEQ ID NO 6
```

```
<211> LENGTH: 16
<212> TYPE: DNA
<213> ORGANISM: Artificial sequence
<220> FEATURE:
<223> OTHER INFORMATION: Synthetic

<400> SEQUENCE: 6
atgcaccgct acgacg                                                         16

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7
gaaggtattc agccaaacga                                                     20

<210> SEQ ID NO 8
<211> LENGTH: 21
<212> TYPE: DNA
<213> ORGANISM: Artificial sequence
<220> FEATURE:
<223> OTHER INFORMATION: Synthetic

<400> SEQUENCE: 8
ctggccaggc tcagcaacag g                                                   21

<210> SEQ ID NO 9
<211> LENGTH: 20
<212> TYPE: DNA
<213> ORGANISM: Artificial sequence
<220> FEATURE:
<223> OTHER INFORMATION: Synthetic

<400> SEQUENCE: 9
tcaagatgac cgacgacgac                                                     20

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
ccttcccacc tagctctcct                                                     20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
ctctcaccca cacaaccgta                                                     20

<210> SEQ ID NO 12
<211> LENGTH: 23
<212> TYPE: DNA
<213> ORGANISM: Artificial sequence
<220> FEATURE:
<223> OTHER INFORMATION: Synthetic

<400> SEQUENCE: 12
```

-continued

```
tccacgatac caaagttgtc atg                                              23

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
ggtgctgagg ccttctgcgt                                                  20

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
cttttgcacc cctcccattt                                                  20

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
aaattctcca ggttgcctct                                                  20

<210> SEQ ID NO 16
<211> LENGTH: 23
<212> TYPE: DNA
<213> ORGANISM: Artificial sequence
<220> FEATURE:
<223> OTHER INFORMATION: Synthetic

<400> SEQUENCE: 16
ctttgctctg gtcaaatgca ggc                                              23

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
cacctcagga ccaaaggcaa                                                  20

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
ggtggtactg taggcttggg                                                  20

<210> SEQ ID NO 19
<211> LENGTH: 20
<212> TYPE: DNA
```

```
<213> ORGANISM: Artificial sequence
<220> FEATURE:
<223> OTHER INFORMATION: Synthetic

<400> SEQUENCE: 19
tgtgttggtc cagggatctg                                                    20

<210> SEQ ID NO 20
<211> LENGTH: 20
<212> TYPE: DNA
<213> ORGANISM: Artificial sequence
<220> FEATURE:
<223> OTHER INFORMATION: Synthetic

<400> SEQUENCE: 20
agtgcccaac tttctagggc                                                    20

<210> SEQ ID NO 21
<211> LENGTH: 20
<212> TYPE: DNA
<213> ORGANISM: Artificial sequence
<220> FEATURE:
<223> OTHER INFORMATION: Synthetic

<400> SEQUENCE: 21
tcagacgggc agataagcac                                                    20

<210> SEQ ID NO 22
<211> LENGTH: 20
<212> TYPE: DNA
<213> ORGANISM: Artificial sequence
<220> FEATURE:
<223> OTHER INFORMATION: Synthetic

<400> SEQUENCE: 22
taaggccttt tggctagggc                                                    20

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
accaggaacc aacaatcggg                                                    20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
ttgtgggagc tccattgacg                                                    20

<210> SEQ ID NO 25
<211> LENGTH: 21
<212> TYPE: DNA
<213> ORGANISM: Artificial sequence
<220> FEATURE:
<223> OTHER INFORMATION: Synthetic

<400> SEQUENCE: 25
ataggagacc aaacgcgaga a                                                  21
```

```
<210> SEQ ID NO 26
<211> LENGTH: 24
<212> TYPE: DNA
<213> ORGANISM: Artificial sequence
<220> FEATURE:
<223> OTHER INFORMATION: Synthetic

<400> SEQUENCE: 26
gactcatcac ttttgtgtag cacc                                          24

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
tgttagtgct ggaacccac                                                20

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
ggcacctgcc ctttgaacta                                               20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
tacctcagcc tccagcagat                                               20

<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
gacggctctg actttcactc a                                             21

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
gttgtgtgcc atgatgctcc                                               20

<210> SEQ ID NO 32
<211> LENGTH: 20
<212> TYPE: DNA
<213> ORGANISM: Artificial sequence
<220> FEATURE:
```

<223> OTHER INFORMATION: Synthetic

<400> SEQUENCE: 32
tagcgggaca gggaaaagtg                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
cctggcagat tgagggatgt                                               20

<210> SEQ ID NO 34
<211> LENGTH: 21
<212> TYPE: DNA
<213> ORGANISM: Artificial sequence
<220> FEATURE:
<223> OTHER INFORMATION: Synthetic

<400> SEQUENCE: 34
aattgcttac acttgtcgcc t                                             21

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
ggaccgtgac tcttatgggg                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
gagcagttcg gaagggggttt                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
atccctgcat tgagcccttc                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
gggggtagcc ctgcttttat                                               20

```
<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
cacgcacaag ctactgggat                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
agtcgtcaac cactgcaaac                                               20

<210> SEQ ID NO 41
<211> LENGTH: 21
<212> TYPE: DNA
<213> ORGANISM: Artificial sequence
<220> FEATURE:
<223> OTHER INFORMATION: Synthetic

<400> SEQUENCE: 41
cagtcagcct actcatggga c                                             21

<210> SEQ ID NO 42
<211> LENGTH: 20
<212> TYPE: DNA
<213> ORGANISM: Artificial sequence
<220> FEATURE:
<223> OTHER INFORMATION: Synthetic

<400> SEQUENCE: 42
tgggccaccc acttgtttag                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic

<400> SEQUENCE: 43
tgggctcaat ggtgtcaagt                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic

<400> SEQUENCE: 44
ttccacgggc aacaaaaagc                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic
```

<400> SEQUENCE: 45
ctcaagggtg gaagacgctg                                                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
gcggtatttc ttgtccccct                                                                               20

<210> SEQ ID NO 47
<211> LENGTH: 20
<212> TYPE: DNA
<213> ORGANISM: Artificial sequence
<220> FEATURE:
<223> OTHER INFORMATION: Synthetic

<400> SEQUENCE: 47
tctcggctat gacggttgct                                                                               20

<210> SEQ ID NO 48
<211> LENGTH: 24
<212> TYPE: DNA
<213> ORGANISM: Artificial sequence
<220> FEATURE:
<223> OTHER INFORMATION: Synthetic

<400> SEQUENCE: 48
attatgtgtt gactacttgg ccct                                                                          24

<210> SEQ ID NO 49
<211> LENGTH: 20
<212> TYPE: DNA
<213> ORGANISM: Artificial sequence
<220> FEATURE:
<223> OTHER INFORMATION: Synthetic

<400> SEQUENCE: 49
agactactcc gtgcccatct                                                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic

<400> SEQUENCE: 50
tttccaccat gcctaagccc                                                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic

<400> SEQUENCE: 51
gaggcgatgt acggacacat                                                                               20

<210> SEQ ID NO 52
<211> LENGTH: 20

```
<212> TYPE: DNA
<213> ORGANISM: Artificial sequence
<220> FEATURE:
<223> OTHER INFORMATION: Synthetic

<400> SEQUENCE: 52
ttgtccacaa gagatggccc                                                      20

<210> SEQ ID NO 53
<211> LENGTH: 20
<212> TYPE: DNA
<213> ORGANISM: Artificial sequence
<220> FEATURE:
<223> OTHER INFORMATION: Synthetic

<400> SEQUENCE: 53
gcaagcccct tacgaagtct                                                      20

<210> SEQ ID NO 54
<211> LENGTH: 20
<212> TYPE: DNA
<213> ORGANISM: Artificial sequence
<220> FEATURE:
<223> OTHER INFORMATION: Synthetic

<400> SEQUENCE: 54
ctaaagccct ggtgtggagg                                                      20

<210> SEQ ID NO 55
<211> LENGTH: 20
<212> TYPE: DNA
<213> ORGANISM: Artificial sequence
<220> FEATURE:
<223> OTHER INFORMATION: Synthetic

<400> SEQUENCE: 55
actagaccag cagcatgagc                                                      20

<210> SEQ ID NO 56
<211> LENGTH: 20
<212> TYPE: DNA
<213> ORGANISM: Artificial sequence
<220> FEATURE:
<223> OTHER INFORMATION: Synthetic

<400> SEQUENCE: 56
cctggcaccc cttgtagaaa                                                      20

<210> SEQ ID NO 57
<211> LENGTH: 19
<212> TYPE: DNA
<213> ORGANISM: Artificial sequence
<220> FEATURE:
<223> OTHER INFORMATION: Synthetic

<400> SEQUENCE: 57
ggttcgaatc ccgtcccag                                                       19

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
```
catgcggggc ttgagaaaag                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
tttgaacctt ccagggccag                                               20

<210> SEQ ID NO 60
<211> LENGTH: 19
<212> TYPE: DNA
<213> ORGANISM: Artificial sequence
<220> FEATURE:
<223> OTHER INFORMATION: Synthetic

<400> SEQUENCE: 60
gcagcaagcc tggatcttg                                                19

<210> SEQ ID NO 61
<211> LENGTH: 20
<212> TYPE: DNA
<213> ORGANISM: Artificial sequence
<220> FEATURE:
<223> OTHER INFORMATION: Synthetic

<400> SEQUENCE: 61
cttcgacttg cgaaggggat                                               20

<210> SEQ ID NO 62
<211> LENGTH: 21
<212> TYPE: DNA
<213> ORGANISM: Artificial sequence
<220> FEATURE:
<223> OTHER INFORMATION: Synthetic

<400> SEQUENCE: 62
ccccaattca cccagtggta a                                             21

<210> SEQ ID NO 63
<211> LENGTH: 20
<212> TYPE: DNA
<213> ORGANISM: Artificial sequence
<220> FEATURE:
<223> OTHER INFORMATION: Synthetic

<400> SEQUENCE: 63
accgccagta aggcttcaat                                               20

<210> SEQ ID NO 64
<211> LENGTH: 18
<212> TYPE: DNA
<213> ORGANISM: Artificial sequence
<220> FEATURE:
<223> OTHER INFORMATION: Synthetic

<400> SEQUENCE: 64
gaaggtgaag gtcggagt                                                 18

<210> SEQ ID NO 65
<211> LENGTH: 20
<212> TYPE: DNA
<213> ORGANISM: Artificial sequence

```
<220> FEATURE:
<223> OTHER INFORMATION: Synthetic

<400> SEQUENCE: 65
ggccatgctg aaggcggagg                                                    20

<210> SEQ ID NO 66
<211> LENGTH: 20
<212> TYPE: DNA
<213> ORGANISM: Artificial sequence
<220> FEATURE:
<223> OTHER INFORMATION: Synthetic

<400> SEQUENCE: 66
cctccaagct gcgcgagacc                                                    20

<210> SEQ ID NO 67
<211> LENGTH: 20
<212> TYPE: DNA
<213> ORGANISM: Artificial sequence
<220> FEATURE:
<223> OTHER INFORMATION: Synthetic

<400> SEQUENCE: 67
agccccatca tgccgaggga                                                    20

<210> SEQ ID NO 68
<211> LENGTH: 20
<212> TYPE: DNA
<213> ORGANISM: Artificial sequence
<220> FEATURE:
<223> OTHER INFORMATION: Synthetic

<400> SEQUENCE: 68
tgagccgagc ggtagctggt                                                    20

<210> SEQ ID NO 69
<211> LENGTH: 19
<212> TYPE: DNA
<213> ORGANISM: Artificial sequence
<220> FEATURE:
<223> OTHER INFORMATION: Synthetic

<400> SEQUENCE: 69
gtggagttgt gctggctac                                                     19

<210> SEQ ID NO 70
<211> LENGTH: 22
<212> TYPE: DNA
<213> ORGANISM: Artificial sequence
<220> FEATURE:
<223> OTHER INFORMATION: Synthetic

<400> SEQUENCE: 70
cactctggta ccgagctccc ga                                                 22

<210> SEQ ID NO 71
<211> LENGTH: 20
<212> TYPE: DNA
<213> ORGANISM: Artificial sequence
<220> FEATURE:
<223> OTHER INFORMATION: Synthetic

<400> SEQUENCE: 71
atgccgcgga aggtccctca                                                    20
```

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
ggaacgagtt ggcgtccgca                                               20

<210> SEQ ID NO 73
<211> LENGTH: 19
<212> TYPE: DNA
<213> ORGANISM: Artificial sequence
<220> FEATURE:
<223> OTHER INFORMATION: Synthetic

<400> SEQUENCE: 73
gagctggtgc atcccgacg                                                19

<210> SEQ ID NO 74
<211> LENGTH: 20
<212> TYPE: DNA
<213> ORGANISM: Artificial sequence
<220> FEATURE:
<223> OTHER INFORMATION: Synthetic

<400> SEQUENCE: 74
gcccagtgga cagcgagcag                                               20

<210> SEQ ID NO 75
<211> LENGTH: 22
<212> TYPE: DNA
<213> ORGANISM: Artificial sequence
<220> FEATURE:
<223> OTHER INFORMATION: Synthetic

<400> SEQUENCE: 75
gcgacctgca accgacgatt ct                                            22

<210> SEQ ID NO 76
<211> LENGTH: 18
<212> TYPE: DNA
<213> ORGANISM: Artificial sequence
<220> FEATURE:
<223> OTHER INFORMATION: Synthetic

<400> SEQUENCE: 76
tttgaggtgc gtgtttgt                                                 18

<210> SEQ ID NO 77
<211> LENGTH: 25
<212> TYPE: DNA
<213> ORGANISM: Artificial sequence
<220> FEATURE:
<223> OTHER INFORMATION: Synthetic

<400> SEQUENCE: 77
ctgaccagct gcactcgggg atttc                                         25

<210> SEQ ID NO 78
<211> LENGTH: 24
<212> TYPE: DNA
<213> ORGANISM: Artificial sequence
<220> FEATURE:
<223> OTHER INFORMATION: Synthetic

<400> SEQUENCE: 78
tgcagttgct tcagtaccca taat                                    24

<210> SEQ ID NO 79
<211> LENGTH: 24
<212> TYPE: DNA
<213> ORGANISM: Artificial sequence
<220> FEATURE:
<223> OTHER INFORMATION: Synthetic

<400> SEQUENCE: 79
tgggagacta ttcttgatgg gaag                                    24

<210> SEQ ID NO 80
<211> LENGTH: 20
<212> TYPE: DNA
<213> ORGANISM: Artificial sequence
<220> FEATURE:
<223> OTHER INFORMATION: Synthetic

<400> SEQUENCE: 80
gcctgcggcc aagaagcaga                                         20

<210> SEQ ID NO 81
<211> LENGTH: 18
<212> TYPE: DNA
<213> ORGANISM: Artificial sequence
<220> FEATURE:
<223> OTHER INFORMATION: Synthetic

<400> SEQUENCE: 81
tgctgatgct gccaatgg                                           18

<210> SEQ ID NO 82
<211> LENGTH: 20
<212> TYPE: DNA
<213> ORGANISM: Artificial sequence
<220> FEATURE:
<223> OTHER INFORMATION: Synthetic

<400> SEQUENCE: 82
gaatacgagg cccatcaaga                                         20

<210> SEQ ID NO 83
<211> LENGTH: 22
<212> TYPE: DNA
<213> ORGANISM: Artificial sequence
<220> FEATURE:
<223> OTHER INFORMATION: Synthetic

<400> SEQUENCE: 83
gatggtcgca gaagtacagc ac                                      22

<210> SEQ ID NO 84
<211> LENGTH: 20
<212> TYPE: DNA
<213> ORGANISM: Artificial sequence
<220> FEATURE:
<223> OTHER INFORMATION: Synthetic

<400> SEQUENCE: 84
gaagatggtg atgggatttc                                         20

<210> SEQ ID NO 85

```
<211> LENGTH: 20
<212> TYPE: DNA
<213> ORGANISM: Artificial sequence
<220> FEATURE:
<223> OTHER INFORMATION: Synthetic

<400> SEQUENCE: 85
gctccagcga caggaagcgg                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic

<400> SEQUENCE: 86
ggcagagaga gccggtgcag                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic

<400> SEQUENCE: 87
tggggatcag ggagcagggg                                              20

<210> SEQ ID NO 88
<211> LENGTH: 20
<212> TYPE: DNA
<213> ORGANISM: Artificial sequence
<220> FEATURE:
<223> OTHER INFORMATION: Synthetic

<400> SEQUENCE: 88
gggattccgt ctggctgggc                                              20

<210> SEQ ID NO 89
<211> LENGTH: 18
<212> TYPE: DNA
<213> ORGANISM: Artificial sequence
<220> FEATURE:
<223> OTHER INFORMATION: Synthetic

<400> SEQUENCE: 89
tcagggagtg ctttctttc                                               18

<210> SEQ ID NO 90
<211> LENGTH: 20
<212> TYPE: DNA
<213> ORGANISM: Artificial sequence
<220> FEATURE:
<223> OTHER INFORMATION: Synthetic

<400> SEQUENCE: 90
ggctccacgg ggcagggata                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic

<400> SEQUENCE: 91
```
aaagcggggt gggttgtggc					20

<210> SEQ ID NO 92
<211> LENGTH: 20
<212> TYPE: DNA
<213> ORGANISM: Artificial sequence
<220> FEATURE:
<223> OTHER INFORMATION: Synthetic

<400> SEQUENCE: 92
ggaaacctgc tctggccgca					20

<210> SEQ ID NO 93
<211> LENGTH: 25
<212> TYPE: DNA
<213> ORGANISM: Artificial sequence
<220> FEATURE:
<223> OTHER INFORMATION: Synthetic

<400> SEQUENCE: 93
gggcaggaga acaagaaga gaaag				25

<210> SEQ ID NO 94
<211> LENGTH: 21
<212> TYPE: DNA
<213> ORGANISM: Artificial sequence
<220> FEATURE:
<223> OTHER INFORMATION: Synthetic

<400> SEQUENCE: 94
gccggcgttt ggagtggtag a					21

<210> SEQ ID NO 95
<211> LENGTH: 20
<212> TYPE: DNA
<213> ORGANISM: Artificial sequence
<220> FEATURE:
<223> OTHER INFORMATION: Synthetic

<400> SEQUENCE: 95
gaggccaggc ttcttgggcg					20

<210> SEQ ID NO 96
<211> LENGTH: 17
<212> TYPE: DNA
<213> ORGANISM: Artificial sequence
<220> FEATURE:
<223> OTHER INFORMATION: Synthetic

<400> SEQUENCE: 96
ggcgggaggt agactga					17

<210> SEQ ID NO 97
<211> LENGTH: 22
<212> TYPE: DNA
<213> ORGANISM: Artificial sequence
<220> FEATURE:
<223> OTHER INFORMATION: Synthetic

<400> SEQUENCE: 97
gccgccggtt gctgctacat ga				22

<210> SEQ ID NO 98
<211> LENGTH: 26
<212> TYPE: DNA

```
<213> ORGANISM: Artificial sequence
<220> FEATURE:
<223> OTHER INFORMATION: Synthetic

<400> SEQUENCE: 98
atccccgtgt actttcccat cataat                                              26

<210> SEQ ID NO 99
<211> LENGTH: 24
<212> TYPE: DNA
<213> ORGANISM: Artificial sequence
<220> FEATURE:
<223> OTHER INFORMATION: Synthetic

<400> SEQUENCE: 99
ggagccgtag atttatcatt ggtc                                                24

<210> SEQ ID NO 100
<211> LENGTH: 20
<212> TYPE: DNA
<213> ORGANISM: Artificial sequence
<220> FEATURE:
<223> OTHER INFORMATION: Synthetic

<400> SEQUENCE: 100
tccaggtgca tttggcgtgt                                                     20

<210> SEQ ID NO 101
<211> LENGTH: 25
<212> TYPE: DNA
<213> ORGANISM: Artificial sequence
<220> FEATURE:
<223> OTHER INFORMATION: Synthetic

<400> SEQUENCE: 101
ttactttccg atccaatctg ttctg                                               25

<210> SEQ ID NO 102
<211> LENGTH: 20
<212> TYPE: DNA
<213> ORGANISM: Artificial sequence
<220> FEATURE:
<223> OTHER INFORMATION: Synthetic

<400> SEQUENCE: 102
gctcacatct tctccatccc                                                     20

<210> SEQ ID NO 103
<211> LENGTH: 22
<212> TYPE: DNA
<213> ORGANISM: Artificial sequence
<220> FEATURE:
<223> OTHER INFORMATION: Synthetic

<400> SEQUENCE: 103
gctttgagga ggaaggtttt gg                                                  22

<210> SEQ ID NO 104
<211> LENGTH: 24
<212> TYPE: DNA
<213> ORGANISM: Artificial sequence
<220> FEATURE:
<223> OTHER INFORMATION: Synthetic

<400> SEQUENCE: 104
cccggaattc tgcttttct acct                                                 24
```

<210> SEQ ID NO 105
<211> LENGTH: 20
<212> TYPE: DNA
<213> ORGANISM: Artificial sequence
<220> FEATURE:
<223> OTHER INFORMATION: Synthetic

<400> SEQUENCE: 105
agggaggcgg aggaatatgt                                              20

<210> SEQ ID NO 106
<211> LENGTH: 24
<212> TYPE: DNA
<213> ORGANISM: Artificial sequence
<220> FEATURE:
<223> OTHER INFORMATION: Synthetic

<400> SEQUENCE: 106
actgtggaat tcttaggct gatg                                          24

<210> SEQ ID NO 107
<211> LENGTH: 17
<212> TYPE: DNA
<213> ORGANISM: Artificial sequence
<220> FEATURE:
<223> OTHER INFORMATION: Synthetic

<400> SEQUENCE: 107
gcagcccgcg agcagtt                                                 17

<210> SEQ ID NO 108
<211> LENGTH: 23
<212> TYPE: DNA
<213> ORGANISM: Artificial sequence
<220> FEATURE:
<223> OTHER INFORMATION: Synthetic

<400> SEQUENCE: 108
cagtttcacc ttccagacag aac                                          23

<210> SEQ ID NO 109
<211> LENGTH: 20
<212> TYPE: DNA
<213> ORGANISM: Artificial sequence
<220> FEATURE:
<223> OTHER INFORMATION: Synthetic

<400> SEQUENCE: 109
ctttcactcc gcagtctcgt                                              20

<210> SEQ ID NO 110
<211> LENGTH: 21
<212> TYPE: DNA
<213> ORGANISM: Artificial sequence
<220> FEATURE:
<223> OTHER INFORMATION: Synthetic

<400> SEQUENCE: 110
cagaggatgg ctcgtattgc t                                            21

<210> SEQ ID NO 111
<211> LENGTH: 21
<212> TYPE: DNA
<213> ORGANISM: Artificial sequence
<220> FEATURE:

-continued

```
<223> OTHER INFORMATION: Synthetic

<400> SEQUENCE: 111
gccttggcgc gtgtcctaat c                                        21
```